(12) United States Patent
Lin et al.

(10) Patent No.: US 10,596,116 B2
(45) Date of Patent: *Mar. 24, 2020

(54) METAL BISPHOSPHONATE NANOPARTICLES FOR ANTI-CANCER THERAPY AND IMAGING AND FOR TREATING BONE DISORDERS

(71) Applicant: The University of North Carolina at Chapel Hill, Chapel Hill, NC (US)

(72) Inventors: Wenbin Lin, Chicago, IL (US); Demin Liu, Round Lake, IL (US); Joseph Della Rocca, Blue Bell, PA (US); Stephanie Kramer, Chapel Hill, NC (US); Christopher Y. Poon, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/613,847

(22) Filed: Jun. 5, 2017

(65) Prior Publication Data

US 2017/0333347 A1    Nov. 23, 2017

Related U.S. Application Data

(63) Continuation of application No. 14/131,575, filed as application No. PCT/US2012/045954 on Jul. 9, 2012, now Pat. No. 9,693,957.

(60) Provisional application No. 61/505,806, filed on Jul. 8, 2011.

(51) Int. Cl.

| | |
|---|---|
| *A61K 51/00* | (2006.01) |
| *A61K 9/127* | (2006.01) |
| *A61K 47/69* | (2017.01) |
| *A61K 9/14* | (2006.01) |
| *A61K 9/00* | (2006.01) |
| *A61K 9/51* | (2006.01) |
| *A61P 19/10* | (2006.01) |
| *A61P 19/08* | (2006.01) |
| *A61K 47/54* | (2017.01) |
| *A61P 35/00* | (2006.01) |
| *A61K 31/663* | (2006.01) |
| *A61K 31/675* | (2006.01) |
| *A61K 49/00* | (2006.01) |
| *A61K 51/12* | (2006.01) |

(52) U.S. Cl.
CPC .......... *A61K 9/127* (2013.01); *A61K 9/0019* (2013.01); *A61K 9/14* (2013.01); *A61K 9/5115* (2013.01); *A61K 9/5123* (2013.01); *A61K 9/5146* (2013.01); *A61K 31/663* (2013.01); *A61K 31/675* (2013.01); *A61K 47/548* (2017.08); *A61K 47/6925* (2017.08); *A61K 47/6929* (2017.08); *A61K 49/00* (2013.01); *A61K 51/1244* (2013.01); *A61P 19/08* (2018.01); *A61P 19/10* (2018.01); *A61P 35/00* (2018.01)

(58) Field of Classification Search
CPC .......... A61K 9/00; A61K 9/127; A61K 47/00; A61K 47/6929; A61K 9/0019; A61K 9/5123; A61K 9/5146; A61K 9/14; A61K 9/5115; A61K 31/00; A61K 31/663; A61K 31/675; A61K 49/00; A61K 51/00; A61K 51/1244; A61K 2121/00; A61K 2123/00; A61K 51/0489; A61K 51/0478; A61K 47/4884; A61K 47/548; A61P 19/10; A61P 19/08; A61P 35/00
USPC ..... 424/1.11, 1.61, 1.65, 1.77, 9.1, 9.2, 400, 424/78.08, 1.21, 1.29, 1.81, 1.85; 977/773

See application file for complete search history.

(56) References Cited

U.S. PATENT DOCUMENTS

| | | |
|---|---|---|
| 4,405,771 A | 9/1983 | Jagur |
| 5,147,806 A | 9/1992 | Kamin et al. |
| 5,213,788 A | 5/1993 | Ranney |
| 5,591,730 A * | 1/1997 | Stoller ................... A61K 31/66 424/601 |
| 5,641,623 A | 6/1997 | Martin |
| 5,827,925 A | 10/1998 | Tremont et al. |
| 5,858,784 A | 1/1999 | Debs et al. |
| 5,871,710 A | 2/1999 | Bogdanov et al. |
| 6,013,638 A | 1/2000 | Crystal et al. |
| 6,022,737 A | 2/2000 | Niven et al. |
| 6,136,295 A | 10/2000 | Edwards et al. |
| 6,180,082 B1 | 1/2001 | Woltering et al. |

(Continued)

FOREIGN PATENT DOCUMENTS

| | | |
|---|---|---|
| CN | 1 673 258 | 9/2005 |
| CN | 102573914 A | 7/2012 |

(Continued)

OTHER PUBLICATIONS

PubChem Open Chemistry Database, Platinum 2+, date unavailable.*

(Continued)

*Primary Examiner* — D. L. Jones
(74) *Attorney, Agent, or Firm* — Jenkins, Wilson, Taylor & Hunt, P.A.

(57) ABSTRACT

Metal-bisphosphonate nanoparticles are disclosed. Also disclosed are pharmaceutical compositions including the metal-bisphosphonate nanoparticles, methods of preparing the metal-bisphosphonate nanoparticles and materials comprising the nanoparticles, and methods of using the compositions to treat cancer or bone-related disorders (e.g., bone-resorption-related diseases, osteoporosis, Paget's disease, and bone metastases) and as imaging agents.

19 Claims, 32 Drawing Sheets

(56) References Cited

U.S. PATENT DOCUMENTS

| | | | |
|---|---|---|---|
| 6,384,019 B1 | 5/2002 | Myhren et al. | |
| 6,878,838 B2* | 4/2005 | Lin | B01J 31/1625 |
| | | | 502/162 |
| 6,984,400 B2* | 1/2006 | Golomb | A61K 9/127 |
| | | | 424/450 |
| 7,354,912 B2* | 4/2008 | Lichtenberger | A61K 31/663 |
| | | | 514/141 |
| 7,704,972 B2 | 4/2010 | Couvreur et al. | |
| 7,803,785 B2 | 9/2010 | Gallop et al. | |
| 8,158,153 B2* | 4/2012 | Liversidge | A61K 9/0019 |
| | | | 424/400 |
| 8,653,292 B2 | 2/2014 | Hafizovic et al. | |
| 8,722,018 B2* | 5/2014 | Port | A61K 49/0428 |
| | | | 424/9.3 |
| 9,072,774 B2 | 7/2015 | Zheng et al. | |
| 9,693,957 B2* | 7/2017 | Lin | A61K 9/14 |
| 10,517,822 B2 | 12/2019 | Lin et al. | |
| 2001/0018187 A1 | 8/2001 | Sun et al. | |
| 2002/0115747 A1 | 8/2002 | Feldheim et al. | |
| 2002/0187184 A1* | 12/2002 | Golomb | A61K 9/127 |
| | | | 424/450 |
| 2005/0147963 A1 | 7/2005 | Su et al. | |
| 2006/0204754 A1 | 9/2006 | Kang | |
| 2006/0210639 A1 | 9/2006 | Liversidge et al. | |
| 2006/0228554 A1 | 10/2006 | Tan et al. | |
| 2006/0233883 A1 | 10/2006 | Ishihara et al. | |
| 2007/0088161 A1 | 4/2007 | Stockel et al. | |
| 2008/0045699 A1 | 2/2008 | Labow et al. | |
| 2008/0063714 A1 | 3/2008 | Sahouani et al. | |
| 2008/0095699 A1 | 4/2008 | Zheng et al. | |
| 2008/0124281 A1 | 5/2008 | Gao et al. | |
| 2008/0280851 A1 | 11/2008 | Myhren et al. | |
| 2008/0286352 A1 | 11/2008 | Kumar et al. | |
| 2008/0292714 A1 | 11/2008 | Garlich et al. | |
| 2009/0317335 A1 | 12/2009 | Lin et al. | |
| 2011/0053862 A1 | 3/2011 | Xie et al. | |
| 2011/0135571 A1 | 6/2011 | Lin et al. | |
| 2011/0238001 A1 | 9/2011 | Chen et al. | |
| 2011/0281815 A1 | 11/2011 | Ahrabi et al. | |
| 2012/0142641 A1* | 6/2012 | Venkatraman | A61K 47/48861 |
| | | | 514/107 |
| 2012/0253191 A1 | 10/2012 | Zheng et al. | |
| 2012/0301537 A1 | 11/2012 | Ishida et al. | |
| 2013/0171228 A1 | 7/2013 | Morris | |
| 2014/0107333 A1 | 4/2014 | Ma et al. | |
| 2014/0127763 A1 | 5/2014 | Zheng et al. | |
| 2014/0234210 A1 | 8/2014 | Lin et al. | |
| 2014/0235568 A1 | 8/2014 | Song et al. | |
| 2016/0346204 A1 | 12/2016 | Lin et al. | |

FOREIGN PATENT DOCUMENTS

| | | |
|---|---|---|
| EP | 2729180 B1 | 1/2019 |
| EP | 3494974 A1 | 6/2019 |
| JP | 2010-523595 A | 7/2010 |
| JP | 6590802 B2 | 10/2019 |
| WO | WO 2004/028508 A1 | 4/2004 |
| WO | WO 2006/087722 A1 | 8/2006 |
| WO | WO2006/102117 | 9/2006 |
| WO | WO2007/090295 | 8/2007 |
| WO | WO2007/108618 | 9/2007 |
| WO | WO2007/124131 | 11/2007 |
| WO | WO 2008/016172 A1 | 2/2008 |
| WO | WO 2008/124639 A2 | 10/2008 |
| WO | WO 2009/014532 A1 | 1/2009 |
| WO | WO2009/139939 | 11/2009 |
| WO | WO 2010/065751 A2 | 6/2010 |
| WO | WO2012/042024 | 4/2012 |
| WO | WO2013/009701 | 1/2013 |
| WO | WO 2013/068965 | 5/2013 |
| WO | WO 2012/161196 A1 | 7/2014 |
| WO | WO2015/069926 | 5/2015 |
| WO | WO 2015/149068 A1 | 10/2015 |
| WO | WO 2015/149072 A1 | 10/2015 |

OTHER PUBLICATIONS

Che et al., "Generation of Binuclear (d8.d8) Platinum and Rhodium Complexes by Pulse Radiolysis", American Chemical Society, vol. 106, No. 18, pp. 5143-5145 (1984).

Coleman, et al., "Latest research and clinical treatment of advanced-stage epithelial ovarian cancer," Nat Rev Clin Oncol, vol. 10, pp. 211-224 (2013).

Cutler et al., "Spherical Nucleic Acids," Journal of the American Chemical Society, 134, p. 1376-1391 (2012).

Brannon-Peppas et al., "Nanoparticle and targeted systems for cancer therapy," Advanced Drug Delivery Reviews. vol. 56 pp. 1649-1659 (2004).

Bowden et al., "Hydrothermal syntheses and crystal structures of three zinc succinates: $Zn(C4H4O4)-\alpha$, $Zn(C4H4O4)-\beta$ and $K2Zn(C4H4O4)2$," Dalton Transactions. pp. 936-939 (2003).

Catala et al., "Cyanide-Bridged CrIII-NiII Superparamagnetic Nanoparticles," Advanced Materials. vol. 15, No. 10 pp. 826-829 (2003).

Cavka et al., "A new zirconium inorganic building brick forming metal organic frameworks with exceptional stability," J Am Chem Soc, vol. 130, pp. 13850-13851 (2008).

Chebbi et al., "In vitro assessment of liposomal neridronate on MDA-MB-231 human breast cancer cells," International Journal of Pharmaceutics 383 pp. 116-122 (2010).

Chen et al., "Synthesis, characterization and osteoconductivity properties of bone fillers based on alendronate-loaded poly(e-caprolactone)/hydroxyapatite microspheres," J Mater Sci. vol. 22 pp. 547-555 (2011).

Chen et al., "Co-delivery of Doxorubicin and Bcl-2 siRNA by Mesoporous Silica nanoparticles Enhances the Efficacy of Chemotherapy in Multidrug-Resistant Cancer Cells," vol. 5, No. 23, pp. 2673-2677 (2009).

Cho et al., "Targeted delivery of SiRNA-generating DNA nanocassettes using multifunctional nanoparticles," vol. 9, No. 11, pp. 1964-1973 (2013).

Communication of European publication number and information on the application of Article 67(3) EPC for European Application No. 14860910.0 (Aug. 18, 2016).

Dekrafft et al., "Iodinated nanoscale coordination polymers as potential contrast agents for computed tomography," Angew Chem Int Ed., vol. 48, pp. 9901-9904 (2009).

Dinca et al., "Hydrogen Storage in Microporous Metal-Organic Frameworks with Exposed Metal Sites," Angew Chem Int Edit 47, p. 6766-6779 (2008).

Extended European Search Report corresponding to Application No. 12810577.2 dated Feb. 4, 2015.

Fire et al., "Potent and specific genetic interference by double-stranded RNA in Caenorhabditis elegans," Nature, vol. 391, p. 806-811 (Feb. 1998).

Foged, "siRNA Delivery with Lipid-based Systems:Promises and Pitfalls," Curr Top Med Chem, vol. 12, p. 97-107 (2012).

Giger et al. "Gene delivery with bisphosphonate-stabilized calciun1 phosphate nanoparticles," Journal of Controlled Release. vol. 150 pp. 87-93 (2011).

Giraudo et al. "An amino-bisphosphonate targets MMP-9-expressing macrophages and angiogenesis to impair cervical carcinogenesis," The Journal of Clinical Investigation. vol. 114, No. 5 pp. 623-633 (2004).

Giustini et al., "Microstructure and Dynamics of the Water-in-Oil CTAB/n-Pentanol/n-Hexane/Water Microemulsion: A Spectroscopic and Conductivity Study," Journal of Physical Chemistry. vol. 100, No. 8 pp. 3190-3198 (1996).

Graf et al., "A General Method for the Controlled Embedding of Nanoparticles in Silica Colloids," Langmuir. vol. 22, No. 13 pp. 5604-5610 (2006).

Graf et al., "A General Method to Coat Colloidal Particles with Silica," Langmuir. vol. 19, No. 17 pp. 6693-6700 (2003).

Hafeman et al. "Evaluation of liposomal clodronate for treatment of malignant histiocytosis in dogs," Cancer Immunol. Immunother. vol. 59 pp. 441-452 (2010).

(56) References Cited

OTHER PUBLICATIONS

He et al., Nanoscale Metal-Organic Frameworks for the Co-Delivery of Cisplatin and Pooled siRNAs to Enhance Therapeutic Effcacy in Drug-Resistant Ovarian Cancer Cells, J. Am. Chem. Soc., vol. 136, p. 5181-5184 (2014).
Horcajada et al., "Porous metal-organic-framework nanoscale carriers as a potential platform for drug delivery and imaging," Nat Mater 9, p. 172-178 (2010).
Jin et al., "Targeting-triggered porphysome nanostructure disruption for activatable photodynamic therapy," Adv. Healthcare Mater., vol. 3, No. 8 pp. 1240-1249 (2014).
Kalayda et al., "Synthesis, Structure and Biological Activity of New Azine-Bridged Dnuclear Platinum(II) Complexes," Eur. J. Inorg. Chem. pp. 4347-4355 (2003).
Kelland, "The resurgence of platinum-based cancer chemotherapy,". Nature Reviews Cancer , 7, 573-584 (2007).
Kitabwalla et al., "RNA interference—a new weapon against HIV and beyond," The New England Journal of Medicine, vol. 347, No. 17, pp. 1364-1367 (Oct. 24, 2002).
Liu et al., "Self-assembled nanoscale coordination polymers with trigger release properties for effective anticancer therapy," Nature Communications, vol. 5, 4128, p. 1-25 (2014).
Lovell et al., "Porphysome nanovesicles generated by porphyrin bilayers for use as multimodal biophotonic contrast agents," Nat. Mater., vol. 10 pp. 324-332 (2011).
Lee et al., "Metal-organic framework materials as catalysts," Chem Soc Rev, 38, 1450-1459 (2009).
Leigh, "Comprehensive Coordination Chemistry II From Biology to Nanotechnology," Journal of Organometallic Chemistry. vol. 689, No. 16 pp. 2733-2742 (2004).
Letter regarding an Office Action corresponding to Japanese Patent Application No. 2014-520238 dated Mar. 14, 2016.
Letter regarding decision to grant a Japanese Patent corresponding to Japanese Patent Application No. 2014-520238 dated Oct. 31, 2016.
Li et al., "Design and synthesis of an exceptionally stable and highly porous metal-organic framework," Nature 402, p. 276-279 (1999).
Liu et al., "Phosphorescent nanoscale coordination polymers as contrast agents for optical imaging," Angew Chem Int Edit, 50, p. 3696-3700 (2011).
Liu et al., "Coercing bisphosphonates to kill cancer cells with nanoscale coordination polymerst," Chem. Commun. vol. 48 pp. 2668-2670 (2012).
Lowery et al., "Cost-effectiveness of early palliative care intervention in recurrent platinum-resistant ovarian cancer," Gynecol Oncol 2013, 130, p. 426-430 (2013).
Mack et al., "The effects of terbium on the cellular accumulation of cisplatin in MDA-MB-231 human breast tumor cells," Cancer Chemotherapy and Pharmacology. vol. 39 pp. 217-222 (1997).
Matsumura, Y., and Maeda, H., "A New Concept for Macromolecular Therapeutics in Cancer Chemotherapy: Mechanism of Tumoritropic Accumulation of Proteins and the Antitumor Agent Smancs," Cancer Research. vol. 46 pp. 6387-6392 (1986).
Meng, H.; Liong, M.; Xia, T.; Li, Z.; Ji, Z.; Zink, J. I.; Nel, A. E. ACS nano 4, p. 4539-4550 (2010).
Mukhopadhyay et al., "Conjugated Platinum (IV)—Peptide Complexes for Targeting Angiogenic Tumor Vasculature," Bioconjugate Chemistry. vol. 19, No. 1 pp. 39-49 (2008).
Notification Concerning Transmittal of International Preliminary Report on Patentability (Chapter I of the Patent CooperationTreaty) corresponding to International Patent Application No. PCT/US2012/045954 dated Jan. 23, 2014.
Notification of Transmittal of the International Search Report and the Written Opinion of the International Searching Authority, or the Declaration corresponding to International Application No. PCT/US2012/045954 dated Jan. 28, 2013.
Notification of Transmittal of the International Search Report and the Written Opinion of the International Searching Authority, or the Declaration corresponding to International Application No. PCT/US14/64388 dated Feb. 28, 2015.
Notification Concerning Transmittal of International Preliminary Report on Patentability (Chapter I of the Patent CooperationTreaty) corresponding to International Patent Application No. PCT/US2014/064388 dated May 19, 2016.
Notice of allowance and Fee(s) Due, Examiner-Initiated Interview Summary, and Notice of Allowability Corresponding to U.S. Appl. No. 14/131,575 dated Feb. 27, 2017.
Office Action corresponding to U.S. Appl. No. 14/131,575 dated Aug. 12, 2016.
Official Action corresponding to U.S. Appl. No. 14/131,575 dated Dec. 16, 2016.
Official Action corresponding to European Patent Application Serial No. 12810577.2 dated Jan. 5, 2017.
Restriction Requirement corresponding to U.S. Appl. No. 14/131,575 dated Nov. 20, 2015.
Rieter et al., "Nanoscale metal-organic frameworks as potential multimodal contrast enhancing agents," J Am Chem Soc, 128, 9024-9025, pp. 1-7 (2006).
Rieter et al., "Nanoscale Coordination Polymers for Platinum-Based Anticancer Drug Delivery," Journal of the American Chemical Society. vol. 130 pp. 11584-11585 (2008).
Roberts, et al., "Identification of genes associated with platinum drug sensitivity and resistance in human ovarian cancer cells," Brit J Cancer , vol. 92, pp. 1149-1158 (2005).
Rosi, et al., "Rod Packings and Metal-Organic Frameworks Constructed from Rod-Shaped Sedcondary Building Units," J Am Chem Soc, vol. 127, pp. 1504-1518 (2005).
Salzano et al. "Self-assembly nanoparticles for the delivery of bisphosphonates into tumors," International Journal of Pharmaceutics 403 pp. 292-297 (2011).
Schaate et al., "Modulated synthesis of Zr-Based metal-organic frameworks: from nano to single crystals," Chem-Eur J, 17, p. 6643-6651 (2011).
Shahzad et al., "Novel strategies for reversing platinum resistance," Drug Resist Updates 12, p. 148-152 (2009).
Sheats, "History of Organometallic Polymers," Journal of Macromolecular Science: Part A—Chemistry. vol. 15, No. 6 pp. 1173-1199 (1981).
Shi et al., "In-vitro osteogenesis of synovium stem cells induced by controlled release of bisphosphate additives from microspherical meso porous silica composite," Biomaterials. vol. 30, No. 23-24, pp. 3996-4005 (2009).
Shmeeda et al. "Delivery of zoledronic acid encapsulated in folate-targeted liposome results in potent in vitro cytotoxic activity on tumor cells," Journal of Controlled Release 146 pp. 76-83 (2010).
"Small Interfering RNA," pp. 1-6, downloaded from https://en.wikipedia.org/wiki/Small_interfering_RNA on Nov. 11, 2016.
Taylor-Parshow et al., "Post-synthetic modification of iron-carboxylate nanoscale metal-organic frameworks for imaging and drug delivery," Journal of the American Chemical Society 131, 14261-14263, pp. 1-10 (2009).
Uemura, T., and Kitagawa, S., "Prussian Blue Nanoparticles Protected by Poly(vinylpyrrolidone)," Journal of the American Chemical Society. vol. 125, No. 26 pp. 7814-7815 (2003).
Vaucher et al., "Synthesis of Prussian Blue Nanoparticles and Nanocrystal Superlattices in Reverse Microemulsions," Angew. Chem. Int. Ed. vol. 39, No. 10 pp. 1793-1796 (2000).
Vaucher et al., "Molecule-Based Magnetic Nanoparticles: Synthesis of Cobalt Hexacyanoferrate, Cobalt Pentacyanonitrosylferrate, and Chromium Hexacyanochromate Coordination Polymers in Water-in-Oil Microemulsions," Nano Letters. vol. 2, No. 3 pp. 225-229 (2002).
Vaughan, et al., "Rethinking ovarian cancer: recommendations for improving outcomes," Nat Rev Cancer , 11, 719-725, pp. 1-19 (2011).
Wang et al., "Postsynthetic modification of metal-organic frameworks," Chem Soc Rev 38, p. 1315-1329 (2009).
White et al., "Photooxidation of Diglycine in Confined Media. Application of the Microreactor Model for Spin-Correlated Radical Pairs in Reverse Micelles and Water-in-Oil Microemulsions," Langmuir. vol. 21, No. 7 pp. 2721-2727 (2005).
Wong et al., "Fluorescence Probing of Inverted Micelles. The State of Solublized Water Clusters in Alkane/Diisooctyl Sulfosuccinate

(56) References Cited

OTHER PUBLICATIONS (Aerosol OT) Solution," Journal of the American Chemical Society. vol. 98, No. 9 pp. 2391-2397 (1976).

Xiong et al., "Traceable multifunctional micellar nanocarriers for cancer-targeted co-delivery of MDR-1 siRNA and doxorubicin," ACS nano, vol. 5, No. 6, p. 5202-5213 (2011).

Xu, W., and Akins, D.L., "Reverse micellar synthesis of CdS nanoparticles and self-assembly into a superlattice," Materials Letters. vol. 58 pp. 2623-2626 (2004).

Yamada et al., "Synthesis and Isolation of Cobalt Hexacyanoferrate/Chromate Metal Coordination Nanopolymers Stabilized by Alkylamino Ligand with Metal Elemental Control," Journal of the American Chemical Society. vol. 126 pp. 9482-9483 (2004).

Yellepeddi et al., "Comparative evaluation of small-molecule chemosensitizers in reversal of cisplatin resistance in ovarian cancer cell," Anticancer Res 32, p. 3651-3658 (2012).

Yu et al., "Immobilization of polymer-stabilized metal colloids by a modified coordination capture: preparation of supported metal colloids with singular catalytic properties," Journal of Molecular Catalysis A: Chemical. vol. 142 pp. 201-211 (1999).

Zhang et al., "Three-Dimensional Lanthanoid-Containing Coordination Frameworks: Structure, Magnetic and Fluorescent Properties," European Journal of Inorganic Chemistry. pp. 766-772 (2005).

Zhang et al., "Antibody-linked spherical nucleic acids for cellular targeting," Journal of the American Chemical Society, 134, 16488-16491, pp. 1-11 (2012).

Zou, et al., "Enhanced apoptosis of ovarian cancer cells via nanocarrier-mediated codelivery of siRNA and doxorubicin," Int J Nanomed, 7, pp. 3823-3835 (2012).

Office Action corresponding to U.S. Appl. No. 15/034,799 dated Sep. 21, 2017.

Chinese Search Report corresponding to Chinese Patent Application No. 2014800722580 dated Jun. 15, 2018.

Advisory Action corresponding to U.S. Appl. No. 15/034,799 dated Jun. 5, 2018.

Office Action corresponding to U.S. Appl. No. 15/034,799 dated Mar. 22, 2018.

Communication of the Extended European Search Report corresponding to European Application No. 14860910.0 dated Jun. 20, 2017.

Cunha et al., "Rationalization of the entrapping of the bioactive molecules into a series of functionalized porous zirconium terephthalate MOFs," J. Mater, Chem., vol. 1, pp. 1101-1108 (2013).

Huxford-Phillips et al., "Lipid-coated nanoscale coordination polymers for targeted cisplatin delivery," RSC Advances, vol. 3, No. 34, pp. 14438-14443 (Jan. 2013).

European Decision to Grant corresponding to European Patent Application Serial No. 12810577.2 dated Jan. 7, 2019.

Office Action corresponding to European Patent Application Serial No. 14860910.0 dated Jan. 29, 2019.

Office Action corresponding to Japanese Patent Application No. 2016-528894 dated Feb. 4, 2019.

Communication of European publication number and information on the application of Article 67(3) EPC for European Application No. 19151591.5 dated May 15, 2019.

Extended European Search Report corresponding to European Application No. 19151591.5 dated May 13, 2019.

Notice of Allowance and Interview Summary corresponding to U.S. Appl. No. 15/034,799 dated Jun. 14, 2019.

Office Action corresponding to U.S. Appl. No. 15/034,799 dated Mar. 20, 2019.

Office Action corresponding to Chinese Patent Application No. 2014800722580 dated Mar. 20, 2019.

European Intention to Grant for European Patent Application Serial No. 12810577.2 dated Sep. 17, 2018.

Interview Summary corresponding to U.S. Appl. No. 15/034,799 dated Jul. 5, 2018.

Office Action corresponding to Japanese Patent Application No. 2016-528894 dated Jul. 17, 2018.

Office Action corresponding to Chinese Patent Application No. 2014800722580 dated Jun. 27, 2018.

Office Action corresponding to U.S. Appl. No. 15/034,799 dated Sep. 21, 2018.

Decision to Grant corresponding to Japanese Patent Application No. 2016-528894 dated Aug. 19, 2019.

He et al., Nanoscale Coordination Polymers Codeliver Chemotherapeutics and siRNAs to Eradicate Tumors of Cisplatin-Resistant Ovarian Cancer, JACS, vol. 138, pp. 6010-6019 (2016).

Office Action corresponding to Chinese Patent Application No. 2014800722580 dated Nov. 11, 2019.

* cited by examiner

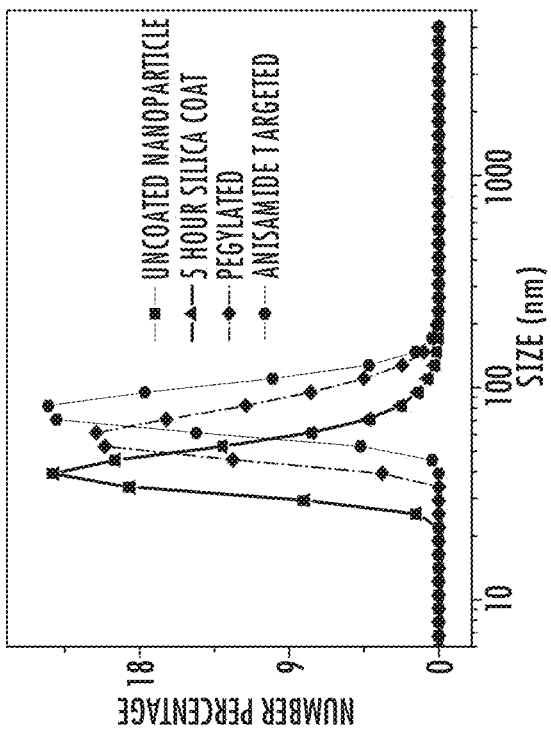
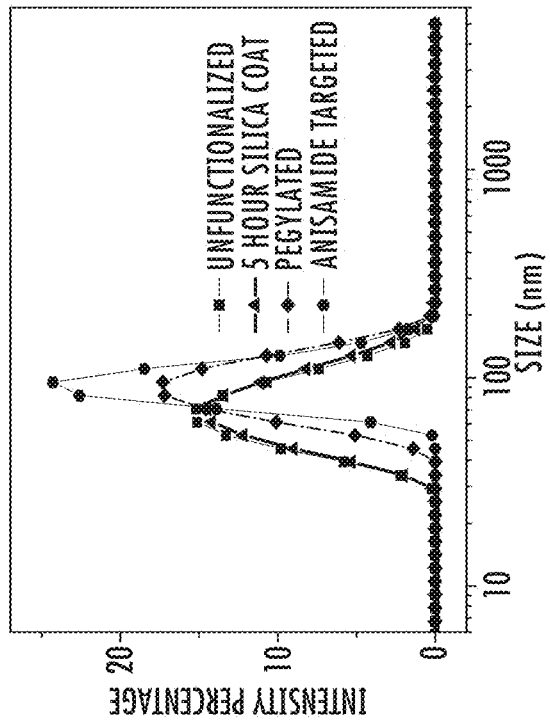

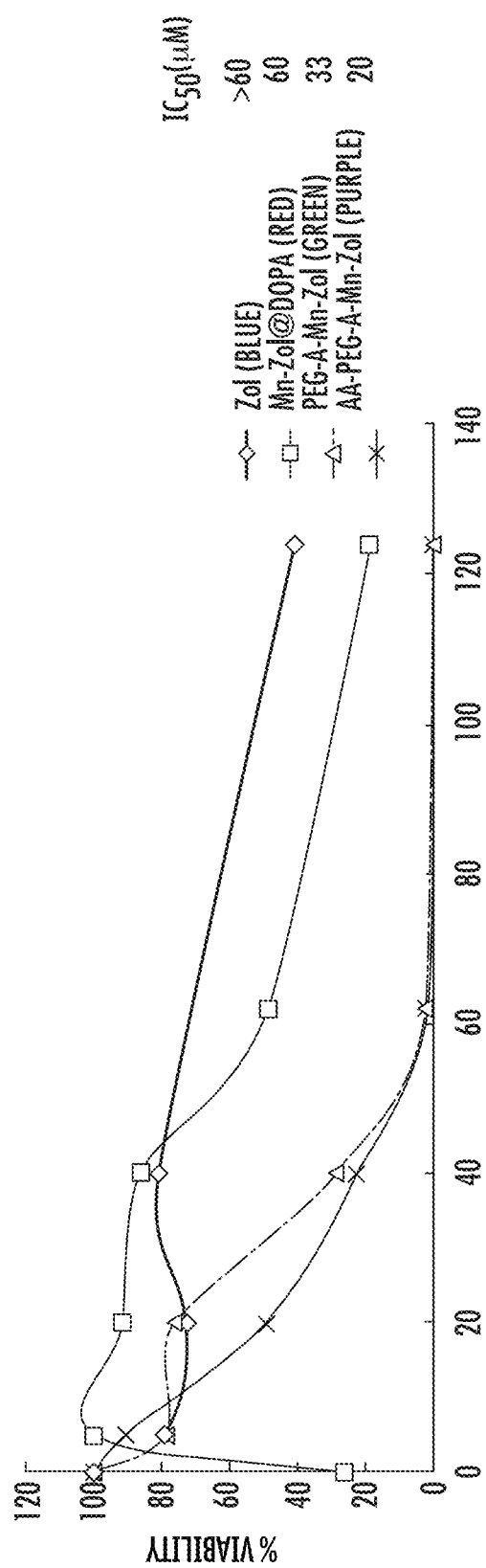
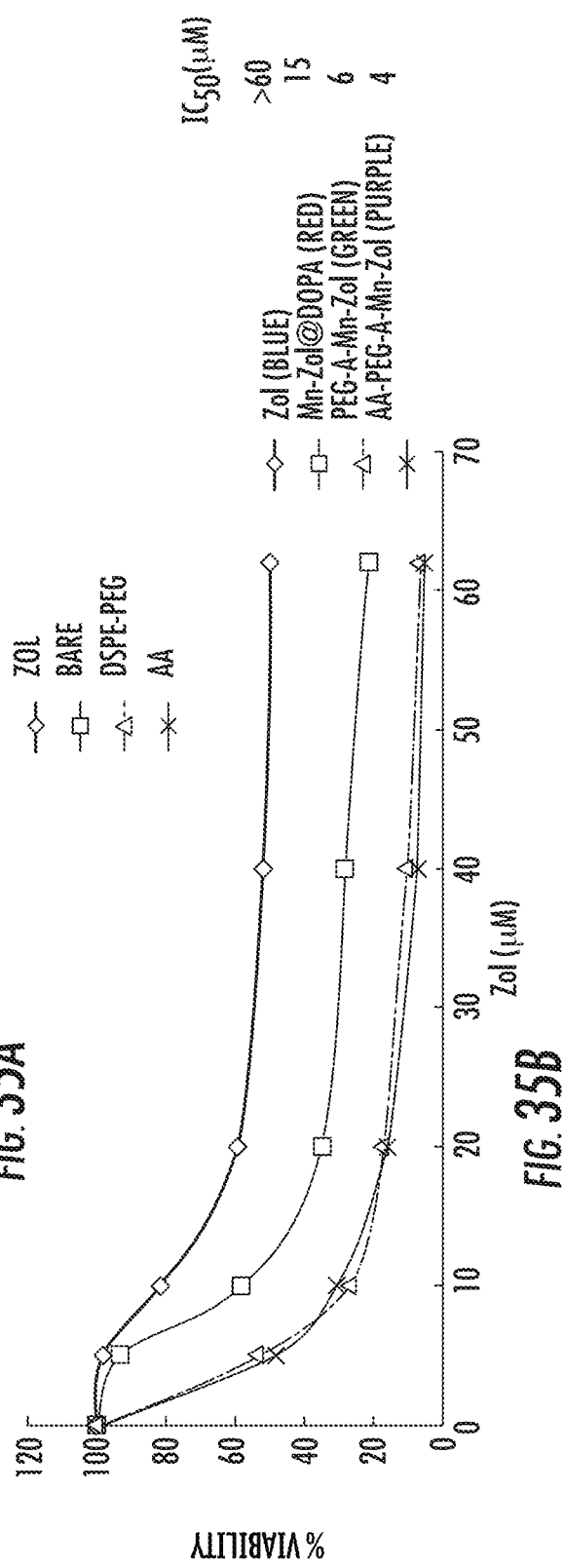
FIG. 35A
FIG. 35B

METAL BISPHOSPHONATE NANOPARTICLES FOR ANTI-CANCER THERAPY AND IMAGING AND FOR TREATING BONE DISORDERS

RELATED APPLICATIONS

This application is a continuation of U.S. patent application Ser. No. 14/131,575, filed on Mar. 7, 2014, which is a national stage application of International Application No. PCT/US2012/045954, filed on Jul. 9, 2012, which claims priority to U.S. Provisional Application Ser. No. 61/505,806, filed Jul. 8, 2011; the disclosures of each of which are incorporated herein by reference in their entireties.

GOVERNMENT INTEREST

This invention was made with government support under Grant No. CA151455 awarded by the National Institutes of Health and Grant No. DMR-0906662 awarded by the National Science Foundation. The government has certain rights in the invention.

TECHNICAL FIELD

The presently disclosed subject matter relates to metal-bisphosphonate nanoparticles, compositions comprising the nanoparticles, methods of synthesizing the nanoparticles, and their use as therapeutic agents for treating cancer or bone-related disorders and/or as imaging agents. The nanoparticles can be coated with organic or inorganic polymers, single lipid layers, and/or lipid bilayers, and/or incorporated into liposomes. The nanoparticles can further include additional therapeutic agents and/or targeting agents to direct the nanoparticles to specific sites for use in disease diagnosis, treatment, and/or imaging.

ABBREVIATIONS

° C.=degrees Celsius
%=percentage
µM=micromolar
AA=anisamide
BP=bisphosphonate
Ca=calcium
Ca-Pam=calcium pamidronate
Ca-Zol=calcium zoledronate
cisPt=cisplatin
DACH=R,R-diaminocyclohexane
DLS=dynamic light scattering
DMF=dimethylformamide
DMSO=dimethylsulfoxide
DOPA=1,2-dioleoyl-sn-glycero-3-phosphate sodium salt
DOPC=1,2-dioleoyl-sn-glycero-3-phosphocholine
DOPE=dioleoyl L-α-phosphatidylethanol amine
DOTAP=1,2-dioleoyl-3-trimethylammonium propane
DSPE-PEG$_{2k}$=1,2-distearoyl-sn-glycero-3-phosphoethanolamine-N-[amino(polyethylene glycol)2000]
EDS=energy dispersive X-ray spectroscopy
EtOH=ethanol
g=gram
h=hour
IC$_{50}$=fifty percent inhibitory concentration
ICP-MS=inductively coupled plasma-mass spectrometry
kg=kilogram
mg=milligram
min=minute
mL=milliliter
mM=millimolar
mmol=millimole
Mn=manganese
Mn-Zol=manganese zoledronate
MRI=magnetic resonance imaging
nm=nanometer
NMR=nuclear magnetic resonance
MW=molecular weight
Pam=pamidronate
PBS=phosphate buffered saline
PDI=polydispersity index
PEG=polyethylene glycol
PET=positron emission tomography
PVP=polyvinylpyrrolidone
r=radius
RES=reticuloendothelial system
RGD=arginine-glycine-aspartic acid
rpm=revolutions-per-minute
SEM=scanning electron microscopy
siRNA=small interfering ribonucleic acid
SPECT=single photon emission computed tomography
TEM=transmission electron microscopy
TGA=thermogravimetric analysis
W=watts
Zn=zinc
Zol=zoledronate

BACKGROUND

Many anticancer drugs are currently available for treating various types of cancers in the clinic, but their therapeutic efficacy has been limited by the inability to selectively deliver these drugs to the tumors. Most, if not all, of these anticancer drugs are highly cytotoxic and can kill normal cells along with the cancerous cells. Because of the lack of methods to deliver these anticancer drugs to the tumor regions, a high dose of these drugs is often needed, which can cause undesirable side effects. As a result, most of the currently used anticancer drugs have a rather limited therapeutic index. Such a limit on the dosage prevents the complete eradication of all the cancer cells in a patient, and can lead to the recurrence of the cancer in many patients. The limit in dosage can also predispose the recurring cancer to drug resistance and thus worsens the prognosis of the patient. There is therefore a great need for new anticancer compositions that can be selectively delivered to the tumors and provide superior therapeutic indices. There is also a need for real-time techniques for directly monitoring how efficiently the anticancer drugs are localized in tumors after their administration.

Bisphosphonates, such as those shown below in Scheme 1, have been used to treat bone resorption-related diseases, such as osteoporosis. Recently, bisphosphonates (in particular, zoledronic acid and pamidronate) have been used to treat bone metastases of several cancers such as breast cancer. There is also increasing evidence that bisphosphonates can be effective antitumor agents by blocking metalloproteinase and other important protein pathways. However, the clinical application of bisphosphonates as anticancer therapeutics is limited by their unfavorable pharmacokinetics as the majority of the injected phosphonates either bind to the bones or are quickly cleared via kidney filtration. Accordingly, there is a need for additional methods of delivering bisphosphonates as therapeutic agents, such as for treating cancer and bone-related disorders.

SUMMARY

In some embodiments, the presently disclosed subject matter provides a method of preparing a metal-bisphosphonate nanoparticle, the method comprising: providing a solution comprising a bisphosphonate and a multivalent metal ion; aging the solution comprising the bisphosphonate and the multivalent metal ion for a period of time to provide an aged solution; and isolating a metal-bisphosphonate nanoparticle from the aged solution.

In some embodiments, the multivalent metal ion is divalent. In some embodiments, the multivalent metal ion is selected from the group consisting of $Ca^{2+}$, $Mg^{2+}$, $Mn^{2+}$, $Zn^{2+}$, and combinations thereof.

In some embodiments, the solution comprising the bisphosphonate and the multivalent metal ion comprises at least two different multivalent metal ions and/or comprises at least one paramagnetic multivalent metal ion. In some embodiments, the solution comprising the bisphosphonate and the multivalent metal ion is free of paramagnetic metal ions, phosphate ions, and/or platinum metal ions.

In some embodiments, the bisphosphonate has a structure of Formula (I):

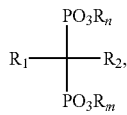

wherein: n and m are each independently an integer between 0 and 2; each R is independently selected from the group consisting of H, alkyl, substituted alkyl, aralkyl, aryl, and substituted aryl; $R_1$ is selected from the group consisting of H, hydroxyl, halo, alkyl, substituted alkyl, amino, alkoxy, and alkylthio; and $R_2$ is selected from the group consisting of halo, alkyl, substituted alkyl, aralkyl, substituted aralkyl, alkoxy, alkylthio, aryloxy, arylthio and arylamino; or a salt thereof. In some embodiments, $R_2$ is selected from substituted alkyl and aralkyl, wherein substituted alkyl is selected from $NH_2$-substituted alkyl, alkylamino-substituted alkyl, and dialkylamino-substituted alkyl and wherein aralkyl is an aralkyl group comprising a nitrogen-containing heteroaryl moiety.

In some embodiments, the bisphosphonate is selected from the group consisting of zoledronic acid, pamidronate, risedronic acid, alendronate, zeridronic acid, tiludronate, etidronate, and ibandronate.

In some embodiments, providing a solution of a bisphosphonate and a multivalent metal ion comprises one of: (a) dissolving the bisphosphonate and a multivalent metal ion precursor in a solvent, wherein the multivalent metal ion precursor is a compound of the formula $ML_x$, wherein x is an integer corresponding to the valency of the metal ion, M is a multivalent metal ion, and each L is independently a ligand selected from the group consisting of halo, hydroxyl, sulfate, and amino, or a hydrate or other solvate thereof; and (b) mixing a precursor solution of the bisphosphonate with a precursor solution comprising the multivalent metal ion, wherein the precursor solution comprising the multivalent metal ion is prepared by dissolving a compound of the formula $ML_x$ as described in (a) or a hydrate or other solvate thereof in a solvent. In some embodiments, providing the solution comprising the bisphosphonate and the multivalent metal ion further comprises adjusting the pH of the solution comprising the bisphosphonate and the multivalent metal ion or adjusting the pH of a precursor solution thereof.

In some embodiments, providing the solution comprising the bisphosphonate and the multivalent metal ion further comprises adding one or more non-bisphosphonate therapeutic agent or prodrug thereof and/or one or more imaging agent to the solution comprising the bisphosphonate and the multivalent metal ion or a precursor solution thereof. In some embodiments, the non-bisphosphonate therapeutic agent, prodrug thereof, and/or imaging agent comprises functional groups that can coordinate to the multivalent metal ion. In some embodiments, the non-bisphosphonate therapeutic agent, prodrug thereof, and/or imaging agent is selected from the group consisting of chemotherapeutics, photodynamic therapy agents, radiosensitizers, beta-emitting radionuclides, proteins, peptides, small interfering RNA (siRNA), and fluorophores.

In some embodiments, the method further comprises subjecting the solution comprising the bisphosphonate and the multivalent metal ion to microwaves prior to aging. In some embodiments, the aging comprises heating the solution comprising the bisphosphonate and the multivalent metal ion to a temperature above room temperature for a period of time. In some embodiments, the temperature above room temperature is between about 80° C. and about 140° C. In some embodiments, the period of time is between about 20 minutes and about 24 hours.

In some embodiments, isolating a metal-bisphosphonate nanoparticle comprises one or more of the group consisting of centrifuging the aged solution to provide a crude nanoparticle; filtering the aged solution to provide a crude nanoparticle; re-dispersing a crude nanoparticle in an alcohol; washing a crude nanoparticle with an aqueous solution; washing a crude nanoparticle with an alcoholic solution; dialyzing the particles using filters with certain molecular weight cut-offs; and drying a crude nanoparticle. In some embodiments, isolating a metal-bisphosphonate nanoparticle comprises isolating a crystalline metal-bisphosphonate nanoparticle.

In some embodiments, the method further comprises contacting an isolated metal-bisphosphonate nanoparticle with one or more coating agents or layers, thereby providing a coated metal-bisphosphonate nanoparticle. In some embodiments, the one or more coating agents or layers are selected from the group consisting of a metal oxide, a polymer (e.g., a silica-based polymer (e.g., silica ($SiO_2$), a poly(siloxane), or a poly(silsesquioxane)) or an organic polymer), a single lipid layer, a lipid bilayer, and combinations thereof.

In some embodiments, the one or more coating agent or layer comprises an organic polymer, wherein said organic polymer is a hydrophilic polymer. In some embodiments, the one or more coating agent or layer comprises a targeting moiety and/or a passivating moiety. In some embodiments, the one or more coating agent or layer is selected from the group consisting of dioleoyl L-α-phosphatidylethanolamine (DOPE), 1,2-dioleoyl-3-trimethylammonium propane (DOTAP), anisamide-derivatized DOPE, silica, cRGfK-derivatized silica, polyethylene glycol (PEG)-derivatized silica, and anisamide-PEG-derivatized silica.

In some embodiments, the presently disclosed subject matter provides a metal-bisphosphonate nanoparticle prepared according to a method comprising: providing a solution comprising a bisphosphonate and a multivalent metal ion; aging the solution comprising the bisphosphonate and the multivalent metal ion for a period of time to provide an aged solution; and isolating a metal-bisphosphonate nanoparticle from the aged solution.

In some embodiments, the presently disclosed subject matter provides a pharmaceutical composition comprising a pharmaceutically acceptable carrier and a metal-bisphosphonate nanoparticle prepared according to a method comprising: providing a solution comprising a bisphosphonate and a multivalent metal ion; aging the solution comprising the bisphosphonate and the multivalent metal ion for a period of time to provide an aged solution; and isolating a metal-bisphosphonate nanoparticle from the aged solution.

In some embodiments, the presently disclosed subject matter provides a method of treating a cancer or a bone-related disorder in a subject in need of treatment thereof, wherein the method comprises administering to the subject an effective amount of a metal-bisphosphonate nanoparticle prepared according to a method comprising: providing a solution comprising a bisphosphonate and a multivalent metal ion; aging the solution comprising the bisphosphonate and the multivalent metal ion for a period of time to provide an aged solution; and isolating a metal-bisphosphonate nanoparticle from the aged solution. In some embodiments, the cancer is selected from the group consisting of lung cancer, breast cancer, and prostate cancer.

In some embodiments, the method of treating a cancer or a bone-related disorder further comprises rendering an image of one of a cell, a tissue, an organ or a subject following the administration of the metal-bisphosphonate nanoparticle. In some embodiments, rendering an image comprises performing one of the group consisting of magnetic resonance imaging (MRI), optical imaging, positron emission tomography (PET), and single photon emission computed tomography (SPECT).

In some embodiments, the presently disclosed subject matter provides a metal-bisphosphonate nanoparticle, wherein the metal-bisphosphonate nanoparticle comprises a core comprising a crystalline multivalent metal ion-bisphosphonate complex. In some embodiments, the nanoparticle further comprises one or more coating agents or layers surrounding least a portion of an outer surface of the core. In some embodiments, the one or more coating agents or layers are selected from the group consisting of a metal oxide, a polymer (e.g., a silica-based polymer (e.g., silica (SiO₂), a poly(siloxane), or a poly(silsesquioxane)), or an organic polymer), a single lipid layer, a lipid bilayer, and combinations thereof.

In some embodiments, one or more of the coating agents or layers is derivatized with a targeting agent and/or a passivating agent. In some embodiments, each of the one or more coating agents or layers is selected from the group consisting of dioleoyl L-α-phosphatidylethanolamine (DOPE), 1,2-dioleoyl-3-trimethylammonium propane (DOTAP), anisamide-derivatized DOPE, silica, cRGfK-derivatized silica, polyethylene glycol (PEG)-derivatized silica, and anisamide-PEG-derivatized silica.

In some embodiments, the nanoparticle further comprises a non-bisphosphonate therapeutic agent or prodrug thereof and/or an imaging agent.

In some embodiments, the multivalent metal ion is a divalent metal ion. In some embodiments, the multivalent metal ion is selected from the group consisting of Ca²⁺, Mg²⁺, Mn²⁺, Zn²⁺, and combinations thereof.

In some embodiments, the bisphosphonate has a structure of Formula (I):

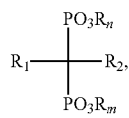

wherein: n and m are each independently an integer between 0 and 2; each R is independently selected from the group consisting of H, alkyl, substituted alkyl, aralkyl, aryl, and substituted aryl; R₁ is selected from the group consisting of H, hydroxyl, halo, alkyl, substituted alkyl, amino, alkoxy, and alkylthio; and R₂ is selected from the group consisting of halo, alkyl, substituted alkyl, aralkyl, substituted aralkyl, alkoxy, alkylthio, aryloxy, arylthio and arylamino; or a salt thereof. In some embodiments, the bisphosphonate is selected from the group consisting of zoledronic acid, pamidronate, risedronic acid, alendronate, zeridronic acid, tiludronate, etidronate, and ibandronate.

In some embodiments, the presently disclosed subject matter provides a pharmaceutical composition comprising a pharmaceutically acceptable carrier and a metal-bisphosphonate nanoparticle comprising a core comprising a crystalline multivalent metal ion-bisphosphonate complex.

In some embodiments, the presently disclosed subject matter provides a method of treating a cancer or a bone-related disorder in a subject in need of treatment thereof, wherein the method comprises administering to the subject an effective amount of a metal-bisphosphonate nanoparticle, wherein the metal-bisphosphonate nanoparticle comprises a core comprising a crystalline multivalent metal ion-bisphosphonate complex.

In some embodiments, the presently disclosed subject matter provides a metal-bisphosphonate nanoparticle comprising: (a) a core comprising a multivalent metal ion-bisphosphonate complex; and (b) a coating layer surrounding at least a portion of an outer surface of the core, wherein the coating layer comprises a metal oxide, a polymer (e.g., a silica-based polymer, or an organic polymer), a single lipid layer, or a lipid bilayer. In some embodiments, the core further comprises a non-bisphosphonate therapeutic agent or prodrug thereof and/or an imaging agent.

In some embodiments, the multivalent metal ion is a divalent metal ion. In some embodiments, multivalent metal ion is selected from the group consisting of Ca²⁺, Mg²⁺, Mn²⁺, Zn²⁺, and combinations thereof. In some embodiments, the bisphosphonate has a structure of Formula (I):

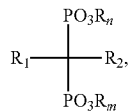

wherein: n and m are each independently an integer between 0 and 2; each R is independently selected from the group consisting of H, alkyl, substituted alkyl, aralkyl, aryl, and substituted aryl; R₁ is selected from the group consisting of H, hydroxyl, halo, alkyl, substituted alkyl, amino, alkoxy, and alkylthio; and R₂ is selected from the group consisting of halo, alkyl, substituted alkyl, aralkyl, substituted aralkyl, alkoxy, alkylthio, aryloxy, arylthio and arylamino; or a salt thereof. In some embodiments, the bisphosphonate is selected from the group consisting of zoledronic acid, pamidronate, risedronic acid, alendronate, zeridronic acid, tiludronate, etidronate, and ibandronate.

In some embodiments, the coating layer comprises a silica-based polymer, wherein said silica-based polymer is derivatized with a targeting agent and/or a passivating agent. In some embodiments, the coating layer comprises silica, cRGfK-derivatized silica, polyethylene glycol (PEG)-derivatized silica, and/or anisamide-PEG-derivatized silica.

In some embodiments, the nanoparticle further comprises one or more additional coating layer in addition to the metal oxide, polymer, single lipid layer, or lipid bilayer coating layer, wherein said one or more additional coating layer comprises a material selected from a metal oxide, a polymer (e.g., an organic polymer, or a silica-based polymer), a single lipid layer, a lipid bilayer, and combinations thereof. In some embodiments, the presently disclosed subject matter provides a pharmaceutical composition comprising a pharmaceutically acceptable carrier and a metal-bisphosphonate nanoparticle comprising: (a) a core comprising a multivalent metal ion-bisphosphonate complex; and (b) a coating layer surrounding at least a portion of an outer surface of the core, wherein the coating layer comprises a metal oxide, a polymer, a single lipid layer, or a lipid bilayer.

In some embodiments, the presently disclosed subject matter provides a method of treating a cancer or bone-related disorder in a subject in need of treatment thereof, wherein the method comprises administering to said subject an effective amount of a metal-bisphosphonate nanoparticle comprising: (a) a core comprising a multivalent metal ion-bisphosphonate complex; and (b) a coating layer surrounding at least a portion of an outer surface of the core, wherein the coating layer comprises a metal oxide, a polymer, single lipid layer, or a lipid bilayer.

In some embodiments, the presently disclosed subject matter provides a metal-bisphosphonate nanoparticle comprising a core comprising: (a) $M_1$ wherein $M_1$ is a multivalent metal ion; and (b) a bisphosphonate, wherein the bisphosphonate comprises a metal complex having the formula $M_2L_x$, wherein x is an integer of 2 or greater, $M_2$ is a second metal ion, each L is a metal ion ligand, and wherein at least two L comprise a phosphonate group. In some embodiments, $M_1$ is a divalent metal ion.

In some embodiments, the bisphosphonate is a metal complex of the formula $M_2L_x$, wherein $M_2$ is platinum and x is 5 or 6. In some embodiments, two L have the formula —O—C(=O)—NH—P(=O)(OR)$_2$, wherein each R is independently H, alkyl, substituted alkyl, aralkyl, aryl, substituted aryl or a negative charge. In some embodiments, each R is independently H, alkyl, or a negative charge.

In some embodiments, the nanoparticle further comprises one or more coating agents or layers surrounding at least a portion of an outer surface of the core. In some embodiments, the nanoparticle comprises at least lipid coating layer or agent. In some embodiments, the one or more coating agents or layers comprise a targeting moiety or a passivating moiety.

In some embodiments, the nanoparticle further comprises a non-bisphosphonate therapeutic agent or prodrug thereof and/or an imaging agent.

In some embodiments, the presently disclosed subject matter provides a pharmaceutical composition comprising a pharmaceutically acceptable carrier and a metal-bisphosphonate nanoparticle comprising a core comprising: (a) $M_1$, wherein $M_1$ is a multivalent metal ion; and (b) a bisphosphonate, wherein the bisphosphonate comprises a metal complex having the formula $M_2L_x$, wherein x is an integer of 2 or greater, $M_2$ is a second metal ion, each L is a metal ion ligand, and wherein at least two L comprise a phosphonate group. In some embodiments, the presently disclosed subject matter provide a method of treating a cancer or a bone-related disorder in a subject in need of treatment thereof, wherein the method comprises administering to the subject an effective amount of a metal-bisphosphonate nanoparticle, wherein the metal-bisphosphonate nanoparticle comprises (a) $M_1$, wherein $M_1$ is a multivalent metal ion; and (b) a bisphosphonate, wherein the bisphosphonate comprises a metal complex having the formula $M_2L_x$, wherein x is an integer of 2 or greater, $M_2$ is a second metal ion, each L is a metal ion ligand, and wherein at least two L comprise a phosphonate group.

Accordingly, it is an object of the presently disclosed subject matter to provide metal bisphosphonate nanoparticles and compositions comprising such nanoparticles, and methods of making and using the same.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIG. 21A is a graph of intensity-weighted dynamic light scattering (DLS) curves for unfunctionalized (squares), silica coated (triangles), pegylated (diamonds), and anisamide targeted (circles) amorphous calcium zoledronate nanoparticles.

FIG. 21B is a graph of number-weighted dynamic light scattering (DLS) curves for unfunctionalized (squares), silica coated (triangles), pegylated (diamonds), and anisamide targeted (circles) amorphous calcium zoledronate nanoparticles.

FIGS. 35A and 35B are graphs showing cytotoxicity assays of Mn-Zol@DOPA (squares), PEG-A-Zn-Zol (triangles), and AA-PEG-A-Mn-Zol particles (crosses) against ASPC-1 (FIG. 35A) and MCF-7 cells (FIG. 35B). In each of FIGS. 35A and 35B, Zol=diamonds.

DETAILED DESCRIPTION

Figure 1:
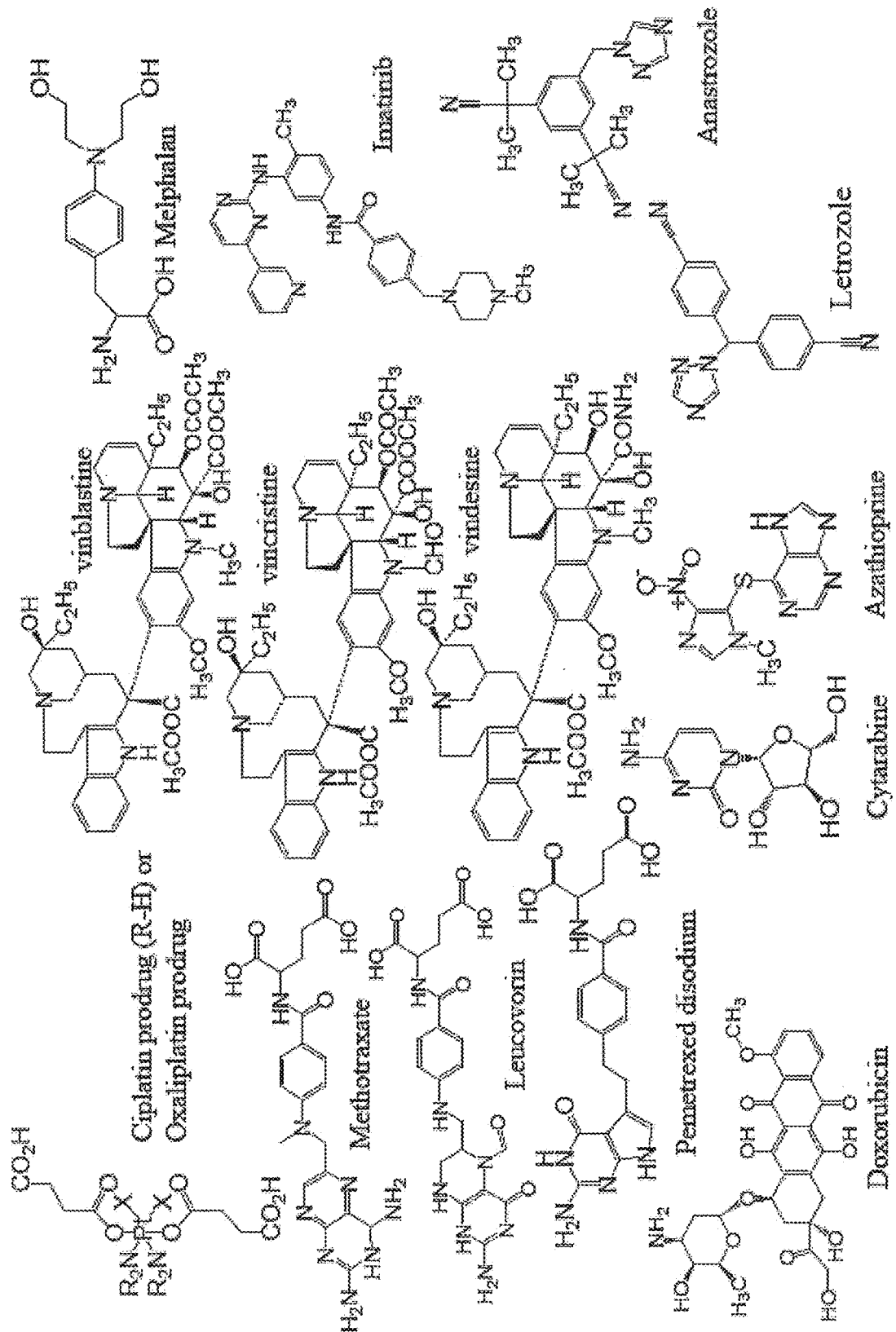
FIG. 1 is a schematic diagram showing the chemical structures of exemplary anticancer agents with functional groups that can coordinate with metal centers to form coordination polymer nanoparticles.
Figure 2A:
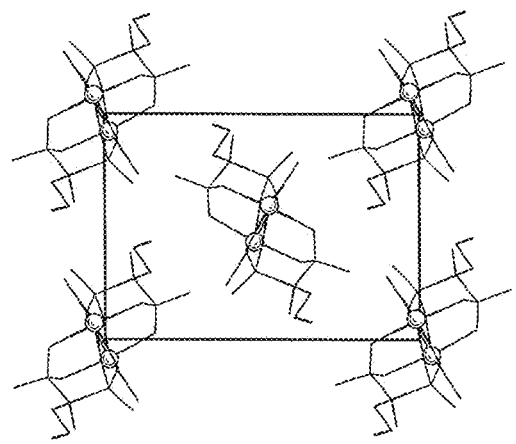
FIG. 2A is a schematic drawing showing a packing diagram of crystalline calcium pamidronate (Ca-Pam) viewed down the c axis.
Figure 2B:
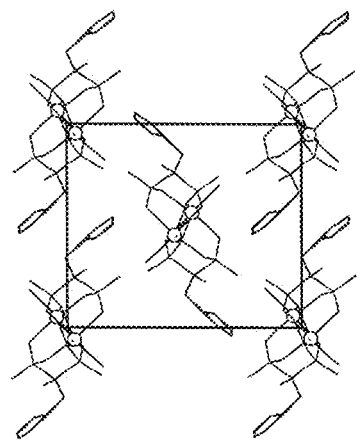
FIG. 2B is a schematic drawing showing a packing diagram of crystalline calcium zoledronate (Ca-Zol) viewed down the c axis.
Figure 2C:
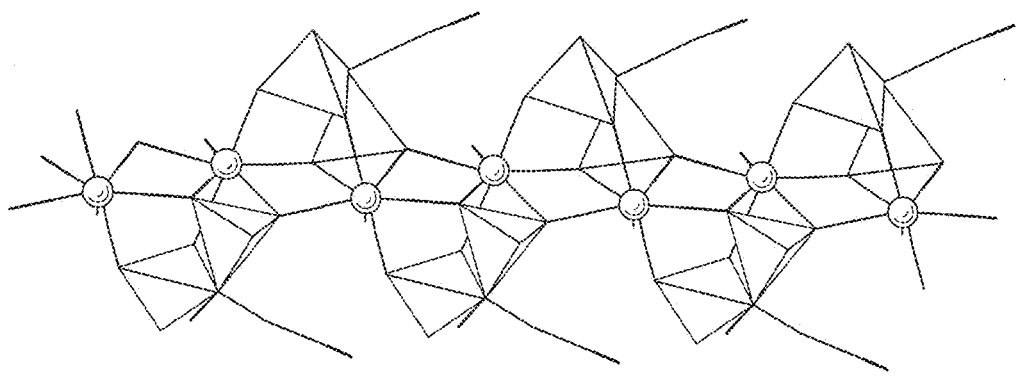
FIG. 2C is a schematic drawing showing a side view of the one-dimensional (1D) connectivity in crystalline calcium pamidronate (Ca-Pam) running along the c axis.
Figure 2D:
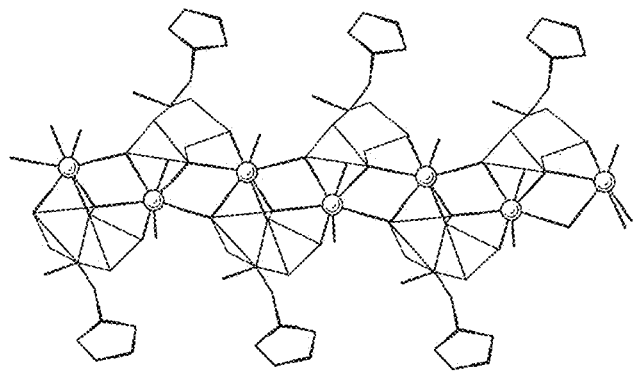
FIG. 2D is a schematic drawing showing a side view of the one-dimensional (1D) connectivity in crystalline calcium zoledronate (Ca-Zol) running along the c axis.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein.

Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (e.g., radius or diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

The terms "nanomaterial" and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is less than about 10 nm.

In some embodiments, the nanomaterial or nanoparticle is approximately spherical. When the nanoparticle is approximately spherical, the characteristic dimension can correspond to the radius or diameter of the sphere. In addition to spherical shapes, the nanomaterial can be disc-shaped, oblong, polyhedral, rod-shaped, cubic, or irregularly-shaped.

The nanoparticle can comprise a core region (i.e., the space between the outer dimensions of the particle) and an outer surface (i.e., the surface that defines the outer dimensions of the particle). In some embodiments, the nanoparticle can have one or more coating layers surrounding or partially surrounding the nanoparticle core. Thus, for example, a spherical nanoparticle can have one or more concentric coating layers, each successive layer being dispersed over the outer surface of a smaller layer closer to the center of the particle. The presently disclosed nanoparticle typically comprises a solid material comprising metal-bisphosphonate complexes, which can comprise one or more pores or hollow interior regions. The material can be amorphous or crystalline. In some embodiments, the nanoparticle core further comprises one or more optical imaging agents and/or non-bisphosphonate therapeutic agents (e.g., non-bisphosphonate anticancer agents), which can be physically trapped within the metal-bisphosphonate core material, coordinated to a metal ion of the metal-bisphosphonate core material, or chemically bonded (e.g., to a bisphosphonate) via a covalent or ionic bond. In some embodiments, the nanoparticle is essentially free of phosphate ions (i.e., $PO_4^{3-}$, $HPO_4^{2-}$, and $H_2PO_4^-$).

When the core comprises a non-bisphosphonate therapeutic agent or imaging agent, said agents can be said to be "embedded" in the nanoparticle. "Embedded" can refer to a therapeutic agent or an imaging agent that is bound, for example covalently bound or bound via a coordinative bond, inside the core of the particle (e.g., to a bisphosphonate or metal ion). Alternatively, the complex or agent can be sequestered (i.e., non-covalently encapsulated) inside pores in the core or interact with a core material via hydrogen bonding, London dispersion forces, or any other non-covalent interaction.

The terms "polymer" and "polymeric" refer to chemical structures that have repeating units (i.e., multiple copies of a given chemical substructure). Polymers can be formed from polymerizable monomers. A polymerizable monomer is a molecule that comprises one or more reactive moieties that can react to form bonds (e.g., covalent bonds) with reactive moieties on other molecules of polymerizable monomer. Generally, each polymerizable monomer molecule can bond to two or more other molecules. In some cases, a polymerizable monomer will bond to only one other molecule, forming a terminus of the polymeric material.

Polymers can be organic, or inorganic, or a combination thereof. As used herein, the term "inorganic" can refer to a compound or composition that contains at least some atoms other than carbon, hydrogen, nitrogen, oxygen, sulfur, phosphorous, or one of the halides. Thus, for example, an inorganic compound or composition can contain one or more silicon atoms and/or one or more metal atoms.

As used herein "organic polymers" are those that do not include silica or metal atoms in their repeating units. Exemplary organic polymers include polyvinylpyrrolidone (PVP), polyesters, polyamides, polyethers, polydienes, and the like. Some organic polymers contain biodegradable linkages, such as esters or amides, such that they can degrade overtime under biological conditions.

The term "hydrophilic polymer" as used herein generally refers to hydrophilic organic polymers, such as but not limited to, polyvinylpyrrolidone, polyvinylmethylether, polymethyloxazoline, polyethyloxazoline, polyhydroxypropyloxazoline, polyhydroxypropylmethacrylamide, polymethyacrylamide, polydimethylacrylamide, polyhydroxylpropylmethacrylate, polyhydroxyethylacrylate, hydroxymethylcellulose, hydroxyethylcellulose, polyethyleneglycol (i.e., PEG) or another hydrophilic poly(alkyleneoxide), polyglycerine, and polyaspartamide. The term "hydrophilic" refers to the ability of a molecule or chemical species to interact with water. Thus, hydrophilic polymers are typically polar or have groups that can hydrogen bond to water.

The term "imaging agent" refers to a chemical moiety that aids in the visualization of a sample. For example, an imaging agent can be a "contrast agent", and can refer to a moiety (a specific part of or an entire molecule, macromolecule, coordination complex, or nanoparticle) that increases the contrast of a biological tissue or structure being examined. The contrast agent can increase the contrast of a structure being examined using magnetic resonance imaging (MRI), optical imaging, positron emission tomography (PET) imaging, single photon emission computed tomography (SPECT) imaging, or a combination thereof (i.e., the contrast agent can be multimodal).

The term "MRI contrast agent" refers to a moiety that effects a change in induced relaxation rates of water protons in a sample.

The terms "optical imaging agent" or "optical contrast agent" refer to a group that can be detected based upon an ability to absorb, reflect or emit light (e.g., ultraviolet, visible, or infrared light). Optical imaging agents can be detected based on a change in amount of absorbance, reflectance, or fluorescence, or a change in the number of absorbance peaks or their wavelength maxima. Thus, optical imaging agents include those which can be detected based on fluorescence or luminescence, including organic and inorganic dyes.

As used herein, the term "ligand" refers generally to a chemical species, such as a molecule or ion, which interacts (e.g., binds or chelates) in some way with another species. The term "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The term "ligand" can also refer to a molecule involved in a biospecific recognition event (e.g., antibody-antigen binding, enzyme-substrate recognition, receptor-receptor ligand binding, etc).

A "coordination complex" is a compound in which there is a coordinate bond between a metal ion and an electron pair donor (i.e., chelating group or a ligand). Thus, chelating groups are generally electron pair donors, molecules or molecular ions having unshared electron pairs available for donation to a metal ion. Chelating groups or metal ion ligands can be monodentate or multidentate. "Multidentate" refers to a chelating agent that has two, three, four or more electrons pairs available for donation to a metal ion and that can coordinate to a metal ion at more than one coordination site. "Monodentate" refers to a chelating agent that coordinates to a metal ion at only one coordination site.

The terms "bonding" or "bonded" and variations thereof can refer to either covalent or non-covalent bonding. In some cases, the term "bonding" refers to bonding via a coordinate bond. The term "conjugation" can refer to a bonding process, as well, such as the formation of a covalent linkage or a coordinate bond.

The term "coordination" refers to an interaction in which one multi-electron pair donor coordinately bonds, i.e., is "coordinated," to one metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as have more or less covalent character (if not entirely covalent character) depending on the characteristics of the metal ion and the electron pair donor.

As used herein, the term "paramagnetic metal ion" refers to a metal ion that is magnetized parallel or antiparallel to a magnetic field to an extent proportional to the field. Generally, paramagnetic metal ions are metal ions that have unpaired electrons. Paramagnetic metal ions can be selected from the group consisting of transition and inner transition elements, including, but not limited to, scandium, titanium, vanadium, chromium, cobalt, nickel, copper, molybdenum, ruthenium, cerium, praseodymium, neodymium, promethium, samarium, europium, terbium, holmium, erbium, thulium, and ytterbium. In some embodiments, the paramagnetic metal ions can be selected from the group consisting of gadolinium III (i.e., $Gd^{+3}$ or Gd(III)); manganese II (i.e., $Mn^{+2}$ or Mn(II)); copper II (i.e., $Cu^{+2}$ or Cu(II)); chromium III (i.e., $Cr^{+3}$ or Cr(III)); iron II (i.e., $Fe^{+2}$ or Fe(II)); iron III (i.e., $Fe^{+3}$ or Fe(III)); cobalt II (i.e., $Co^{+2}$ or Co(II)); erbium II (i.e., $Er^{+2}$ or Er(II)), nickel II (i.e., $Ni^{+2}$ or Ni(II)); europium III (i.e., $Eu^{+3}$ or Eu(III)); yttrium III (i.e., $Yt^{+3}$ or Yt(III)); and dysprosium III (i.e., $Dy^{+3}$ or Dy(III)). In some embodiments, the paramagnetic ion is the lanthanide atom Gd(III), due to its high magnetic moment, symmetric electronic ground state, and its current approval for diagnostic use in humans.

"Luminescence" occurs when a molecule (or other chemical species) in an electronically excited state relaxes to a lower energy state by the emission of a photon. The luminescent agent in one embodiment can be a chemiluminescent agent. In chemiluminescence, the excited state is generated as a result of a chemical reaction, such as lumisol and isoluminol. In photoluminescence, such as fluorescence and phosphorescence, an electronically excited state is generated by the illumination of a molecule with an external light source. Bioluminescence can occur as the result of action by an enzyme, such as luciferase. In electrochemiluminescence (ECL), the electronically excited state is generated upon exposure of the molecule (or a precursor molecule) to electrochemical energy in an appropriate surrounding chemical environment. Examples of electrochemiluminescent agents are provided, for example, in U.S. Pat. Nos. 5,147,806; and 5,641,623; and in U.S. Patent Application Publication No. 2001/0018187; and include, but are not limited to, metal cation-liquid complexes, substituted or unsubstituted polyaromatic molecules, and mixed systems such as aryl derivatives of isobenzofurans and indoles. An electrochemiluminescent chemical moiety can comprise, in some embodiments, a metal-containing organic compound wherein the metal is selected from the group consisting of ruthenium, osmium, rhenium, iridium, rhodium, platinum, palladium, molybdenum, technetium and tungsten.

As described above, the term "fluorophore" refers to a species that can be excited by visible light or non-visible light (e.g., UV light). Examples of fluorophores include, but are not limited to: quantum dots and doped quantum dots (e.g., a semiconducting CdSe quantum dot or a Mn-doped CdSe quantum dot), fluorescein, fluorescein derivatives and analogues, indocyanine green, rhodamine, triphenylmethines, polymethines, cyanines, phalocyanines, naphthocyanines, merocyanines, lanthanide complexes or cryptates, fullerenes, oxatellurazoles, LaJolla blue, porphyrins and porphyrin analogues and natural chromophores/fluorophores such as chlorophyll, carotenoids, flavonoids, bilins, phytochrome, phycobilins, phycoerythrin, phycocyanines, retinoic acid and analogues such as retinoins and retinates.

The term "quantum dot" refers to semiconductor nanoparticles comprising an inorganic crystalline material that is luminescent (i.e., that is capable of emitting electromagnetic radiation upon excitation). The quantum dot can include an inner core of one or more first semiconductor materials that is optionally contained within an overcoating or "shell" of a second semiconductor material. A semiconductor nanocrystal core surrounded by a semiconductor shell is referred to as a "core/shell" semiconductor nanocrystal. The surrounding shell material can optionally have a bandgap energy that is larger than the bandgap energy of the core material and can be chosen to have an atomic spacing close to that of the core substrate.

Suitable semiconductor materials for quantum dots include, but are not limited to, materials comprising a first element selected from Groups 2 and 12 of the Periodic Table of the Elements and a second element selected from Group 16. Such materials include, but are not limited to ZnS, ZnSe, ZnTe, CDs, CdSe, CdTe, HgS, HgSe, HgTe, MgS, MgSe, MgTe, CaS, CaSe, CaTe, SrS, SrSe, SrTe, BaS, BaSe, BaTe, and the like. Suitable semiconductor materials also include materials comprising a first element selected from Group 13 of the Periodic Table of the Elements and a second element selected from Group 15. Such materials include, but are not limited to, GaN, GaP, GaAs, GaSb, InN, InP, InAs, InSb, and the like. Semiconductor materials further include materials comprising a Group 14 element (Ge, Si, and the like); materials such as PbS, PbSe and the like; and alloys and mixtures thereof. As used herein, all reference to the Periodic Table of the Elements and groups thereof is to the new IUPAC system for numbering element groups, as set forth in the Handbook of Chemistry and Physics, 81st Edition (CRC Press, 2000).

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Dialkylamino" refers to an —NRR' group wherein each of R and R' is independently an alkyl group and/or a substituted alkyl group as previously described. Exemplary dialkylamino groups include ethylmethylamino, dimethylamino, and diethylamino. "Alkylamino" refers to a —NRR' group wherein one of R and R' is H and the other of R and R' is alkyl or substituted alkyl.

The term "amino" refers to the —NH$_2$ group. "Amino" can also refer to a dialkylamino or alkylamino group as described above.

The term "arylamino" refers to an aryl-N(R)— group, wherein R is H, alkyl, substituted alkyl, aryl or substituted aryl.

The terms "halo", "halide", or "halogen" as used herein refer to fluoro, chloro, bromo, and iodo groups.

The term "hydroxyl" refers to the —OH group.

The terms "mercapto" or "thiol" refer to the —SH group.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

The term "alkylthio" refers to the alkyl-S— group.

"Aryloxyl" refers to an aryl-O— group wherein the aryl group is as previously described, including a substituted aryl. The term "aryloxyl" as used herein can refer to phenyloxyl and alkyl, substituted alkyl, halo, or alkoxyl substituted phenyloxyl.

The term "arylthio" refers to the aryl-S— group.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

The term "phosphonate" refers to the —P(=O)(OR)$_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "silyl" refers to groups comprising silicon atoms (Si).

The term "siloxane" refers to a compound comprising a —Si—O—Si— linkage. The term "poly(siloxane)" as used herein refers to a polymeric group or compound of the formula R$_2$SiO, wherein R is H, alkyl, aralkyl, or aryl.

The term "poly(silsesquioxane)" refers to a polymeric group or compound of the formula RSiO$_{1.5}$, wherein R is H, alkyl, aralkyl, or aryl.

The term "lipid" can refer to a hydrophobic or amphiphilic small molecule, such as, but not limited to a fatty acid, a phospholipid, a glycerolipid, a glycerophospholipid, a sphingolipid, a saccharolipid, or a polyketide.

The term "hydrophobic" refers to molecule or species that has a lack of ability to interact with water. The term "amphiphilic" refers to a molecule or species that has both hydrophilic and hydrophobic attributes.

The term "cancer" as used herein refers to diseases caused by uncontrolled cell division and the ability of cells to metastasize, or to establish new growth in additional sites.

The terms "malignant", "malignancy", "neoplasm", "tumor," "cancer" and variations thereof refer to cancerous cells or groups of cancerous cells.

Specific types of cancer include, but are not limited to, skin cancers (e.g., melanoma), connective tissue cancers (e.g., sarcomas), adipose cancers, breast cancers, head and neck cancers, lung cancers (e.g., mesothelioma), stomach cancers, pancreatic cancers, ovarian cancers, cervical cancers, uterine cancers, anogenital cancers (e.g., testicular cancer), kidney cancers, bladder cancers, colon cancers, prostate cancers, central nervous system (CNS) cancers, retinal cancer, blood, neuroblastomas, multiple myeloma, and lymphoid cancers (e.g., Hodgkin's and non-Hodgkin's lymophomas).

The terms "anticancer drug" and "anticancer prodrug" refer to drugs or prodrugs known to, or suspected of being able to treat a cancer (i.e., to kill cancer cells, prohibit proliferation of cancer cells, or treat a symptom related to cancer).

II. General Considerations

In some embodiments, the presently disclosed subject matter relates to metal bisphosphonate nanomaterials (e.g., nanoparticles), including the synthesis of these nanomaterials, their surface modification and functionalization, and their use as anticancer and/or bone-related disorder therapeutic agents or their use as both therapeutic agents and imaging contrast agents. The nanomaterials can be based on the coordination of bisphosphonates with metal ions.

Generally, the nanomaterials can comprise a solid crystalline or amorphous metal ion-bisphosphonate material. The synthesis of the nanoparticles can be tuned to achieve either a crystalline or amorphous material by appropriate choice of synthetic conditions (e.g., solvent, concentration, temperature and/or pH). In some embodiments, the nanoparticles can comprise, for example, 50% or more (e.g., 50%, 55%, 60%, 65%, 70%, 75%, 80%, 85%, or more) bisphosphonate by weight.

In some embodiments, the metal-bisphosphonate nanoparticle can be prepared by a method comprising: providing a solution comprising a bisphosphonate and a multivalent metal ion; aging the solution comprising the bisphosphonate and the multivalent metal ion for a period of time to provide an aged solution; and isolating a metal-bisphosphonate nanoparticle from the aged solution. In some embodiments, the multivalent metal ion is divalent. Suitable divalent ions include, but are not limited to $Ca^{2+}$, $Mg^{2+}$, $Mn^{2+}$, $Zn^{2+}$ and combinations thereof. In some embodiments, the solution comprising the bisphosphonate and the multivalent metal ion comprises at least two different multivalent metal ions and/or at least one paramagnetic metal ion. In some embodiments, the solution comprises a single type of multivalent metal ion. In some embodiments, the solution is free of paramagnetic metal ions, phosphate ions, and/or platinum ions.

Any suitable bisphosphonate compound or complex can be used. In some embodiments, the bisphosphonate is a compound with two phosphonate groups that are both attached to the same carbon atom or to the same carbon atom chain. In some embodiments, the bisphosphonate has a structure of Formula (I):

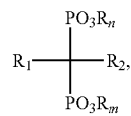

wherein n and m are each independently an integer between 0 and 2 (i.e., each independently 0, 1, or 2); each R is independently H, alkyl, substituted alkyl, aralkyl, aryl, or substituted aryl; $R_1$ is H, hydroxyl, halo, alkyl, substituted alkyl, amino, alkoxy, or alkylthio; and $R_2$ is halo, alkyl, substituted alkyl, aralkyl, substituted aralkyl, alkoxy, alkylthio, aryloxy, arylthio or arylamino; or a salt thereof. In some embodiments, at least one of n and m is 2. In some embodiments, at least one of n and m is 1. In some embodiments, each R is H. In some embodiments, $R_1$ is hydroxyl or H.

In some embodiments, $R_2$ is a substituted alkyl or an aralkyl group. In some embodiments, the $R_2$ substituted alkyl group is $NH_2$-substituted alkyl, alkylamino-substituted alkyl, or dialkylamino-substituted alkyl. In some embodiments, the $R_2$ aralkyl group comprises a nitrogen-containing heteroaryl moiety (e.g., imidazole or pyridine).

Thus, suitable bisphosphonates include, but are not limited to, zoledronic acid, pamidronate, risedronic acid, alendronate, zeridronic acid, tiludronate, etidronate, and ibandronate. The structures of these bisphosphonates are shown in Scheme 1, below.

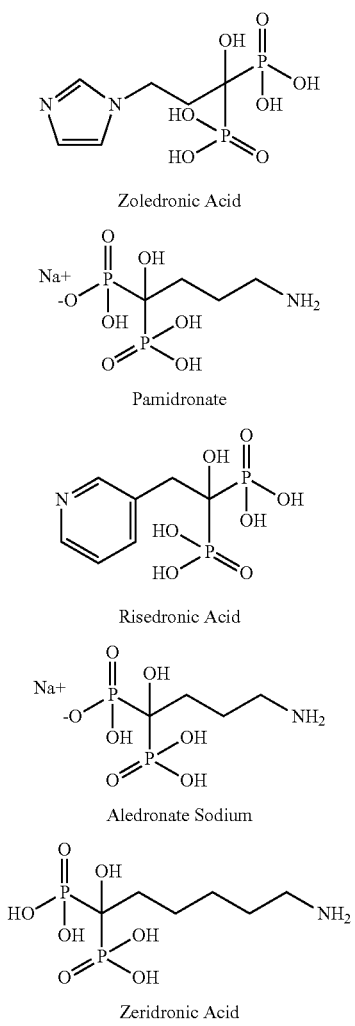

Scheme 1. Examples of Bisphosphonates.

Zoledronic Acid

Pamidronate

Risedronic Acid

Aledronate Sodium

Zeridronic Acid

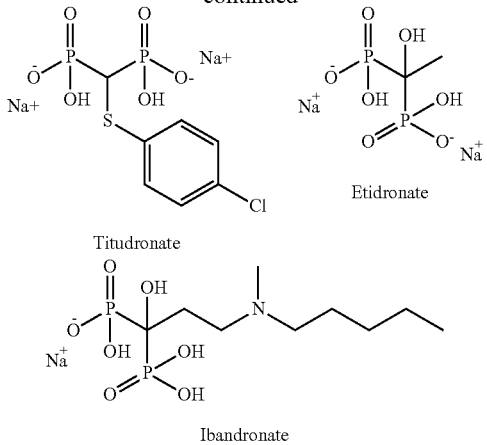

-continued

Titudronate

Etidronate

Ibandronate

In some embodiments, the bisphosphonate is not a compound of Formula (I). In some embodiments, the bisphosphonate is a metal complex wherein at least two metal ligands comprise a phosphonate group that is not coordinated to the metal of the metal complex. For example, in some embodiments, the bisphosphonate is a platinum metal complex (e.g., cisplatin, oxaliplatin, or a similar compound) wherein two platinum ligands have been replaced by or conjugated to phosphonate-containing groups. Thus, in some embodiments, the bisphosphonate is a metal complex of the formula $M_2L_x$, wherein x is an integer of 2 or greater, $M_2$ is a metal ion (e.g., Pt), each L is a metal ion ligand, and wherein at least two L comprise a phosphonate group. In some embodiments, the bisphosphonate can have the formula $M_2L_{x-2}[-O-C(=O)-NH-P(=O)(OR)_2]_2$, wherein each R is independently H, alkyl, substituted alkyl, aralkyl, aryl, substituted aryl or a negative charge.

In some embodiments, the solution comprising the bisphosphonate and the multivalent metal ion can be provided by dissolving the bisphosphonate and a multivalent metal precursor in a solvent. In some embodiments, the solvent is an aqueous solvent or a combination of water and a water miscible solvent, such as, but not limited to dimethyl sulfoxide (DMSO), dimethylformamide (DMF), acetonitrile, acetone, or a water-miscible alcohol. In some embodiments, the solvent is water or a mixture of water and DMF.

The multivalent metal precursor can be a compound of the formula $ML_x$, wherein x is an integer corresponding to the valency of the metal ion, M is a multivalent metal ion, and each L is a ligand. Suitable ligands for the metal precursors include, but are not limited to, halo, hydroxyl, sulfate, nitrate, and amino. In some embodiments, the multivalent metal precursor is a hydrate or a solvate of a compound of the formula $ML_x$. In some embodiments, the multivalent metal precursor is a metal halide (e.g., $CaCl_2$ or $MnCl_2$) or a hydrate or solvate thereof.

In some embodiments, the solution comprising the bisphosphonate and the multivalent metal ion can be provided by mixing a precursor solution of the bisphosphonate with a precursor solution that comprises the multivalent metal ion. The precursor solution comprising the multivalent metal ion can be prepared by dissolving a multivalent metal precursor (e.g., a compound of formula $ML_x$ or a hydrate or solvate thereof) in a suitable solvent. The precursor solution of the bisphosphonate can be prepared by dissolving a bisphosphonate in a suitable solvent.

In some embodiments, the bisphosphonate and the metal precursor are mixed together in one or more microemulsions. In some embodiments, one or more of the microemulsions can contain a lipid such that the nanoparticle can be formed already containing a lipid layer (e.g., a single lipid layer) over at least a portion of the outer surface of the nanoparticle. In some embodiments, the lipid is DOPA, DOTAP, DOPC, DOPE, oleic acid, stearic acid, octadecyl phosphoric acid, or octadecyl phosphonic acid.

In some embodiments, providing the solution comprising the bisphosphonate and the multivalent metal ion further includes adjusting the pH of the solution or of a precursor solution (i.e., of the precursor solution comprising the bisphosphonate and/or of the multivalent metal ion). For example, a pH adjusting chemical (i.e., a compound that raises or lowers the pH, such as ammonia or HCl) can be added to one or more solution.

In addition to bisphosphonates, other suitable therapeutic agents or their produgs can be incorporated into the metal-bisphosphonate nanoparticle formulations. The therapeutic efficacy of these nanomaterials can either derive from the anticancer activity of the drugs (cargoes) contained within the nanoparticles or can be a result of external triggers such as laser photon activation as in photodynamic therapy or ionizing radiation (such as X-rays) as in radiation sensitization.

In some embodiments, the presently disclosed nanoparticles can include one or more imaging contrast agent. The imaging contrast agents that can be contained in the nanoparticles can range from highly paramagnetic centers (such as $Mn^{2+}$) for magnetic resonance imaging (MRI), optical fluorophores for optical imaging, and radioactive metal centers (such as $^{64}Cu$, $^{111}In$, and $^{99m}Tc$) for positron emission tomography (PET) or single photon positron emission tomography (SPECT) imaging. Some of the nanoparticles can also contain both conventional anticancer drugs or prodrugs and beta-emitting radionuclides (such as $^{99}Y$) for combined chemo- and radio-therapy.

Thus, in some embodiments, providing a solution comprising the bisphosphonate and the multivalent metal ion further comprises adding one or more non-bisphosphonate therapeutic agent or prodrug thereof and/or one or more imaging agent to the solution comprising the bisphosphonate and the multivalent metal ion or to a precursor solution thereof. These non-bisphosphonate therapeutic agents or prodrugs and/or imaging agents can include, for example, chemotherapeutics, photodynamic therapy agents, radiosensitizers, beta-emitting radionuclides, therapeutic proteins or peptides, small interfering RNA (siRNA) and fluorophores. In some embodiments, the non-bisphosphonate therapeutic agent, prodrug thereof, and/or imaging agent comprises a functional group or groups (e.g., a hydroxyl, amino, carboxyl, etc) that can coordinate to the multivalent metal ion. In some embodiments, the non-bisphosphonate therapeutic agent, prodrug or imaging agent is covalently bonded to a bisphosphonate. In some embodiments, the covalent bond can be designed to be cleavable under physiological conditions (e.g., at a certain pH or in the presence of certain enzymes).

In some embodiments, the solution comprising the bisphosphonate and the multivalent metal ion is subjected to microwaves prior to aging. In some embodiments, the aging comprises heating the solution comprising the bisphosphonate and the multivalent metal ion to a temperature above room temperature (e.g., above about 20, 21, 22, 23, 24, or 25° C.) for a period of time. In some embodiments, the temperature above room temperature is between about 80° C. and about 140° C. (e.g., is about 80, 85, 90, 95, 100, 105, 110, 115, 120, 125, 130, 135, or 140° C.). In some embodiments, the period of time is between about 20 minutes and about 24 hours (e.g., about 20, 25, 30, 35, 40, 45, 50, 55, or 60 minutes or about 2, 3, 4, 5, 6, 7, 8, 9, 10, 11, 12, 13, 14, 15, 16, 17, 18, 19, 20, 21, 22, 23, or 24 hours). In some embodiments, the period of time is longer than one day.

The metal-bisphosphonate nanoparticles can be isolated by any suitable technique or combination of techniques. Suitable techniques include, but are not limited to, centrifugation, filtration, decantation, washing, lyophilization, dialysis, and drying. In some embodiments, isolating the metal-bisphosphonate nanoparticles comprises one or more of centrifuging the aged solution to provide crude nanoparticles, filtering the aged solution to provide crude nanoparticles, re-dispersing the crude nanoparticles in a solution (e.g., an alcohol solution, such as ethanol or methanol), washing the crude nanoparticles with an aqueous solution, washing the crude nanoparticles with an alcoholic solution, and drying the crude nanoparticles. In some embodiments, crystalline metal-bisphosphonate nanoparticles are isolated.

In some embodiments, the nanoparticles can be coated with one or more coating agents or layers, such as, but not limited to, a metal oxide, a polymer (e.g., a silica-based polymer, including, but not limited to silica ($SiO_2$), a poly(siloxane), or a poly(silsesquioxane), or an organic polymer), a single lipid layer, a lipid bilayer, and combinations thereof, to provide coated nanoparticles. Thus, some of the nanoparticles can be coated with a silica or silica-based layer, another polymer coating (i.e., another inorganic or organic polymer coating), or a lipid coating for stabilization and surface functionalization. In some embodiments, the coating comprises an organic polymer. In some embodiments, the organic polymer is a hydrophilic polymer (e.g., PEG or PVP). Some of the nanoparticles can be directly encapsulated within liposomes. The nanomaterials can further include targeting agents to direct the nanomaterials to specific sites for use in target-specific therapy and imaging. Some of the nanomaterials can be coated with a passivating moiety.

In some embodiments, the presently disclosed subject matter relates to a method to entrap bisphosphonates in metal-bisphosphonate nanoparticles to selectively deliver the bisphosphonates to cancer cells (e.g., lung cancer cells, breast cancer cells, or prostate cancer cells). In addition, other anticancer drugs or their prodrugs and therapeutic radionuclides can be entrapped into the metal-bisphosphonate nanoparticles to allow synergistic antitumor effects.

In some embodiments, the presently disclosed nanoparticles can be used to render an image of a cell, a tissue, an organ or a subject following administration. Rendering the image can comprise performing, for example, MRI, optical imaging, PET, or SPECT. In some embodiments, the image rendering is done in conjugation with treatment of a subject.

In some embodiments, the presently disclosed nanoparticles can be stabilized against premature dissolution and/or so that they only release therapeutic and/or imaging contrast agent cargoes inside cancer cells by taking advantage of their unique cellular environmental factors (such as lower pH and more reducing environment). This stabilization can be achieved by coating the nanoparticles with, for example, a thin layer of silica, poly(siloxane), another polymer (e.g., an organic polymer), a single lipid layer, or lipid bilayers.

In some embodiments, the metal-bisphosphonate nanoparticles can accumulate in tumors by taking advantage of the enhanced permeability and retention (EPR) effect. The EPR effect is the selective concentration of macromolecules and small particles in the tumor microenvironment, caused by the hyperpermeable vasculature and poor lymphatic drainage of tumors. To enhance this effect (i.e. EPR), in some embodiments, the exterior of the particle can be coated with, or conjugated to, a hydrophilic polymer to increase the circulation half-life of the particle and to passivate the surface against plasma protein adsorption.

In some embodiments, the metal-bisphosphonate nanoparticles can further comprise a targeting agent to direct the nanoparticle, once administered, to a cancer cell. Any targeting moiety known to be located on the surface of the target diseased cells (e.g., tumor cells) can find use with the presently disclosed nanoparticles. For example, an antibody directed against a cell surface antigen can be used. Alternatively, the targeting moiety can be a ligand directed to a receptor present on the cell surface or vice versa. In some embodiments, targeting moieties including small molecules, peptides, and proteins can be used to direct the presently disclosed nanoparticles to tumors.

Finally, as a result of their enhanced pharmacokinetics, in some embodiments, the metal-bisphosphonate nanoparticles can be used as potent inhibitors of bone resorption. They can also be used to treat bone-resorption related diseases, osteoporosis, Paget's disease, and bone metastases. The bisphosphonate nanoparticles can also provide novel vehicles for delivering imaging agents, including but not limited to $^{99m}$Tc for SPECT imaging of bone diseases (such as bone metastases of various cancers).

Accordingly, in some embodiments, the presently disclosed subject matter provides pharmaceutical compositions comprising a metal-bisphosphonate nanoparticle and a pharmaceutically acceptable carrier. In some embodiments, an effective amount of a metal-bisphosphonate nanoparticles and/or of a pharmaceutical composition thereof can be administered a subject to provide treatment for a cancer or a bone-related disorder.

III. Crystalline Metal-Bisphosphonate Nanoparticles

As shown in Scheme 2 (below), in some embodiments, metal ions (such as $Ca^{2+}$, $Mg^{2+}$, $Mn^{2+}$, $Fe^{3+}$, $Zn^{2+}$, and others in the periodic table) can be used to link bisphosphonates (e.g., via coordinative bonds) to form crystalline nanoparticles. The $M^{n+}$ ions in Scheme 2 can be divalent, trivalent, and tetravalent ions, or some other higher valency metal ions. Because of their crystalline structures, these nanoparticles can have non-spherical morphologies which can have advantages in entering cancer cells. The stabilities of these nanoparticles can be readily tuned as a result of the different metal-phosphonate bond strengths. X-ray crystal structures of these metal-bisphosphonate nanoparticles can be determined, which can allow the precise analysis of the drug contents and other important characteristics of such nanoparticles. The crystalline nature of these metal-bisphosphonate nanoparticles can provide that every single batch of the nanoparticle will have precisely the same composition, which is not the case for most existing nanoparticles (which are amorphous with relatively poorly-defined compositions). In some embodiments, the crystalline metal-bisphosphonate nanoparticles can be selectively delivered to cancer cells, without being readily cleared through kidney filtration or binding to the bones, to allow superior efficacy in killing cancer cells.

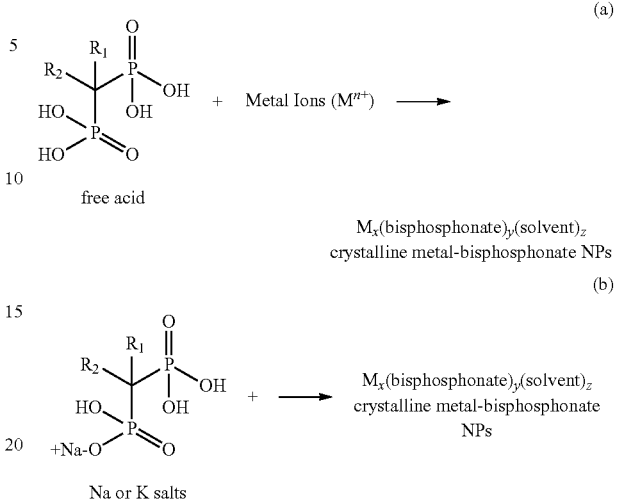

Scheme 2. Synthesis of Crystalline Metal-Bisphosphonate Nanoparticles.

Accordingly, in some embodiments, the presently disclosed subject matter provides a metal-bisphosphonate nanoparticle comprising a crystalline multivalent metal ion-bisphosphonate complex. In some embodiments, the crystalline multivalent metal ion-bisphosphonate nanoparticle can be coated with one or more coating agents or layers to surround at least a portion of an outer surface of the nanoparticle. Suitable coating agents or layers include, but are not limited to, metal oxide, polymer (e.g., a silica-based polymer, such as silica, poly(siloxane), or poly(silsesquioxane), or an organic or hydrophilic organic polymer), a single lipid layer, a lipid bilayer, or a combination thereof. In some embodiments, one or more of the coating agents or layers can be derivatized with a targeting agent and/or a passivating agent. In some embodiments, the one or more coating agents or layers are selected from the group comprising dioleoyl L-α-phosphatidylethanolamine (DOPE), 1,2-dioleoyl-sn-glycero-3-phosphocholine (DOPC), 1,2-dioleoyl-sn-glycero-3-phosphate sodium salt (DOPA), 1,2-distearoyl-sn-glycero-3-phosphoethanolamine-N-[amino(polyethylene glycol)2000] (DSPE-PEG$_{2k}$), 1,2-dioleoyl-3-trimethylammonium propane (DOTAP), anisamide-derivatized DOPE, silica, cRGfK-derivatized silica, polyethylene glycol (PEG)-derivatized silica, and anisamide-PEG-derivatized silica.

In some embodiments, the multivalent metal ion is divalent. Suitable divalent ions include, but are not limited to $Ca^{2+}$, $Mg^{2+}$, $Mn^{2+}$, $Zn^{2+}$ and combinations thereof. In some embodiments, the complex comprises at least two different multivalent metal ions and/or at least one paramagnetic metal ion. In some embodiments, the complex comprises a single type of multivalent metal ion. In some embodiments, the complex is free of paramagnetic metal ions, phosphate ions, and/or platinum ions.

In some embodiments, the bisphosphonate has a structure of Formula (I):

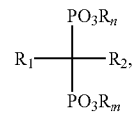

wherein n and m are each independently an integer between 0 and 2 (i.e., each independently 0, 1, or 2); each R is independently H, alkyl, substituted alkyl, aralkyl, aryl, or substituted aryl; $R_1$ is H, hydroxyl, halo, alkyl, substituted alkyl, amino, alkoxy, or alkylthio; and $R_2$ is halo, alkyl, substituted alkyl, aralkyl, substituted aralkyl, alkoxy, alkylthio, aryloxy, arylthio or arylamino; or an anion or salt thereof. In some embodiments, $R_2$ is a substituted alkyl or an aralkyl group. In some embodiments, the $R_2$ substituted alkyl group is $NH_2$-substituted alkyl, alkylamino-substituted alkyl, or dialkylamino-substituted alkyl. In some embodiments, the $R_2$ aralkyl group comprises a nitrogen-containing heteroaryl moiety. Thus, suitable bisphosphonates include, but are not limited to, zoledronic acid, pamidronate, risedronic acid, alendronate, zeridronic acid, tiludronate, etidronate, and ibandronate.

In some embodiments, the crystalline metal-bisphosphonate nanoparticle further comprises a non-bisphosphonate therapeutic agent or prodrug thereof and/or an imaging agent. These additional agents can be embedded or sequestered within the crystalline metal-bisphosphonate nanoparticle.

IV. Amorphous Metal-Bisphosphonate Nanoparticles

As shown in Scheme 3 (below), in some embodiments, under suitable conditions (e.g., temperature, solvent, pH), amorphous metal-bisphosphonate nanoparticles can be obtained. These nanoparticles can have complimentary properties to those of the crystalline metal-bisphosphonate nanoparticles.

Scheme 3. Synthesis of Amorphous Metal-Bisphosphonate Nanoparticles.

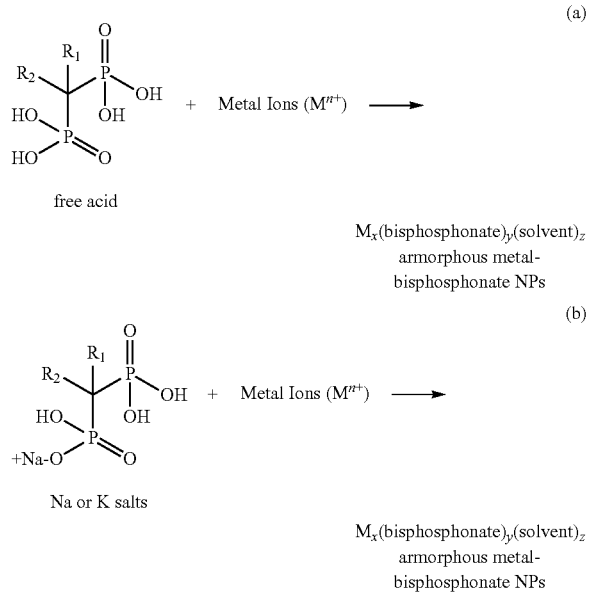

Accordingly, in some embodiments, the presently disclosed subject matter provides a metal-bisphosphonate nanoparticle comprising an amorphous multivalent metal ion-bisphosphonate complex. In some embodiments, the amorphous multivalent metal ion-bisphosphonate nanoparticle can be coated with one or more coating agents or layers to surround at least a portion of an outer surface of the core metal ion-bisphosphonate complex. Suitable coating agents or layers include, but are not limited to, metal oxide, polymer (e.g., a silica-based polymer, such as silica, poly (siloxane), or poly(silsesquioxane), or an organic or hydrophilic organic polymer), a single lipid layer, a lipid bilayer, or a combination thereof. In some embodiments, one or more of the coating agents or layers can be derivatized with a targeting agent and/or a passivating agent. In some embodiments, the one or more coating agents or layers are selected from the group comprising DOPE, DOPC, DOPA, DSPE-PEG$_{2k}$, DOTAP, anisamide-derivatized DOPE, silica, cRGfK-derivatized silica, PEG-derivatized silica, and anisamide-PEG-derivatized silica.

In some embodiments, the multivalent metal ion is divalent. Suitable divalent ions include, but are not limited to $Ca^{2+}$, $Mg^{2+}$, $Mn^{2+}$, $Zn^{2+}$ and combinations thereof. In some embodiments, the complex comprising the bisphosphonate and the multivalent metal ion comprises at least two different multivalent metal ions and/or at least one paramagnetic metal ion. In some embodiments, the complex comprises a single type of multivalent metal ion. In some embodiments, the complex is free of paramagnetic metal ions, phosphate ions, and/or platinum ions.

In some embodiments, the bisphosphonate has a structure of Formula (I):

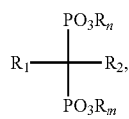

wherein n and m are each independently an integer between 0 and 2 (i.e., each independently 0, 1, or 2); each R is independently H, alkyl, substituted alkyl, aralkyl, aryl, or substituted aryl; $R_1$ is H, hydroxyl, halo, alkyl, substituted alkyl, amino, alkoxy, or alkylthio; and $R_2$ is halo, alkyl, substituted alkyl, aralkyl, substituted aralkyl, alkoxy, alkylthio, aryloxy, arylthio or arylamino; or a salt thereof. In some embodiments, $R_2$ is a substituted alkyl or an aralkyl group. In some embodiments, the $R_2$ substituted alkyl group is $NH_2$-substituted alkyl, alkylamino-substituted alkyl, or dialkylamino-substituted alkyl. In some embodiments, the $R_2$ aralkyl group comprises a nitrogen-containing heteroaryl moiety. Thus, suitable bisphosphonates include, but are not limited to, zoledronic acid, pamidronate, risedronic acid, alendronate, zeridronic acid, tiludronate, etidronate, and ibandronate.

In some embodiments, the amorphous metal-bisphosphonate nanoparticle further comprises a non-bisphosphonate therapeutic agent or prodrug thereof and/or an imaging agent. These additional agents can be embedded or sequestered within the amorphous metal-bisphosphonate nanoparticle.

V. Metal-bisphosphonate Nanoparticles Containing Additional Therapeutic Agents

Many of the currently used anticancer drugs or their prodrugs contain functional groups (e.g., proton acceptor or donor groups, such as carboxylic acid, hydroxyl, ether, amido, amino, etc.) that can allow their entrapment in metal-bisphosphonate nanoparticles. For example, the functional groups can coordinate to the metal centers in the metal-bisphosphonates. Exemplary anticancer drugs and prodrugs include, but are not limited to, cisplatin or oxaliplatin prodrugs, methotrexate, leucovorin, pemetrexed disodium, doxorubicin, vinblastine, vincristine, vindesine, cytarabine, azathioprine, melphalan, imatinib, anastrozole, and letrozole. See FIG. 1. Thus, in some embodiments, using the appropriate metal centers, anticancer drugs, such as, but not limited to, those shown in FIG. 1, and/or their respective prodrugs, can be incorporated into the presently disclosed metal-bisphosphonate nanoparticles. These can be either amorphous or crystalline nanoparticles, or can be provided in both. In some embodiments, the additional (e.g., non-bisphosphonate) therapeutic agent is not an anticancer drug, but can be an anti-inflammatory, anti-infective, immunomodulatory, or other type of therapeutic agent. In some embodiments, the additional therapeutics contained within the metal-bisphosphonate nanoparticles can be selected from the group comprising a chemotherapeutic, a PDT agent, a radiosensitizer, a beta-emitting radionuclide, or a biologic drug such as a protein, small interfering RNA molecule. These metal-bisphosphonate nanoparticles containing a second (or third or fourth) therapeutic agent can allow the drugs to synergistically kill the cancer cells. Thus, in some embodiments, they can have superior therapeutic indices.

VI. Coordination Polymer Nanoparticles Containing Anticancer Druqs/Prodruqs that Only Become Cytotoxic with External Stimuli In some embodiments, the methods described in preceding sections can be used to incorporate anticancer drugs that require external stimuli such as intense laser light or X-ray radiation to render them cytotoxic. For example, porfimer sodium (PHOTOFRIN®, Axcan Pharma PDT, Inc., Birmingham, Ala., United States of America) has been widely used as a sensitizer for photodynamic therapy (PDT). Other drugs, such as motexafin gadolinium (XCYTRIN®, Pharmacyclic, Sunnyvale, Calif., United States of America), are used as prototype radiosensitizers. Both PDT agents and radiosensitizers can be incorporated into the metal-bisphosphonate nanoparticles. For example, both porfimer and motexaf in gadolinium can be incorporated into the metal-bisphosphonate nanoparticles. The resulting particles containing large payloads of porfimer and motexaf in gadolinium can be used to deliver large doses of sensitizer for PDT and X-ray radiation therapy, respectively. Efficient targeted delivery approaches can have an impact in realizing the clinical potential of PDT agents and radiosensitizers.

VII. Metal-bisphosphonate Nanoparticles for Simultaneous Delivery of a Therapeutic Agent and an Imaging Agent In some embodiments, the presently disclosed metal-bisphosphonate nanoparticles carry both therapeutic agents and imaging contrast agents (e.g., in suitable proportions). This can allow real-time monitoring of how efficiently anticancer drugs are localized in tumors after their administration, as well as how the cancer cells respond to the treatment. Such a dual therapeutic agent/imaging contrast agent delivery approach can enable physicians to determine if the drug formulation is working well on the patient, saving time if the patient does not respond, or does not respond well, to the particular treatment.

The presently disclosed metal-bisphosphonate nanoparticles can contain a large variety of contrast agents for different imaging modalities, including but not limited to MRI, optical imaging, PET, and SPECT. For example, the lanthanide atom $Gd^{3+}$ or a transition metal such as $Mn^{2+}$ can be readily incorporated into the particles. $Gd^{3+}$ and $Mn^{2+}$ are important MRI contrast agents. All of these metals, when delivered along with the anticancer drugs or prodrugs in the metal-bisphosphonate nanoparticles to the tumor sites, can allow determination of particle uptake in the tumors, as well as high-resolution delineation of the tumors as a result of the MR contrast enhancement. In addition, or alternatively, in some embodiments, an organic fluorophore (such as a near-infrared dye) that has functional groups available for coordination with metal centers can be incorporated into the metal-bisphosphonate nanoparticles for use as an optical imaging contrast agent. In some embodiments, radioactive metal centers can also be doped into the metal-bisphosphonate nanoparticles for application as contrast agents for PET (such as $^{64}Cu$) or SPECT (such as $^{111}In$, and $^{99m}Tc$) imaging. PET and SPECT imaging can be used for real-time monitoring of the biodistribution of the particles in vivo.

VIM. Post-Modification of Metal-bisphosphonate Nanoparticles with Inorganic, Organic, and Biological Moieties In some embodiments, the presently disclosed nanoparticle systems can be modified with shells (i.e., coating layers) comprising, but not limited to, inorganic compounds or polymers, such as metal-oxides, organic molecules or polymers, such as polyvinylpyrollidone, single lipid layers, lipid bilayers and/or liposomal formulations. By modifying the surface properties of the nanoparticles, they can be stabilized against dissolution under biological conditions, can be easily functionalized to impart biological stability, multimodality, and specificity, and/or can be incorporated into delivery vehicles such as liposomes. The pharmacokinetics of the metal-bisphosphonate nanoparticles can be readily tuned to maximize the anticancer therapeutic indices of these nanoparticles.

Accordingly, in some embodiments, the presently disclosed subject matter provides a metal-bisphosphonate nanoparticle comprising (a) a core comprising a multivalent metal ion-bisphosphonate complex; and (b) a coating layer surrounding at least a portion of an outer surface of the core. The coating layer can comprise, for example, a metal oxide, a polymer (e.g., a silica-based polymer or an organic polymer), a single lipid layer, or a lipid bilayer. In some embodiments, the core can further comprise a non-bisphosphonate therapeutic agent or prodrug thereof and/or an imaging agent.

In some embodiments, the multivalent metal ion of the multivalent metal ion-bisphosphonate complex is divalent. Suitable divalent ions include, but are not limited to $Ca^{2+}$, $Mg^{2+}$, $Mn^{2+}$, $Zn^{2+}$ and combinations thereof. In some embodiments, the complex comprises at least two different multivalent metal ions and/or at least one paramagnetic metal ion. In some embodiments, the complex comprises a single type of multivalent metal ion. In some embodiments, the complex is free of paramagnetic metal ions, phosphate ions, and/or platinum ions.

In some embodiments, the bisphosphonate of the multivalent metal ion-bisphosphonate complex has a structure of Formula (I):

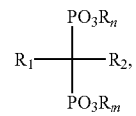

wherein n and m are each independently an integer between 0 and 2 (i.e., each independently 0, 1, or 2); each R is independently H, alkyl, substituted alkyl, aralkyl, aryl, or substituted aryl; $R_1$ is H, hydroxyl, halo, alkyl, substituted alkyl, amino, alkoxy, or alkylthio; and $R_2$ is halo, alkyl, substituted alkyl, aralkyl, substituted aralkyl, alkoxy, alkylthio, aryloxy, arylthio or arylamino; or an anion or salt thereof. In some embodiments, $R_2$ is a substituted alkyl or an aralkyl group. In some embodiments, the $R_2$ substituted alkyl group is $NH_2$-substituted alkyl, alkylamino-substituted alkyl, or dialkylamino-substituted alkyl. In some embodiments, the $R_2$ aralkyl group comprises a nitrogen-containing heteroaryl moiety. Thus, suitable bisphosphonates include, but are not limited to, zoledronic acid, pamidronate, risedronic acid, alendronate, zeridronic acid, tiludronate, etidronate, and ibandronate.

In some embodiments, the coating layer comprises a silica-based polymer, wherein said silica-based polymer is derivatized with a targeting agent and/or a passivating agent. For example, the coating layer can comprise silica, cRGfK-derivatized silica, PEG-derivatized silica, and/or anisamide-PEG-derivatized silica. In some embodiments, the nanoparticle further comprises one or more additional coating layer (i.e., a coating layer in addition to the coating layer (b)), such as, but not limited to a metal oxide, a polymer, a single lipid layer, a lipid bilayer, and combinations thereof.

IX. Functionalization of Metal-bisphosphonate Nanoparticles for Passivating and/or Targeting Purposes In some embodiments, the presently disclosed metal-bisphosphonate nanoparticles, including but not limited to those modified with a shell/coating layer or encapsulated within a single lipid layer or lipid bilayer, can be functionalized with biocompatible passivating molecules, such as polyethylene glycol, which can act by deterring the adsorption of plasma proteins and recognition by the bodies defense systems such as the reticulo-endothelial system (RES). In some embodiments, the metal-bisphosphonate nanoparticles can also be functionalized with targeting moieties that are specific for certain antigens, receptors, etc. over-expressed on the surface of cells associated with the disease (e.g., cancer). Targeting moieties include, but are not limited to, small molecules, peptides, and proteins.

In embodiments using a specific targeting or other additional moiety, the additional moiety can optionally be associated with the exterior (i.e., outer surface) of the particle. The targeting moiety can be conjugated (i.e., grafted or bonded) directly to the exterior via any useful reactive group on the exterior, such as, for example, an amine, an alcohol, a silyl ether, a carboxylate, an isocyanate, a phosphate, a thiol, a halide, or an epoxide. For example, a targeting moiety containing or derivatized to contain an amine that is not necessary for the recognition of the targeted cell or tissue can be coupled directly to a reactive group (e.g., a carboxylate) present on the particle exterior using carbodiimide chemistry. Synthetic linkers can be used to attach the targeting moiety to the nanoparticle surface, as well. For example, a synthetic linker containing a carboxylate or other suitable reactive group can be grafted onto the surface of the nanoparticle prior to conjugation to the additional moiety. Thus, a linker can be used to provide the nanoparticle surface with an appropriate reactive group for conjugation with a targeting or other moiety if a suitable reactive moiety is not provided by the chemical structure of the polymeric matrix material.

In some embodiments, a contrast agent can be bound to a targeting group that acts to direct the contrast agent to a specific tissue or cell type. Thus, the targeting group can cause the contrast agent, once introduced into a subject, to locate or concentrate in a specific organ or at cells expressing specific molecular signals, such as certain cancer cells. Suitable targeting groups include, but are not limited to, small molecules, polynucleotides, peptides, and proteins, including antibodies and antibody fragments, such as Fab's. In some embodiments, the targeting agent is an anti-major histocompatibility complex (MHC)-II antibody, which can target sites of inflammation.

In some embodiments, the targeting agent targets a tumor. Such tumor-related targeting agents can be related to various known tumor markers or to enzymes related to a particular type of tumor. Thus, tumor targeting agents can include antibodies, antibody fragments, cell surface receptor ligands, and the like. Further targeting agents are discussed hereinbelow.

Targeting moieties for use in targeting cancer cells can be designed around tumor specific antigens including, but not limited to, carcinoembryonic antigen, prostate specific antigen, tyrosinase, ras, HER2, erb, MAGE-1, MAGE-3, BAGE, MN, gp100, gp75, p97, proteinase 3, a mucin, CD81, CID9, CD63; CD53, CD38, CO-029, CA125, GD2, GM2 and O-acetyl GD3, M-TAA, M-fetal or M-urinary find use with the presently disclosed subject matter. Alternatively the targeting moiety can be designed around a tumor suppressor, a cytokine, a chemokine, a tumor specific receptor ligand, a receptor, an inducer of apoptosis, or a differentiating agent. Further, given the importance of the angiogenesis process to the growth of tumors, in some embodiments, the targeting moiety can be developed to target a factor associated with angiogenesis. Thus, the targeting moiety can be designed to interact with known angiogenesis factors such as vascular endothelial growth factor (VEGF). See Brannon-Peppas, L. and Blanchette, J. O., *Advanced Drug Delivery Reviews*, 56, 1649-1659 (2004).

Tumor suppressor proteins provided for targeting include, but are not limited to, p16, p21, p27, p53, p73, Rb, Wilms tumor (WT-1), DCC, neurofibromatosis type 1 (NF-1), von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pan-carcinoma antigen, ovarian carcinoma antigen (CA125), prostate specific antigen, melanoma antigen gp75, CD9, CD63, CD53, CD37, R2, CD81, CO029, TI-1, L6 and SAS. Of course these are merely exemplary tumor suppressors and it is envisioned that the presently disclosed subject matter can be used in conjunction with any other agent that is or becomes known to those of skill in the art as a tumor suppressor.

In some embodiments, targeting is directed to factors expressed by an oncogene. These include, but are not limited to, tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bcl-2 and family members.

Cytokines that can be targeted by the presently disclosed particles include, but are not limited to, IL-1, IL-2, IL-3, IL-4, IL-5, IL-6, IL-7, IL-8, IL-9, IL-10, ILA 1, IL-12, IL-13, IL-14, IL-15, TNF, GM-CSF, β-interferon and γ-interferon. Chemokines that can be used include, but are not limited to, M1P1α, M1P1β, and RANTES.

Enzymes that can be targeted include, but are not limited to, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, and human thymidine kinase.

Receptors and their related ligands that find use in the context of the presently disclosed subject matter include, but are not limited to, the folate receptor, adrenergic receptor, growth hormone receptor, luteinizing hormone receptor, estrogen receptor, epidermal growth factor(EGF) receptor, fibroblast growth factor receptor (FGFR), and the like. For example, EGF is overexpressed in brain tumor cells and in breast and colon cancer cells. In some embodiments, the targeting moiety is selected from the group consisting of folic acid, guanidine, transferrin, carbohydrates and sugars. In some embodiments, the targeting moiety is a peptide selected from the group consisting of the amino acid sequence RGD and TAT peptides.

Hormones and their receptors include, but are not limited to, growth hormone, prolactin, placental lactogen, luteinizing hormone, foilicle-stimulating hormone, chorionic gonadotropin, thyroid-stimulating hormone, leptin, adrenocorticotropin (ACTH), angiotensin I, angiotensin II, β-endorphin, β-melanocyte stimulating hormone (β-MSH), cholecystokinin, endothelin I, galanin, gastric inhibitory peptide (GIP), glucagon, insulin, amylin, lipotropins, GLP-1 (7-37) neurophysins, and somatostatin.

The presently disclosed subject matter provides that vitamins (both fat soluble and non-fat soluble vitamins) placed in the targeting component of the nanomaterials can be used to target cells that have receptors for, or otherwise take up these vitamins. Particularly preferred for this aspect are the fat soluble vitamins, such as vitamin D and its analogues, Vitamin E, Vitamin A, and the like or water soluble vitamins such as Vitamin C, and the like.

Antibodies can be generated to allow for the targeting of antigens or immunogens (e.g., tumor, tissue or pathogen specific antigens) on various biological targets (e.g., pathogens, tumor cells, and normal tissue). In some embodiments of the presently disclosed subject matter, the targeting moiety is an antibody or an antigen binding fragment of an antibody (e.g., Fab, F(ab')2, or scFV units). Thus, "antibodies" include, but are not limited to polyclonal antibodies, monoclonal antibodies, chimeric antibodies, single chain antibodies, Fab fragments, and a Fab expression library.

Other characteristics of the nanoparticle also can be used for targeting. Thus, in some embodiments, the enhanced permeability and retention (EPR) effect is used in targeting. The EPR effect is the selective concentration of macromolecules and small particles in the tumor microenvironment, caused by the hyperpermeable vasculature and poor lymphatic drainage of tumors. To enhance EPR, in some embodiments, the exterior of the particle can be coated with or conjugated to a hydrophilic polymer to enhance the circulation half-life of the particle and to discourage the attachment of plasma proteins to the particle.

For additional exemplary strategies for targeted drug delivery, in particular, targeted systems for cancer therapy, see Brannon-Peppas, L. and Blanchette, J. O., *Advanced Drug Delivery Reviews*, 56, 1649-1659 (2004) and U.S. Pat. No. 6,471,968, each of which is incorporated herein by reference in its entirety.

X. Metal-bisphosphonate Nanoparticles for Treatment and Imaging of Bone Resorption-Related Diseases In some embodiments, as a result of their enhanced pharmacokinetics, the presently disclosed metal-bisphosphonate nanoparticles can be used as inhibitors of bone resorption. They can thus be used to treat bone-resorption related diseases, osteoporosis, Paget's disease, and bone metastases. The bisphosphonate nanoparticles can also provide a novel vehicles for delivering imaging agents, including but not limited to $^{99m}$Tc for SPECT imaging of bone diseases (such as bone metastases of various cancers).

XI. Metal-Metal Bisphosphate Complex Nanoparticles

In some embodiments, the presently disclosed subject matter provides a metal bisphosphonate nanoparticle wherein the bisphosphonate is itself a metal complex. Thus, in some embodiments, the nanoparticle core comprises a material (e.g., a coordination complex) formed between a multivalent metal ion and bisphosphonate wherein the bisphosphonate is a metal bisphosphonate complex. Accordingly, in some embodiments, the bisphosphonate is metal complex wherein two metal ligands are phosphonate-containing groups and wherein the phosphonate groups are available for coordinating to the multivalent metal ion. For example, bisphosphonates can be prepared by providing a suitable metal complex, such as a metal complex with two hydroxyl ligands, and contacting the metal complex with diethoxyphosphinyl isocyanate, diethoxyphosphinyl isothiocyanate, diethoxyphosphinyl-containing carboxylic anhydride, or diethoxyphosphinyl-containing acyl chloride to form metal ligands that can provide phosphonate groups available for further coordinative bonding. In some embodiments, the bisphosphonate is a platinum metal complex (e.g., cisplatin, oxaliplatin, or a similar complex) wherein two platinum ligands have been replaced by or conjugated to phosphonate-containing groups that are not involved in coordinating to the platinum.

In some embodiments, the metal-metal bisphosphonate complex nanoparticles can be provided by mixing a multivalent metal ion precursor with a metal bisphosphonate complex in one or more microemulsions. Microemulsions, particularly, water-in-oil, or reverse, microemulsions have been used to synthesize a variety of nanophase materials such as organic polymers, semiconductor nanoparticles (see Xu and Akins, *Material. Letters*, 58, 2623 (2004)), metal oxides, and nanocrystals consisting of cyanide-bridged transition metal ions. See Vaucher et al. *Angew. Chem. Int. Ed.*, 39, 1793 (2000); Vaucher et al., *Nano Lett.*, 2, 225 (2002); Uemura and Kitagawa, *J. Am. Chem. Soc.*, 125, 7814 (2003); Catala et al., *Adv. Mater.*, 15, 826 (2003); and Yamada et al., *J. Am. Chem. Soc.*, 126, 9482 (2004). Reverse microemulsions comprise nanometer scale water droplets stabilized in an organic phase by a surfactant, which can be anionic, cationic, or neutral in charge. Numerous reports on the physical properties of microemulsion systems suggest the water to surfactant ratio, referred to as the W value (i.e., $[H_2O]/[surfactant]$), largely dictates the size of the reverse micelle, which is just one of many tunable properties microemulsions offer. See Worm et al., *J. Am. Chem. Soc.*, 98, 2391 (1976); White et al., *Langmuir*, 21, 2721 (2005); Giustini et al., *J. Phys. Chem.*, 100, 3190 (1996); and Kumar and Mittal, eds., *Handbook of Microemulsion Science and Technology*; New York: Marcel Decker, 1999. For a description of the use of microemulsions in preparing silica-coated nanoparticles, see U.S. Patent Application Publication No. 20060228554, which is incorporated herein by reference in its entirety.

The immiscible liquids that can be used to make a microemulsion typically include a relatively polar (i.e., hydrophobic) liquid and a relative non-polar (i.e., hydrophillic) liquid. While a large variety of polar/non-polar liquid mixtures can be used to form a microemulsion useful in the presently disclosed subject matter, the choice of particular liquids utilized can depend on the type of nanoparticles being made. Upon a review of the instant disclosure, a skilled artisan can select specific liquids for particular applications by adapting known methods of making microemulsions for use in the presently disclosed methods. In many embodiments, the relatively polar liquid is water, although other polar liquids might also be useful. Water is useful because it is inexpensive, readily available, non-toxic, easy to handle and store, compatible with a large number of different precipitation reactions, and immiscible in a large number of non-polar solvents. Examples of suitable non-polar liquids include alkanes (e.g., any liquid form of hexane, heptane, octane, nonane, decane, undecane, dodecane, etc.), cycloalkanes (e.g., cyclopentane, cyclohexane, etc.), aromatic hydrocarbons (e.g., benzene, toluene, etc.), and mixtures of the foregoing (e.g., petroleum and petroleum derivatives). In general, any such non-polar liquid can be used as long as it is compatible with the other components used to form the microemulsion and does not interfere with any precipitation reaction used to isolate the particles after their preparation.

Generally, at least one surfactant is needed to form a microemulsion. Surfactants are surface active agents that thermodynamically stabilize the very small dispersed micelles or reverse micelles in microemulsions. Typically, surfactants possess an amphipathic structure that allows them to form films with very low interfacial tension between the oily and aqueous phases. Thus, any substance that reduces surface tension at the interface of the relatively polar and relatively non-polar liquids and is compatible with other aspects of the presently disclosed subject matter can be used to form the microemulsion used to make nanoparticles. The choice of a surfactant can depend on the particular liquids utilized and on the type of nanoparticles being made. Specific surfactants suitable for particular applications can be selected from known methods of making microemulsions or known characteristics of surfactants. For example, non-ionic surfactants are generally preferred when an ionic reactant is used in the microemulsion process and an ionic detergent would bind to or otherwise interfere with the ionic reactant.

Numerous suitable surfactants are known. A nonexhaustive list includes soaps such as potassium oleate, sodium oleate, etc.; anionic detergents such as sodium cholate, sodium caprylate, etc.; cationic detergents such as cetylpyridynium chloride, alkyltrimethylammonium bromides, benzalkonium chloride, cetyldimethylethylammonium bromide, etc; zwitterionic detergents such as N-alkyl-N,N-dimethylammonio-1-propanesulfonates and CHAPS; and non-ionic detergents such as polyoxyethylene esters, and various tritons (e.g., (TRITON™-X100, TRITON™-X114); etc.

The concentration of surfactant used can depend on many factors including the particular surfactant selected, liquids used, and the type of nanoparticles to be made. Suitable concentrations can be determined empirically; i.e., by trying different concentrations of surfactant until the concentration that performs best in a particular application is found. Ranges of suitable concentrations can also be determined from known critical micelle concentrations.

In some embodiments, the microemulsion or microemulsions can contain a lipid compound, such as but not limited to DOPA, DOTAP, DOPC, or DOPE so that the nanoparticle further comprises a lipid coating layer (e.g., a single lipid layer) over at least a portion of the outer surface of the nanoparticle.

In some embodiments, the metal-metal bisphosphonate complex can be coated with more than one coating layer or agent (e.g., in addition to any lipid coating that is provided during synthesis of the nanoparticle). Such additional coating layers include, but are not limited to a metal oxide, a polymer (e.g., a silica-based polymer or an organic polymer), a single lipid layer, or a lipid bilayer. The nanoparticles can be enclosed in liposomes. In some embodiments, one or more of the coating layers or agents can comprise a targeting or passivating agent. In some embodiments, the metal-metal bisphosphonate complex can further include one or more additional therapeutic agents, prodrugs and/or imaging contrast agents (e.g., in addition to the bisphosphonate complex).

Accordingly, in some embodiments, the presently disclosed subject matter provides a metal-bisphosphonate nanoparticle comprising a core comprising: (a) $M_1$, wherein $M_1$ is a multivalent metal ion; and (b) a bisphosphonate, wherein the bisphosphonate comprises a metal complex having the formula $M_2L_x$, wherein x is an integer of 2 or greater, $M_2$ is a second metal ion, each L is a metal ion ligand, and wherein at least two L comprise a phosphonate group. In some embodiments, $M_1$ is a divalent metal ion, such as, but not limited to, $Ca^{2+}$, $Mg^{2+}$, $Mn^{2+}$, $Zn^{2+}$ or combinations thereof. In some embodiments, $M_1$ is $Zn^{2+}$.

In some embodiments, $M_2$ is a platinum ion, a ruthenium ion, or any beta-emitting radionuclide such as $^{99}Y$. In some embodiments, x is 5 or 6. The two L ligands that comprise a phosphonate group can have the formula —O—C(=O)—NH—P(=O)(OR)$_2$, wherein each R is independently H, alkyl, substituted alkyl, aralkyl, aryl, substituted aryl, or a negative charge. In some embodiments, each R is H, alkyl or a negative charge. In some embodiments, each R is H or a negative charge. The other L ligands (i.e., those that do not contain a phosphonate group) can include mono- and bidentate metal ligands, such as, but not limited to, halo (e.g., Cl, Br, F, or I), $NH_3$, alkylamino, hydroxyl, alkoxy, diols and diamines (e.g., diaminocyclohexane). In some embodiments, the bisphosphonate can have the formula $M_2L_{x-2}$[-O—C(=O)—NH—P(=O)(OR)$_2$]$_2$. In some embodiments, the nanoparticle core can comprise a coordination complex formed between $M_1$ and the complex having the formula $M_2L_{x-2}$[-O—C(=O)—NH—P(=O)(OR)$_2$]$_2$.

In some embodiments, the nanoparticle further comprises one or more coating agents or layers surrounding at least a portion of an outer surface of the core. The coating agents or layers can include, for example, metal oxide, polymers (e.g., silica-based polymers or organic polymers), single lipid layers, lipid bilayers or combinations thereof. In some embodiments, the nanoparticle comprises at least one lipid coating layer or agent (e.g., a single lipid layer). In some embodiments, the one or more coating agents or layer can comprise a targeting moiety or a passivating moiety. In some embodiments, the nanoparticle can further comprise a non-bisphosphonate therapeutic agent or prodrug thereof and/or an imaging agent.

XII. Formulations

The compositions of the presently disclosed subject matter comprise in some embodiments a composition that includes a pharmaceutically acceptable carrier. Any suitable pharmaceutical formulation can be used to prepare the compositions for administration to a subject. In some embodiments, the composition and/or carriers can be pharmaceutically acceptable in humans.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above, the formulations of this presently disclosed subject matter can include other agents conventional in the art having regard to the type of formulation in question. For example, sterile pyrogen-free aqueous and non-aqueous solutions can be used.

XIII. Subjects

The methods and compositions disclosed herein can be used on a sample either in vitro (for example, on isolated cells or tissues) or in vivo in a subject (i.e. living organism, such as a patient). In some embodiments, the subject is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided is imaging methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the imaging of birds, including the imaging of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the imaging of livestock including, but not limited to domesticated swine (pigs and hogs), ruminants, horses, poultry, and the like.

XIV. Administration

Suitable methods for administration of a composition of the presently disclosed subject matter include, but are not limited to intravenous and intratumoral injection, oral administration, subcutaneous administration or i.p. administration. Alternatively, a composition can be deposited at a site in need of imaging in any other manner, for example by spraying a composition comprising a composition within the pulmonary pathways. The particular mode of administering a composition of the presently disclosed subject matter depends on various factors, including the distribution and abundance of cells to be imaged and/or treated and mechanisms for metabolism or removal of the composition from its site of administration. For example, relatively superficial tumors can be injected intratumorally. By contrast, internal tumors can be imaged and/or treated following intravenous injection.

In one embodiment, the method of administration encompasses features for regionalized delivery or accumulation at the site to be imaged and/or treated. In some embodiments, a composition is delivered intratumorally. In some embodiments, selective delivery of a composition to a target is accomplished by intravenous injection of the composition followed by hyperthermia treatment of the target.

For delivery of compositions to pulmonary pathways, compositions of the presently disclosed subject matter can be formulated as an aerosol or coarse spray. Methods for preparation and administration of aerosol or spray formulations can be found, for example, in U.S. Pat. Nos. 5,858,784; 6,013,638; 6,022,737; and 6,136,295.

XV. Doses

An effective dose of a composition of the presently disclosed subject matter is administered to a subject. An "effective amount" is an amount of the composition sufficient to produce detectable treatment or adequate imaging. Actual dosage levels of constituents of the compositions of the presently disclosed subject matter can be varied so as to administer an amount of the composition that is effective to achieve the desired effect for a particular subject and/or target. The selected dosage level can depend upon the activity (e.g., MRI relaxivity or bisphosphonate drug loading) of the composition and the route of administration.

After review of the disclosure herein of the presently disclosed subject matter, one of ordinary skill in the art can tailor the dosages to an individual subject, taking into account the particular formulation, method of administration to be used with the composition, and nature of the target to be imaged and/or treated. Such adjustments or variations, as well as evaluation of when and how to make such adjustments or variations, are well known to those of ordinary skill in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods

All of the starting materials were purchased from Sigma Aldrich (St. Louis, Mo., United States of America) or Fisher (Thermo Fisher Scientific, Hampton, N.H., United States of America) unless otherwise noted, and used without further purification. 1,2-dioleoyl-3-trimethylammonium-propane, chloride salt (DOTAP), 1,2-dioleoyl-sn-glycero-3-phosphocholine (DOPC), 1,2-dioleoyl-sn-glycero-3-phosphate sodium salt (DOPA), and 1,2-distearoyl-sn-glycero-3-phosphoethanolamine-N-[amino(polyethylene glycol)2000] (DSPE-PEG$_{2k}$) were purchased from Avanti Polar Lipids (Alabaster, Ala., United States of America). L-α-phosphatidylethanolamine, dioleoyl (DOPE) was a gift from Sigma Aldrich (St. Louis, Mo., United States of America). Cell culture supplies were commercially available as follows: fetal bovine serum (FBS, Sigma, St. Louis, Mo., United States of America), GIBCO™ RPMI-1640 growth medium (Invitrogen Corporation, Carlsbad, Calif.), penicillin-streptomycin (Sigma, St. Louis, Mo., United States of America), and phosphate buffered saline (PDS, GIBCO™, Invitrogen Corporation, Carlsbad, Calif., United States of America). Microwave reactions were carried out in a CEM Discovery microwave (Matthews, N.C., United States of America). The $^1$H NMR spectra were recorded on a Bruker NMR 400 DRX Spectrometer (Bruker Corporation, Billerica, Mass., United States of America) at 400 MHz and referenced to the proton resonance resulting from incomplete deuteration of deuterated chloroform or DMSO. Single-crystal X-ray diffraction and Powder X-ray diffraction (PXRD) patterns were collected on a Bruker SMART APEX II diffractometer (Bruker AXS, Inc., Madison, Wis., United States of America) using Cu radiation. The PXRD patterns were processed with the APEX II package using PILOT plug-in. UV-Vis absorption spectra were obtained using a Shimadzu UV-2401 PC UV-Vis Spectrophotometer (Shimadzu Corporation, Kyoto, Japan). Thermogravimetric analyses (TGA) were performed using a Shimadzu TGA-50 (Shimadzu Corporation, Kyoto, Japan) equipped with a platinum pan. A Hitachi 4700 field emission scanning electron microscope (SEM; Hitachi Intruments, Ltd., Tokyo, Japan) and a JEM 100CX-II transmission electron microscope (JEOL Ltd., Tokyo, Japan) were used to determine particle size and morphology. SEM images of the nanoparticles were taken on glass substrate. A Cressington 108 Auto Sputter Coater (Cressington Scientific Instruments, Ltd., Watford, United Kingdom) equipped with a Au/Pd (80/20) target and MTM-10 thickness monitor was used to coat the sample with approximately 5 nm of conductive layer before taking SEM images. Size and zeta potential data were collected with a Malvern Zetasizer Nano Zs (Malvern Instruments, Malvern, United Kingdom). A Varian 820-MS Inductively Coupled Plasma-Mass Spectrometer (Varian, Inc., Palo Alto, Calif., United States of America) was used to determine Mn and Pt concentration. Samples were introduced via a concentric glass nebulizer with a free aspiration rate of 0.4 mL/min, a Peltier-cooled double pass glass spraychamber, and a quartz torch. A peristaltic pump carried samples from a SPS3 autosampler (Varian Inc., Palo Alto, Calif., United States of America) to the nebulizer. All standards and samples were in 2% $HNO_3$, prepared with milliQ water.

Example 1

Crystalline Calcium Pamidronate (Ca-Pam) and Calcium Zoledronate (Ca-Zol) Nanoparticles 1.1. Ca-Pam nanoparticle Synthesis. Pamidronic acid (0.1 g, 0.42 mmol) and $CaCl_2 \cdot 2H_2O$ (0.2 g, 1.4 mmol) were dissolved in 14 mL water and adjusted to a pH value of 8.2 respectively. The combined solution was further stirred for 24 h at 80° C. Ca-Pam was isolated via centrifuge at 13000 rpm for 15 min. Before re-dispersing them in EtOH, they were washed once with water and three times with EtOH. Approximately 81 mg (70%) particles of Ca-Pam were isolated from this procedure.

1.2. Ca-Zol nanoparticle synthesis. Zoledronic acid (5 mg, 0.019 mmol) and $CaCl_2 \cdot 2H_2O$ (10 mg, 0.07 mmol) were dissolved in a solvent mixture of $DMF/H_2O$ (5 mL/2 mL). The resulting solution was sealed in a microwave vessel and placed in the microwave oven with the power set to 400 W and run time set to 5 minutes. After 20 minutes of heating at 100° C. with stirring, the crystalline particles of Ca-Zol were isolated via centrifuge at 13000 rpm for 15 min. Before re-dispersing them in EtOH, they were washed once with water and three times with EtOH. Approximately 4 mg (67.5%) particles of Ca-Zol were isolated from this procedure.

1.3. Ca-Pam and Ca-Zol single crystal X-ray structures. The single crystals of Ca-Pam and Ca-Zol were grown for X-ray diffraction studies. All crystallographic measurements were made on a Bruker SMART Apex II CCD-based X-ray diffractometer system (Bruker AXS, Inc., Madison, Wis., United States of America) equipped with Cu-target X-ray tube and operated at 1600 watts. The frames were integrated with the Bruker SAINT© build in APEX II software package using a narrow-frame integration algorithm, which also corrects for the Lorentz and polarization effects. Absorption corrections were applied using SADABS (Bruker AXS, Inc., Madison, Wis., United States of America). All of the structures were solved by direct methods and refined to convergence by least squares method on $F^2$ using the SHELXTL software suit (Bruker AXS, Inc., Madison, Wis., United States of America). All non-hydrogen atoms are refined anisotropically. Datasets for Ca-Pam and Ca-Zol were collected to 2θ=138.6° and 108.1° respectively, with >98% completeness. X-ray crystallographic data for the Ca-Pam and Ca-Zol nanoparticles described in Table 1 below. FIGS. 2A-2D show packing diagrams for the nanoparticles.

TABLE 1

X-Ray crystallograohic data for Ca-Pam and Ca-Zol

| Compound | Ca-Pam | Ca-Zol |
|---|---|---|
| Empirical formula | C3 H7 Ca N O9 P2 | C5 H6 Ca N2 O8 P2 |
| Formula weight | 303.12 | 324.14 |
| Temperature (K) | 100(2) | 100(2) |
| Wavelength (Å) | 1.54178 | 1.54178 |
| Crystal system | Orthorhombic | Orthorhombic |
| Space group | Pna21 | Pna21 |
| Unit cell dimensions | a = 13.7486(3) Å<br>b = 10.6087(2) Å<br>c = 6.9230(2) Å<br>α = 90°<br>β = 90°<br>γ = 90° | a = 13.4828(9 Å<br>b = 12.6963(7) Å<br>c = 6.7635(5) Å<br>α = 90°<br>β = 90°<br>γ = 90° |
| Volume (Å$^3$) | 34097(6) | 35784(21) |
| Z | 4 | 4 |
| Density (calcd. g/cm$^3$) | 1.994 | 1.860 |
| Absorption coeff. (mm$^{-1}$) | 8.811 | 7.701 |
| F(000) | 616 | 4056 |
| Crystal size (mm) | 1.00 × 0.02 × 0.02 | 0.1 × 0.01 × 0.01 |
| Crystal color & shape | Colorless | colorless |
| θ range data collection | 5.27 to 69.30° | 4.78 to 54.06° |
| Limiting indices | −15 < h < 16<br>−12 < k < 12<br>−7 < l < 5 | −13 < h < 13<br>−13 < k < 12<br>−5 < l < 7 |
| Reflections collected | 3572 | 4056 |
| Independent reflections | 1472 [R(int) = 0.0249] | 1107 [R(int) = 0.0841] |
| Refinement method | Full-matrix least-square on F$^2$ | Full-matrix least-square on F$^2$ |
| Data/restraints/parameters | 1472/1/146 | 1107/8/164 |
| Goodness-of-fit on F$^2$ | 1.108 | 1.087 |
| Final R indices [I > 2σ(I)]$^{a,b}$ | R1 = 0.0360<br>wR2 = 0.0960 | R1 = 0.0586<br>wR2 = 0.1434 |
| R indices (all data) | R1 = 0.0369<br>wR2 = 0.0966 | R1 = 0.0776<br>wR2 = 0.1518 |

$^a$R(F) = Σ||F$_o$| − |F$_c$||/Σ|F$_o$|.
$^b$Rw(F$_c^2$) = [Σ{w(F$_o^2$ − F$_c^2$)$^2$}/Σ{w(F$_o^2$)$^2$}]$^{0.5}$; w$^{-1}$ = σ$^2$(F$_o^2$) + (aP)$^2$ + bP, where P = [F$_o^2$ + 2F$_c^2$]/3 and a and b are constants adjusted by the program.

1.4. Procedures for the Synthesis of DOPE-anisamide. DOPE (50 mg, 0.067 mmol) was reacted with 4-methoxybenzoic acid (103.5 mg, 0.672 mmol) in dichloromethane (10 mL, anhydrous) and in the presence of N,N'-Dicyclohexylcarbodiimide (27.2 mg, 0.134 mmol) and 4-Dimethylaminopyridine (16.42 mg, 0.134 mmol) under nitrogen protection. The reaction was stirred at room temperature for 24 hrs in the dark. After the removal of dichloromethane by rotorary evaporation, the crude product was redissolved in chloroform, and the solution was washed with 4% $Na_2CO_3$, 0.2M aq. HCl, water, and then dried over $MgSO_4$. The resulting crude product was purified by column chromatography using silica gel and 5:1 chloroform to methanol as the eluent. The product was obtained after removal of the solvents (30 mg, 51% yield). 1H NMR (CDCl$_3$): δ 7.82 (d, J=7.6 Hz, 2H); 6.78 (s, 2H); 5.31 (m, 4H); 3.76 (s, 3H); 2.15

(s, 4); 1.97 (s, 6H); 1.62 (s, 10H); 1.46 (s, 4H); 1.21 (t, J=14 Hz, 30H); 0.85 (t, J=6 Hz, 6H).

1.5. General procedures for making liposomes and anisamide targeted liposomes. After the addition of 5 mg DOTAP (chloroform solution) and 5.295 mg DOPE (chloroform solution) or 1.03 mg DOPE-AA and 4.3 mg DOPE to a 20 mL vial, the solvent was removed by rotary evaporator. The lipid film was further dried under vacuum for another 3 h. To prepare liposomes, 2.85 mL water was added and the lipid was allowed to hydrate for 1 h, forming a cloudy lipid suspension. The suspension was extruded with an extruder. Membranes with pore diameter of 600 nm and 100 nm were used and at least ten extrusion cycles were performed. The resulting liposomes were stored at 4° C.

1.6. General procedures of lipid coating. Lipid coated particles were obtained by mixing an aqueous suspension of particles and the as-prepared liposomes with a weight ratio of 8:1. The mixture was allowed to sit at room temperature for 1 h with occasional shaking. Extra lipids were removed by centrifugation of the mixture at 6000 rpm for 8 mins and removal of the supernatant.

Figure 3B:
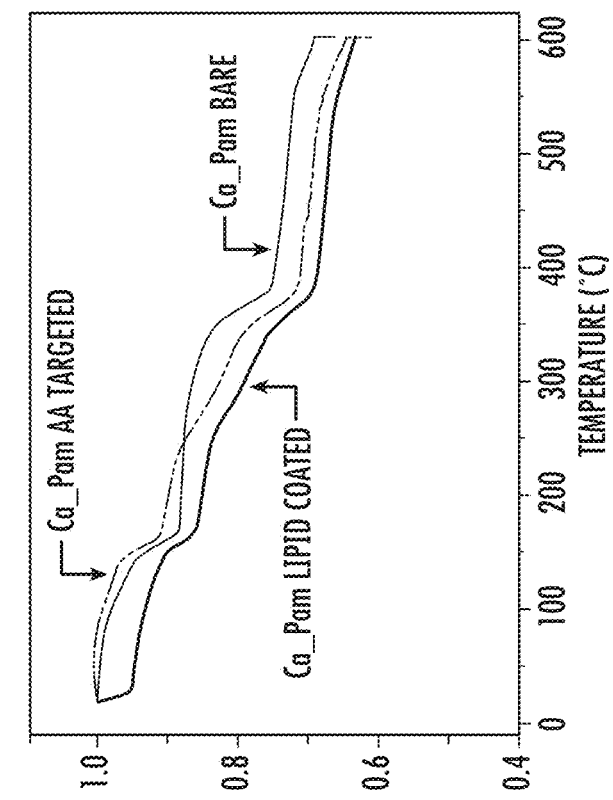
FIG. 3B is a graph showing the thermogravimetric analysis (TGA) curves of as synthesized (bare), lipid coated, and anisamide (AA) targeted crystalline calcium pamidronate (Ca-Pam) nanoparticles.
Figure 3A:
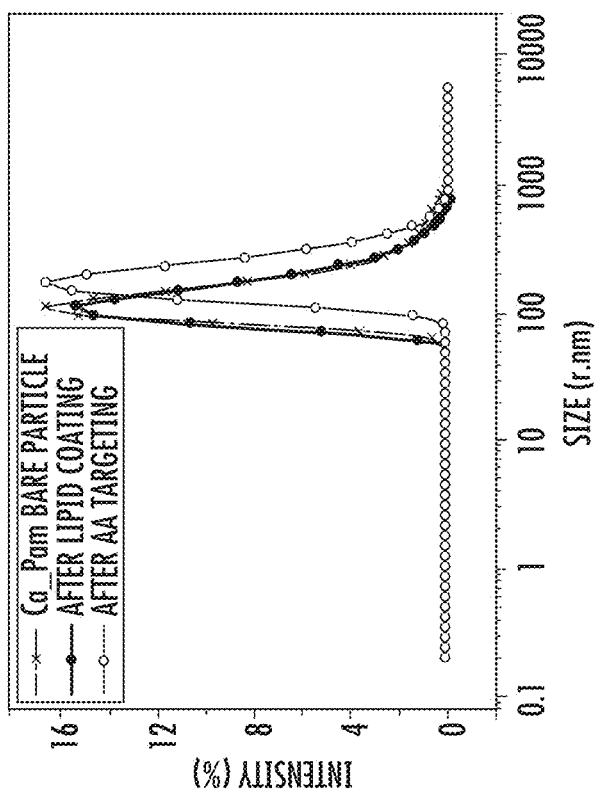
FIG. 3A is a graph showing the dynamic light scattering (DLS) hydrodynamic diameters of crystalline calcium pamidronate (Ca-Pam) nanoparticles. Data for the as-synthesized Ca-Pam nanoparticles (Ca-Pam bare particle) is shown with x's; data for the Ca-Pam nanoparticles after lipid coating is shown in solid circles; and data for the Ca-Pam nanoparticles after anisamide (AA) targeting is shown in open circles
Figure 4:
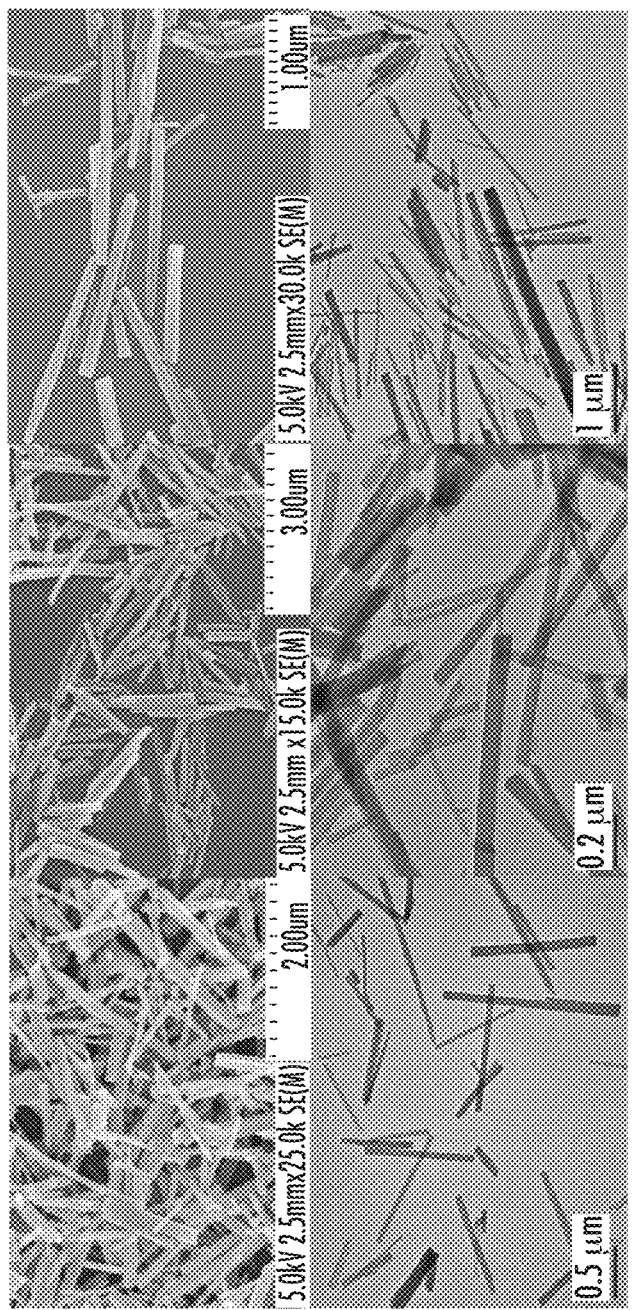
FIG. 4 as a set of scanning electron microscopy (SEM) images (top trio) and transmission electron microscopy (TEM) images (bottom trio) of crystalline calcium pamidronate (Ca-Pam) nanoparticles. The left-hand image of each trio is for as-synthesized (bare) Ca-Pam nanoparticles, the middle image of each trio is for lipid-coated Ca-Pam particles, and the right-hand image of each trio is for anisamide-targeted Ca-Pam particles.
Figure 5B:
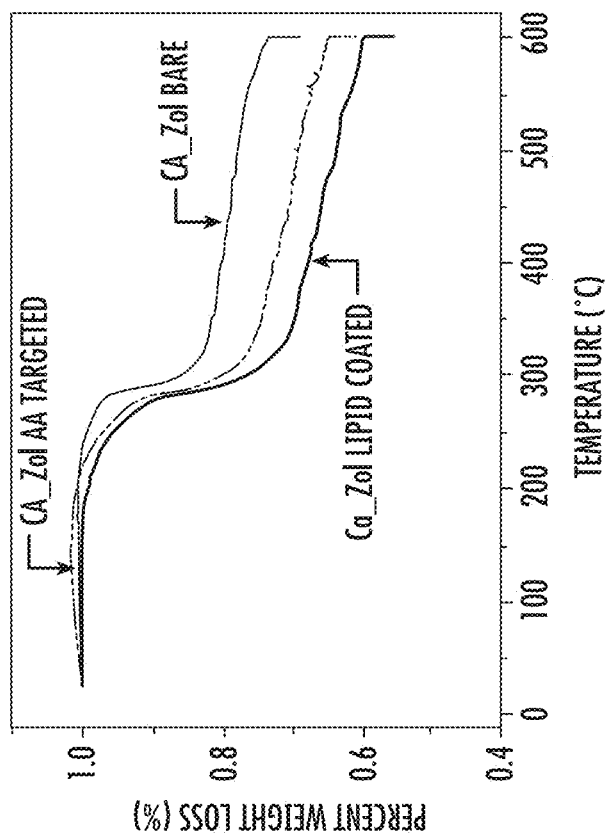
FIG. 5B is a graph of the thermogravimetric analysis (TGA) curves of as synthesized (bare) crystalline calcium zoledronate (Ca-Zol) nanoparticles, of lipid coated crystalline Ca-Zol nanoparticles, and of anisamide (AA) targeted crystalline Ca-Zol nanoparticles.
Figure 5A:
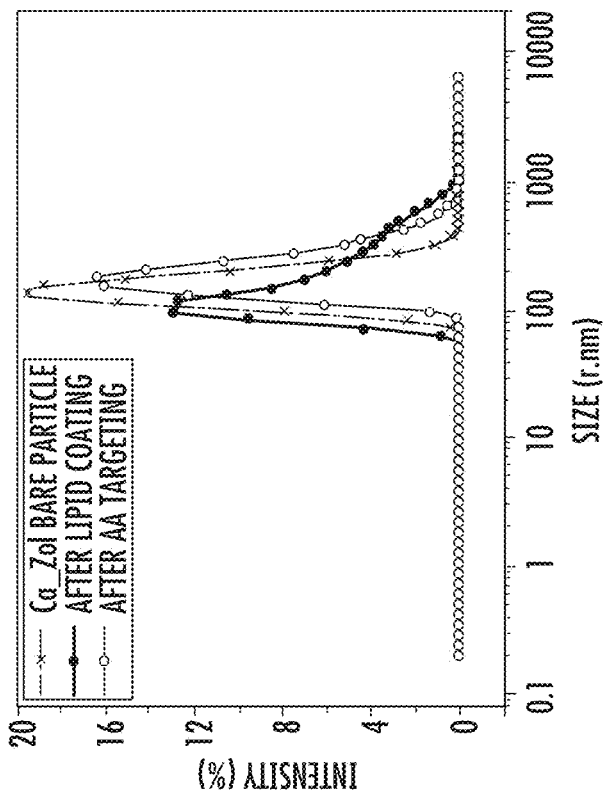
FIG. 5A is a graph of the dynamic light scattering (DLS) hydrodynamic diameters of crystalline calcium zoledronate (Ca-Zol) nanoparticles. Data for the as-synthesized Ca-Zol nanoparticles (Ca-Zol bare particle) is shown in x's; data for the Ca-Zol nanoparticles after lipid coating is shown in solid circles; and data for the Ca-Zol nanoparticles after anisamide targeting is shown in open circles.
Figure 6:
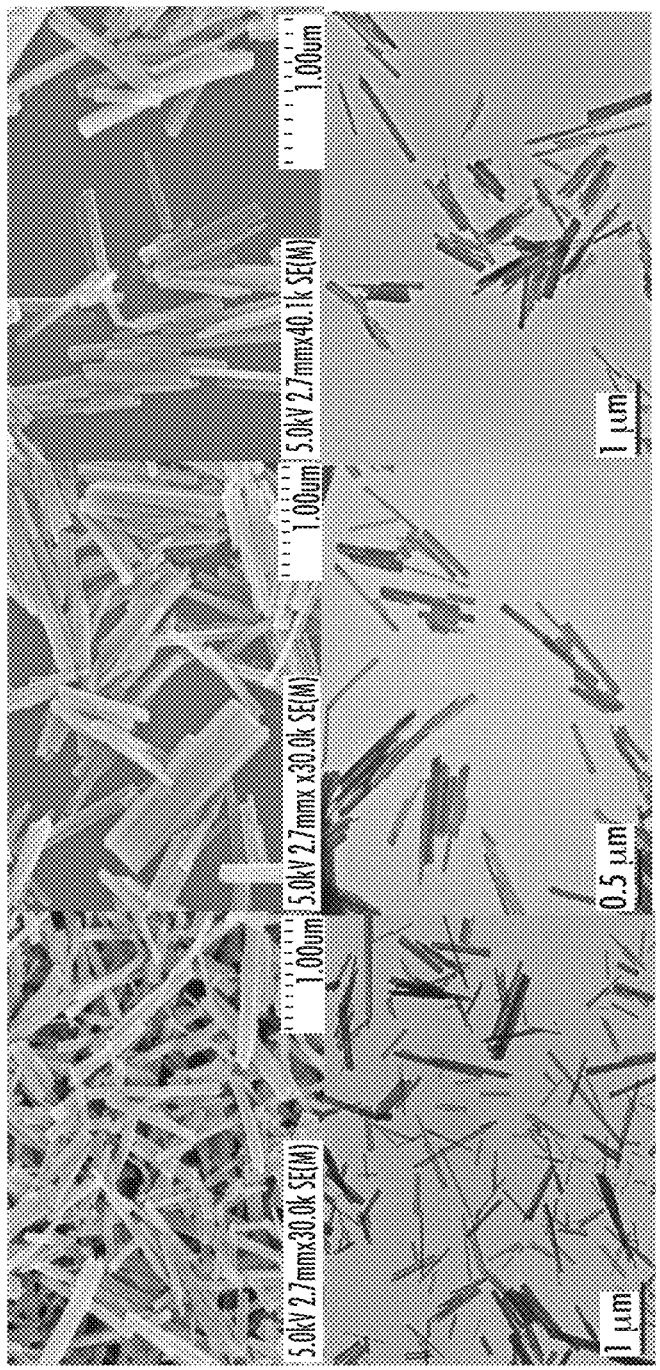
FIG. 6 is a set of scanning electron microscopy (SEM) images (top trio) and transmission electron microscopy (TEM) images (bottom trio) of crystalline calcium zoledronate (Ca-Zol) particles. The left-hand image of each trio is for as-synthesized Ca-Zol nanoparticles, the middle image of each trio is for lipid-coated Ca-Zol nanoparticles, and the right-hand image of each trio is for anisamide-targeted Ca-Zol nanoparticles.

Dynamic light scattering (DLS) data for the Ca-Pam and Ca-Zol particles is provided in Tables 2 and 3, below. FIGS. 3A and 5A show the DLS hydrodynamic diameters of bare, lipid-coated, and anisamide (AA)-targeted Ca-Pam and Ca-Zol particles, respectively. TGA curves for the various Ca-Pam and Ca-Zol particles are shown in FIGS. 3B and 5B. SEM and TEM images of the various Ca-Pam and Ca-Zol particles are shown in FIGS. 4 and 6.

TABLE 2

DLS hydrodynamic diameters and zeta potentials of the Ca-Pam nanoparticles

| Ca-Pam | Z-Ave diameter (nm) | PDI | Zeta Potential (mV) |
| --- | --- | --- | --- |
| Bare | 216.9 ± 8 | 0.254 | −22.1 ± 2 |
| Lipid coated | 195.2 ± 6 | 0.211 | 26.4 ± 6 |
| AA targeted | 242.5 ± 10 | 0.175 | 23.4 ± 6 |

TABLE 3

DLS hydrodynamic diameters and zeta potentials of the Ca-Zol nanoparticles

| Ca-Zol | Z-Ave diameter (nm) | PDI | Zeta Potential (mV) |
| --- | --- | --- | --- |
| Bare | 196.2 ± 9 | 0.266 | −32.5 ± 2 |
| Lipid coated | 273.0 ± 12 | 0.268 | 26.9 ± 4 |
| AA targeted | 258.4 ± 10 | 0.222 | 24.9 ± 3 |

1.7. Determination of Drug Loading and Release Profile for Ca-Pam. A fresh 5 mM Fe(III) chloride solution was prepared. 17.2 mL of 11.7 M perchloric acid was diluted with 50 mL water in a 100 mL volumetric flask. Then, 0.135 g ferric chloride hexahydrate was added and the solution was diluted to 100 mL with water. A fresh 2M perchloric acid was prepared. 17.2 mL of 11.7 M perchloric acid was diluted to 100 mL with water. A fresh 5 mM pamidronate in 2M perchloric acid solution was prepared. 13.95 mg pamidronate was dissolved in 10 mL 2M $HClO_4$. Using the above solutions, standard solutions were prepared. Baseline spectrum was recorded using 2.5 mM $Fe^{3+}$ in 2 M perchloric acid (with 2.5 mM PBS). The absorbances at 280 nm were recorded. Particles were digested with 2 M perchloric acid overnight. The concentration of drug in the solution was determined by the absorbance at 280 nm recorded. Drug loading of bare particle is 75.5% and drug loading after lipid coating is 70.1%.

1.8. Drug loading and release profile of Ca-Zol. By measuring the absorbances of zoledronic acid in five different concentrations in both 0.1 M HCl and 5 mM PBS at 215 nm, two corresponding standard curves were made. Particles were digested in 0.1 M HCl overnight. The concentration of drug in the solution was determined by the absorbance at 215 nm recorded. Drug loading of bare particle is 75.7% and drug loading after lipid coating is 67.0%.

1.9. In vitro assays. NCI-H460 large lung cancer cells (American Type Culture Collection (ATCC)# HTB-177) were purchased from the Tissue Culture Facility of Lineberger Comprehensive Cancer Center at the University of North Carolina at Chapel Hill. The cell line was maintained as a suspension in RPMI-1640 growth medium (Cellgro®, Mediatech, Inc., Manassas, Va., United States of America) supplemented with 10% fetal bovine serum (Sigma, St. Louis, Mo., United States of America) and 2% penicillin-streptomycin (Sigma, St. Louis, Mo., United States of America).

Figure 7:
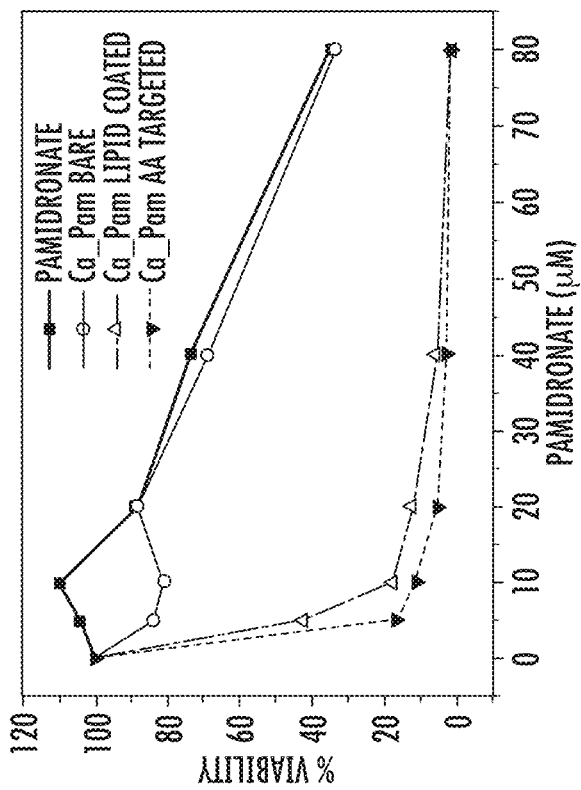
FIG. 7 is a graph of the results of a cancer cell inhibitory growth assay for H460 large lung cancer cells treated with crystalline calcium pamidronate (Ca-Pam) nanoparticles. Data for the as-synthesized Ca-Pam nanoparticles is shown with solid circles, data for lipid-coated Ca-Pam nanoparticles is shown with triangles, and data for anisamide (AA) targeted Ca-Pam nanoparticles is shown with upside down triangles. For comparison, data is also shown with free pamidronate (solid squares). The fifty percent inhibitory concentrations ($IC_{50}$'s) are estimated to be 65, 62, 4.2, and 2.7 µM for pamidronate, as-synthesized Ca-Pam, lipid-coated Ca-Pam, and AA-targeted Ca-Pam, respectively.

Confluent H460 cells were counted from the culture flask using a hematocytometer. Cells were plated in 6-well plates at a cell density of $5 \times 10^4$ cells/well in 3 mL RPMI-1640 complete growth medium. The cells were incubated at 37° C. and 5% $CO_2$ overnight. Pamidronate, and particle dispersions of Ca-Pam, lipid coated Ca-Pam, and AA-lipid coated Ca-Pam (80 µM) in RPMI-1640 media and additional media were added to wells, resulting in pamidronate concentrations (µM) of 0, 5, 10, 20, 40, and 80. Cells were incubated (37° C., 5% $CO_2$) with free pamidronate or particle for 48 h. Viability was determined by the trypan blue exclusion assay. Results of the assay are shown in FIG. 7. The $IC_{50}$s for AA-targeted Ca-Pam and lipid-coated Ca-Pam were determined to be 2.7 µM and 4.2 µM, respectively. In comparison, the $IC_{50}$s for free pamidronate and as-synthesized Ca-Pam nanoparticles were 65 µM and 62 µM, respectively.

Example 2

Figure 8:
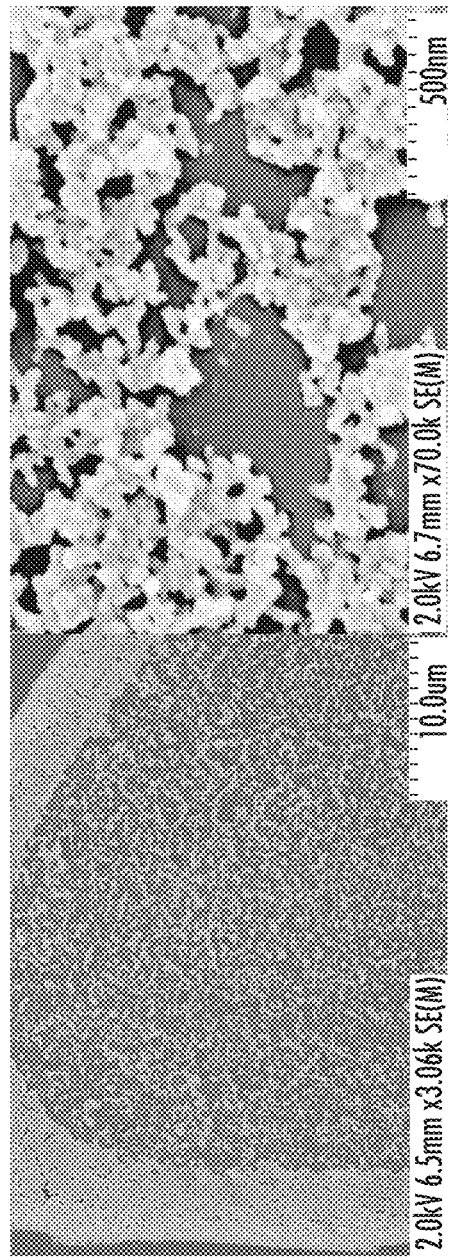
FIG. 8 is a pair of scanning electron microscopy (SEM) images of uncoated amorphous calcium zoledronate (A-Ca-Zol) nanoparticles.
Figure 9A:
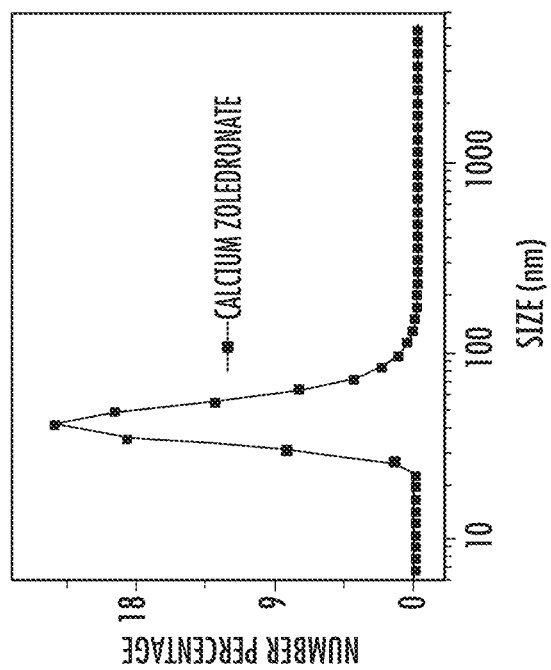
FIG. 9A is a graph showing an intensity-weighted dynamic light scattering (DLS) curve for amorphous calcium zoledronate (A-Ca-Zol) nanoparticles suspended in water.
Figure 9B:
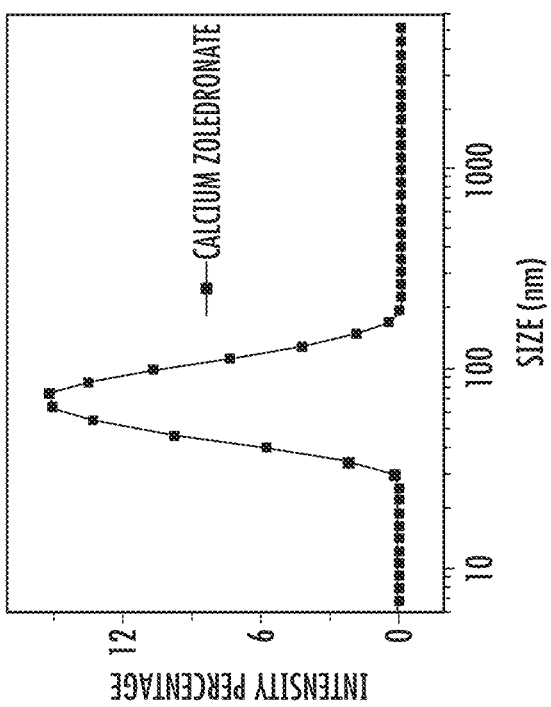
FIG. 9B is a graph showing a number-weighted dynamic light scattering (DLS) curve for amorphous calcium zoledronate (A-Ca-Zol) nanoparticles suspended in water.
Figure 10:
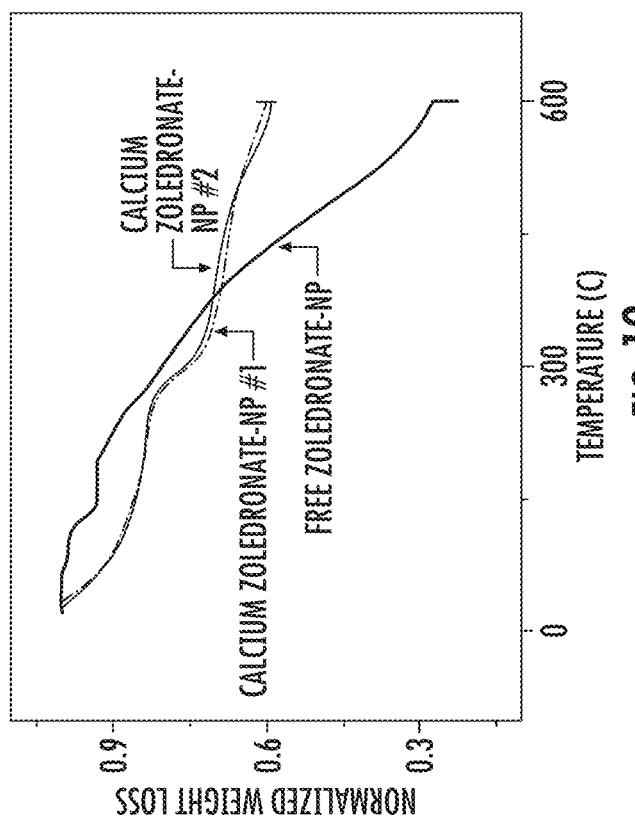
FIG. 10 is a graph showing the thermogravimetric (TGA) weight loss curves of uncoated amorphous (A-Ca-Zol) nanoparticles (i.e., Calcium Zoledronate-NP#1 and Calcium Zoledronate-NP#2) compared to free zoledronic acid (Free Zoledronate).

Amorphous Ca-Zol Nanoparticles 2.1. Synthesis of Amorphous Calcium Zoledronate (A-Ca-Zol) nanoparticles. A solution of 50 mM zoledronate was adjusted to pH=9 using aqueous ammonia (18 mL, 0.9 mmol). This solution was heated to 80° C. with vigorous stirring. An equal volume of 100 mM $CaCl_2$, pH=9) (1.8 mmol) was added rapidly, forming an immediate white precipitate. The nanoparticle suspension was aged at 80° C. overnight. The nanoparticles were isolated by centrifugation and washed with water once and 2% $NH_3$ in ethanol once. The particles were stored as an ethanolic suspension. SEM images of A-Ca-Zol nanoparticles are shown in FIG. 8. FIGS. 9A and 9B show the intensity- and number-weighted DLS curves for the A-Ca-Zol nanoparticles. FIG. 10 is a graph showing TGA weight loss curves for as-synthesized (bare) A-Ca-Zol nanoparticles.

2.2. Silica coating of A-Ca-Zol nanoparticles. Calcium zoledronate nanoparticles were coated with silica by a modified sol-gel procedure. Briefly, 30 mg of calcium-zoledronate nanoparticles were suspended into ethanol at 0.5 mg/mL. Tetraethylorthosilicate (180 µL, 0.8 mmol) and 33% ammonium hydroxide solution (3% of total volume) were then added. The suspension was vigorously stirred for 2 or 5 hours at room temperature. The nanoparticles were isolated by centrifugation and washed with ethanol twice. The nanoparticles were stored in ethanol.

Figure 11:
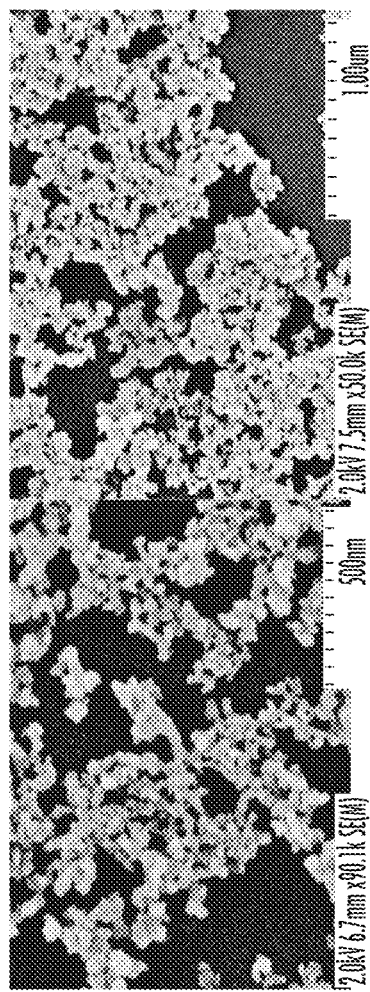
FIG. 11 is a pair of scanning electron microscopy (SEM) images of hour silica-coated amorphous calcium zoledronate (A-Ca-Zol) nano particles.
Figure 12A:
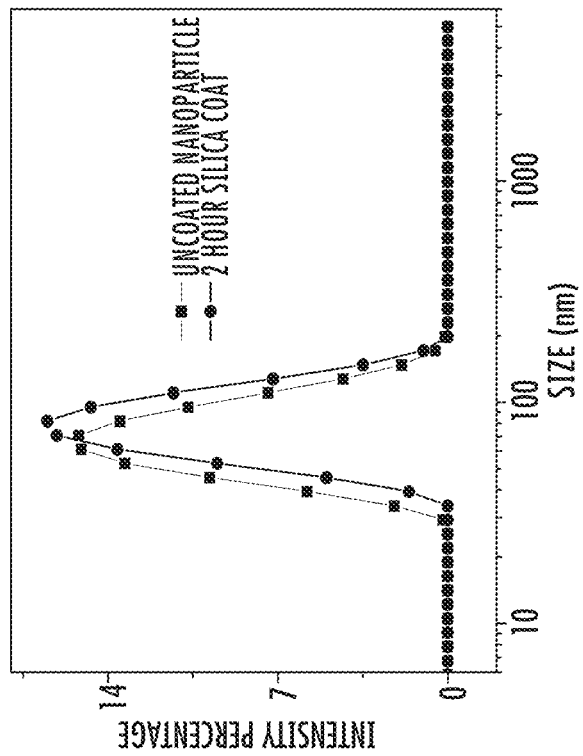
FIG. 12A is a graph showing the intensity-weighted dynamic light scattering (DLS) curves for uncoated (squares) and 2 hour silica-coated (diamonds) amorphous calcium zoledronate (A-Ca-Zol) nanoparticles.
Figure 12B:
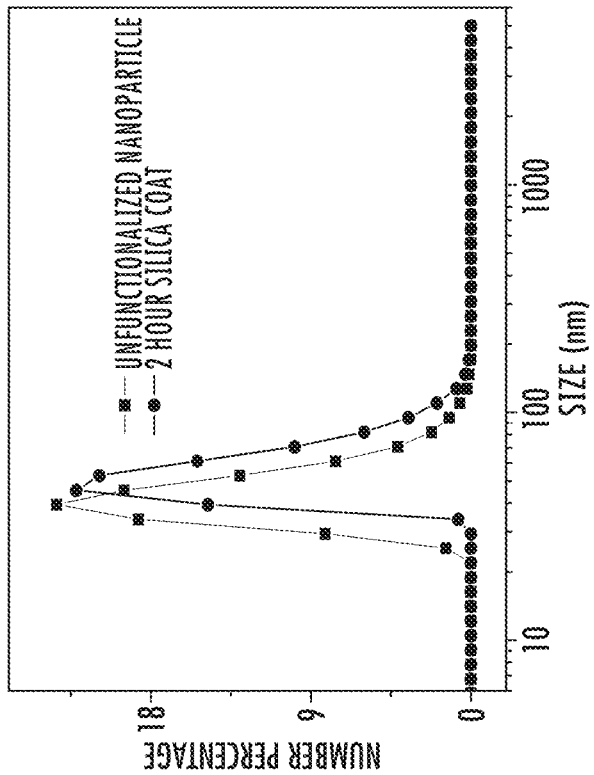
FIG. 12B is a graph showing the number-weighted dynamic light scattering (DLS) curves for uncoated (squares) and 2 hour silica-coated (diamonds) amorphous calcium zoledronate (A-Ca-Zol) nanoparticles.
Figure 13:
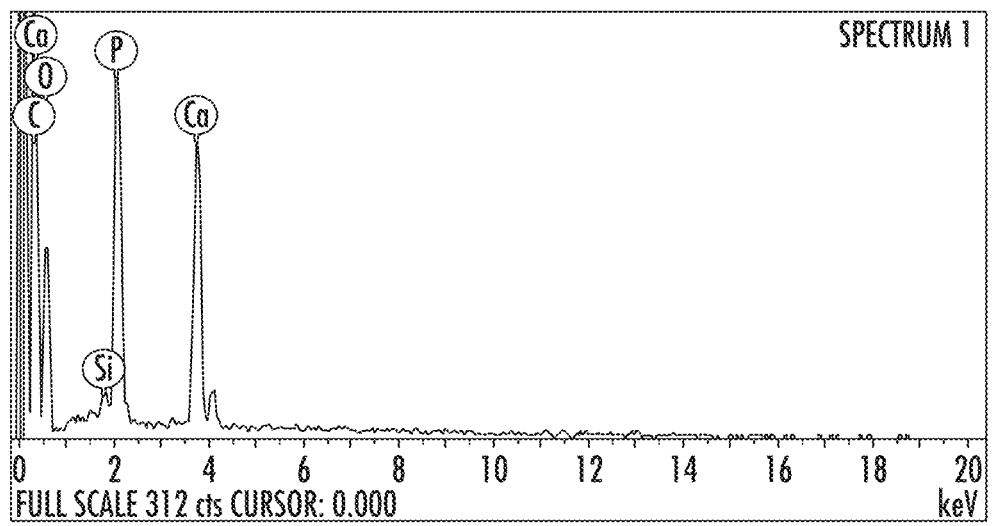
FIG. 13 is an energy dispersive X-ray spectroscopy (EDS) spectra of silica-coated amorphous calcium zoledronate (A-Ca-Zol) nanoparticles showing the presence of silica on the nanoparticle surface after 2 hours of coating reaction.
Figure 14:
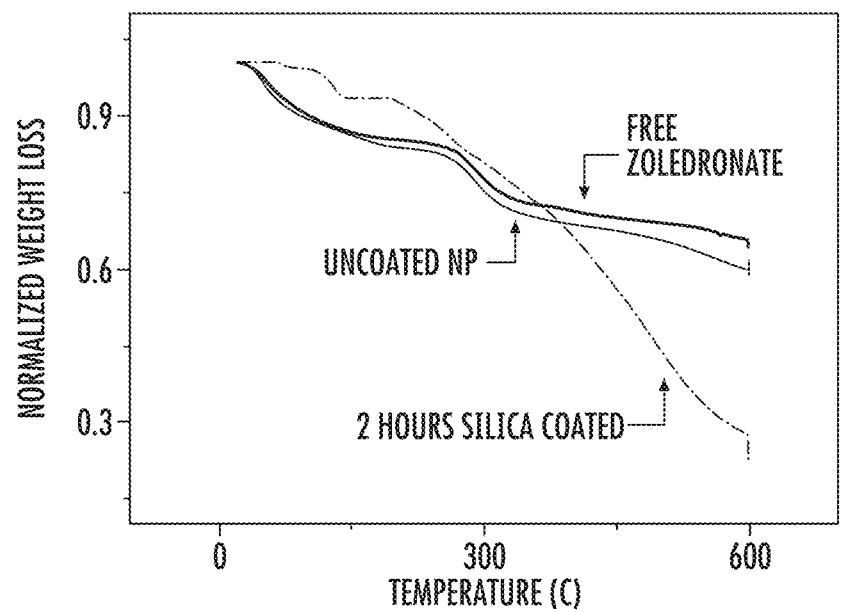
FIG. 14 is a graph showing the thermogravimetric analysis (TGA) weight loss curves of amorphous calcium zoledronate (A-Ca-Zol) nanoparticles before (Uncoated NP) and after a 2 hour silica coating reaction (2 Hours Silica Coated). The TGA weight loss curve for free zoledronate is also shown.

SEM images of 2 hour silica-coated A-Ca-Zol nanoparticles are shown in FIG. 11. FIGS. 12A and 12B show the intensity- and number-weighted DLS curves for silica-coated A-Ca-Zol nanoparticles that had been subjected to a 2 hour silica coating reaction. For comparison, the DLS curves for uncoated nanoparticles are also shown. FIG. 13 is an EDS spectra of the 2 hour silica-coated particles, indicating the presence of silica. FIG. 14 shows the TGA weight loss curves of both uncoated A-Ca-Zol nanoparticles and 2 hour silica coated A-Ca-Zol nanoparticles. The TGA weight loss curve for free zoledronate is also shown.

Figure 15:
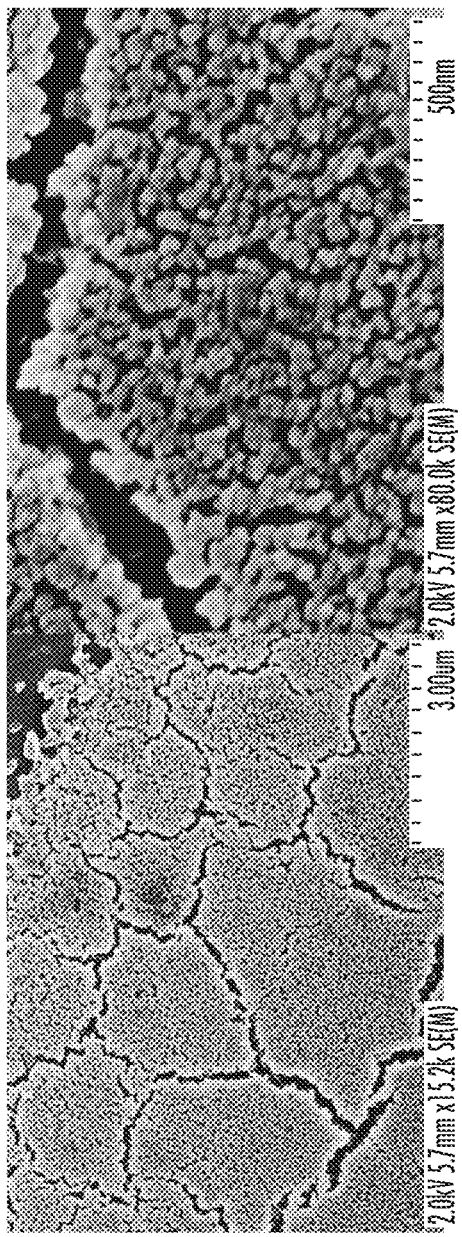
FIG. 15 is a pair of scanning electron microscopy (SEM) images of amorphous calcium zoledronate (A-Ca-Zol) nanoparticles after 5 hours of a silica coating reaction.
Figure 16A:
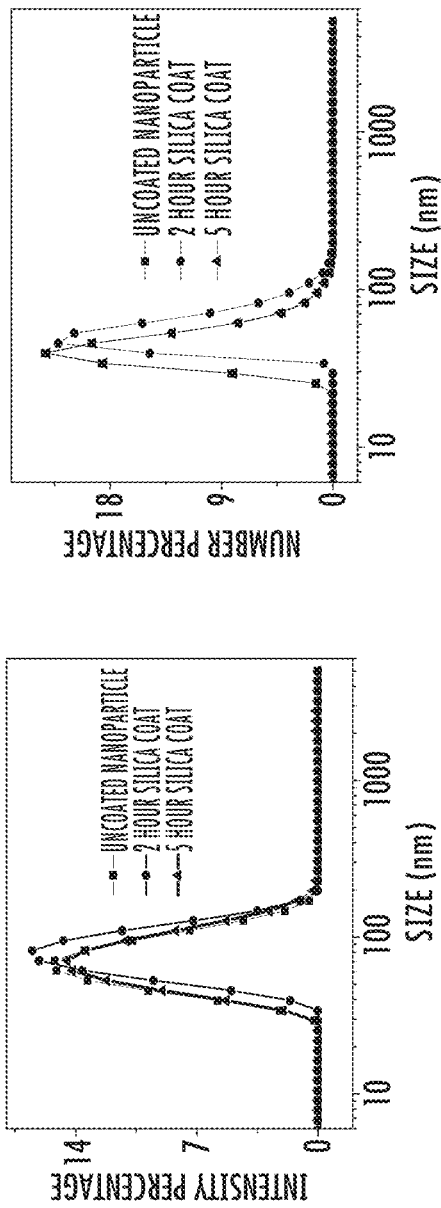
FIG. 16A is a graph of intensity-weighted dynamic light scattering (DLS) curves for uncoated amorphous calcium zoledronate (A-Ca-Zol) nanoparticles (squares); for 2 hour silica coated A-Ca-Zol nanoparticles (circles); and for 5 hour silica coated A-Ca-Zol nanoparticles (triangles).
Figure 16B:
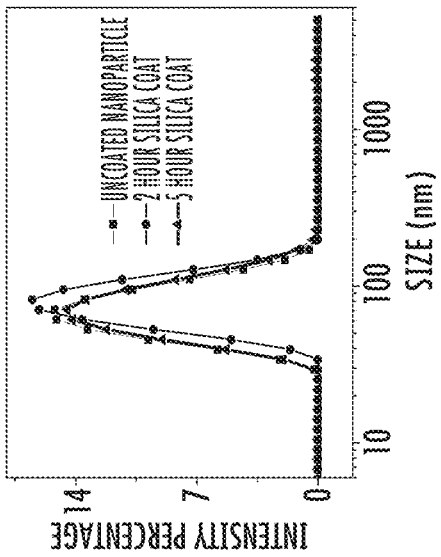
FIG. 16B is a graph of number-weighted dynamic light scattering (DLS) curves for uncoated amorphous calcium zoledronate (A-Ca-Zol) nanoparticles (squares); for 2 hour silica coated A-Ca-Zol nanoparticles (circles); and for 5 hour silica coated A-Ca-Zol nanoparticles (triangles).
Figure 17:
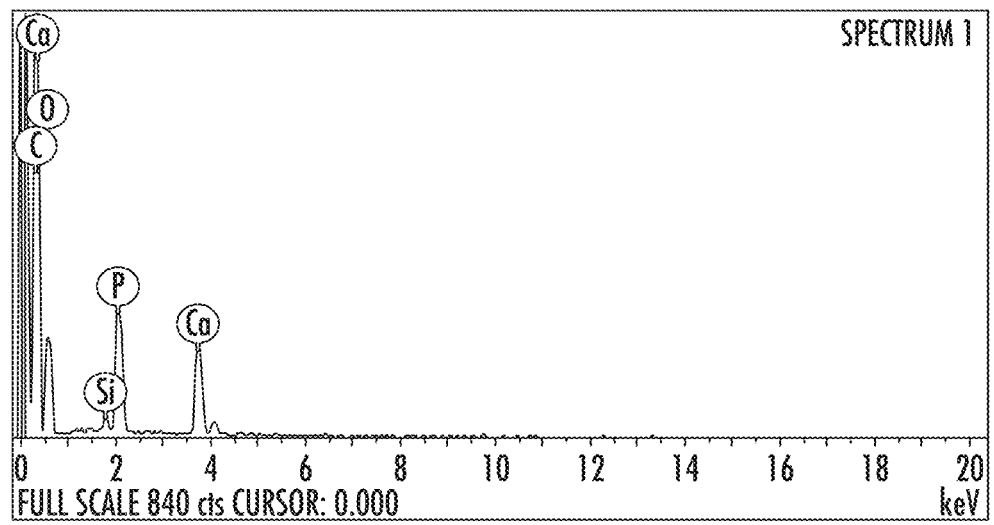
FIG. 17 is an energy dispersive X-ray spectroscopy (EDS) spectrum of amorphous calcium zoledronate (A-Ca-Zol) nanoparticles after 5 hours of a silica coating reaction.
Figure 18:
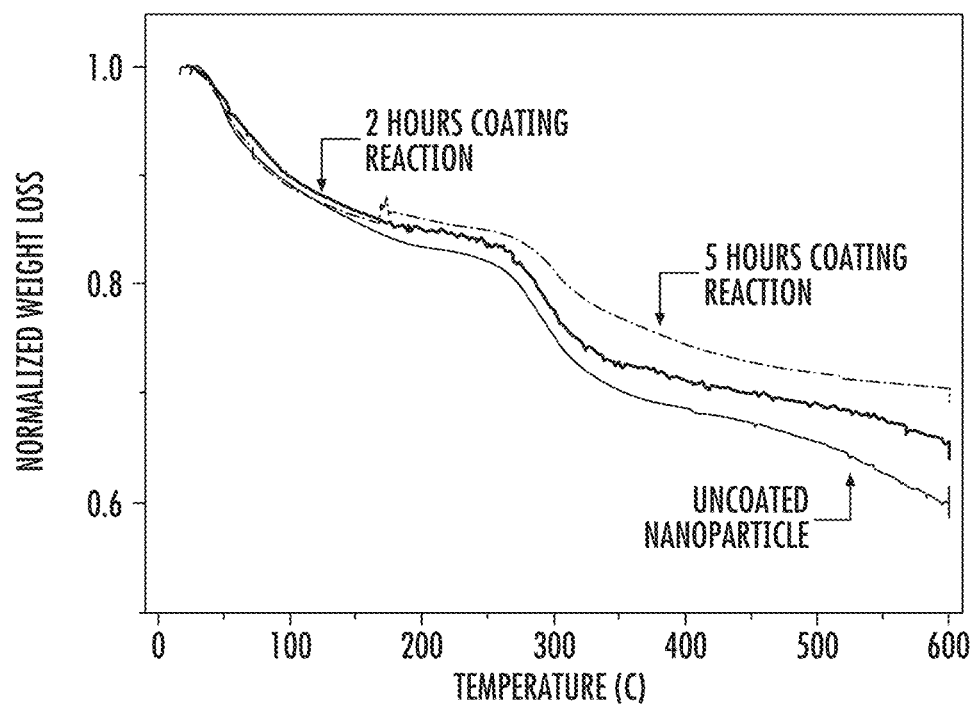
FIG. 18 is a graph of thermogravimetric analysis (TGA) weight loss curves for uncoated amorphous calcium zoledronate (A-Ca-Zol) nanoparticles, silica-coated A-Ca-Zol nanoparticles (2 hour reaction), and silica-coated A-Ca-Zol nanoparticles (5 hour reaction).

SEM images of 5 hour coated A-Ca-Zol nanoparticles are shown in FIG. 15. FIGS. 16A and 16B compare the intensity- and number-weighted DLS curves for uncoated, 2 hour silica coated, and 5 hour silica coated A-Ca-Zol nanoparticles. FIG. 17 is an EDS spectra of the 5 hour silica coated A-Ca-Zol nanoparticles and FIG. 18 is a graph showing the TGA weight loss curves of uncoated, 2 hour coated and 5 hour coated A-Ca-Zol nanoparticles.

2.3. Surface functionalization of silica-coated A-Ca-Zol nanoparticles.

Figure 19:
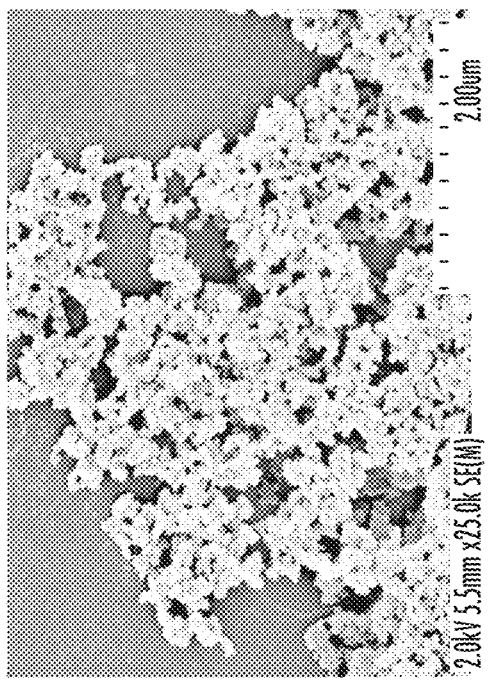
FIG. 19 is a scanning electron microscopy (SEM) image of cyclic RGD (cRGD)-targeted amorphous calcium zoledronate (A-Ca-Zol) nanoparticles.

RGD targeting: Four milligrams of silica-coated (5 hrs) calcium-zoledronate nanoparticles were redispersed into ethanol at 2 mg/mL. Silyl-derived cRGfK (0.2 mg in 50 µL DMSO) was added to the nanoparticle suspension. Aqueous ammonium hydroxide (33%) was added to make a 3% by volume solution in ethanol. The suspension was stirred at room temperature for 24 hours. The nanoparticles were isolated by centrifugation and washed with ethanol three times. The nanoparticles were stored as an ethanol suspension. FIG. 19 shows an SEM image of the RGD-targeted, silica-coated A-Ca-Zol nanoparticles.

Figure 20:
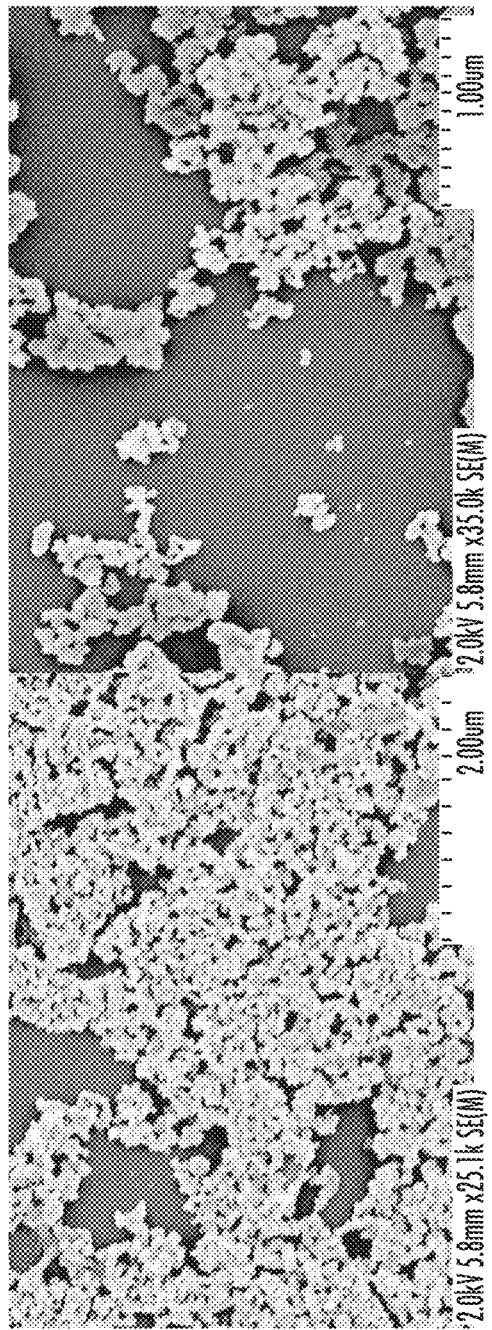
FIG. 20 is a pair of scanning electron microscopy (SEM) images of pegylated (left) and anisamide targeted (right) silica-coated amorphous calcium zoledronate (A-Ca-Zol) nanoparticles.

Pegylation and anisamide targeting of silica-coated A-Ca-Zol nanoparticles: Thirteen milligrams of silica coated (5 hour) calcium zoledronate nanoparticles were redispersed into 6.5 mL ethanol. Silyl-derived polyethylene glycol (MW: 2000) monomethyl ether (2.5 mg) was dissolved into the suspension and aqueous ammonium hydroxide was added to make a 3% $NH_4OH$ total concentration. The suspension was stirred at room temperature for 24 hours, before the nanoparticles were isolated by centrifugation and washed with ethanol twice. The particles were stored as an ethanolic suspension. Anisamide-targeted nanoparticles were prepared by the same procedure except a fraction (10 wt %) of silyl derived anisamide PEG (MW=2000) was added to the reaction. FIG. 20 shows SEM images of the pegylated and anisamide-targeted silica coated A-Ca-Zol nanoparticles. FIGS. 21A and 21B compare the intensity-weighted and number-weighted DLS curves for the unfunctionalized (i.e., as synthesized or bare) A-Ca-Zol nanoparticles, the 5 hour silica coated A-Ca-Zol nanoparticles, the pegylated A-Ca-Zol nanoparticles, and the AA-targeted A-Ca-Zol nanoparticles.

Figure 22:
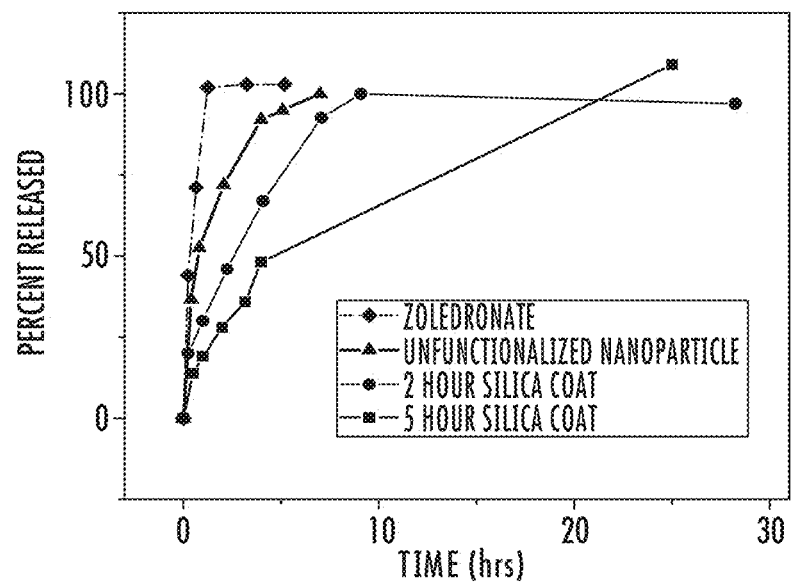
FIG. 22 is a graph showing zoledronate drug release over time from unfunctionalized amorphous calcium zoledronate nanoparticles (triangles), calcium zoledronate nanoparticles coated in a 2 hour silica coating reaction (circles) and calcium zoledronate nanoparticles coated in a 5 hour silica coating reaction (squares). The time dependent diffusion of the free drug from a dialysis bag (diamonds) is shown for comparison.

2.4. Zoledronate Release. Seventy-five milliliters of 5 mM PBS was placed within a beaker and warmed to 37° C. Either zoledronate, unfunctionalized calcium zoledronate nanoparticles, or silica coated calcium zoledronate nanoparticles (5 mg zoledronate present in all) was redispersed into 1 mL water and loaded into a 3500 MW cutoff dialysis bag. The dialysis bag was placed within the PBS solution and incubated at 37° C. Aliquots of the dialysate were removed periodically and the zoledronate concentration was determined by UV/Vis spectrometry. A graph of zoledronate drug release over time is shown in FIG. 22.

2.5. Cell Viability Assays. Four cell culturing plates were set-up for cell viability assays. In each well, 100,000 H460 human lung carcinoma cells were placed in each well with 3 mL of RPMI media (supplemented with 10% FBS and 2% PenStrep) and were allowed to incubate overnight for cell adhesion at 37° C. at 5% $CO_2$.

20 µM stock solutions of zolendrate, bare particle (i.e., as synthesized A-Ca-Zol), RGD targeted particle and anisamide targeted particle were prepared so that treatment curves of 0 µM, 1 µM, 5 µM, 10 µM, 20 µM and 30 µM were established in RPMI media. After individual treatment, the plates were placed back in the incubator for 48 hrs.

Figure 23:
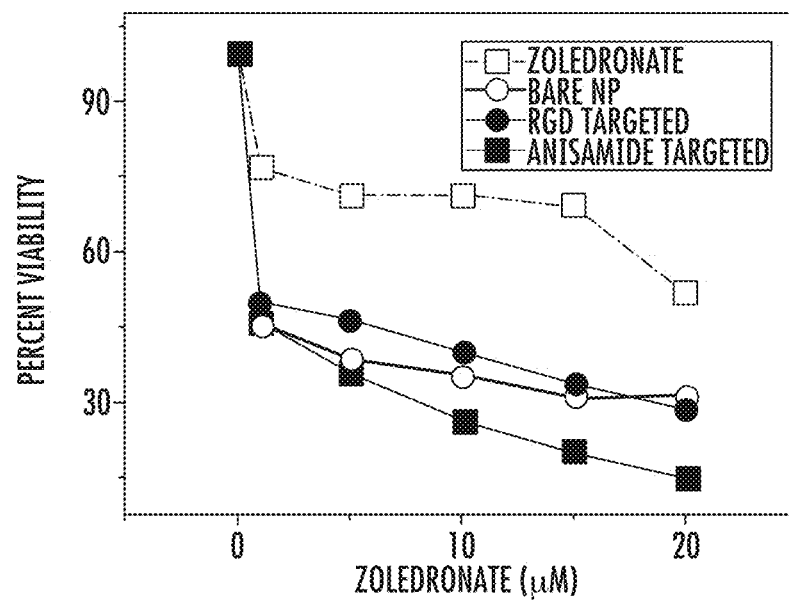
FIG. 23 is a graph showing cell viability curves for H460 human lung carcinoma cells treated with amorphous calcium zoledronate (A-Ca-Zol) nanoparticles and free zoledronate. The data for free zoledronate is shown with open squares, for as-synthesized A-Ca-Zol nanoparticles with open circles, for anisamide targeted A-Ca-Zol nanoparticles with solid squares, and for RGD targeted A-Ca-Zol nanoparticles with solid circles. The fifty percent inhibitory concentrations ($IC_{50}$'s) are estimated to be >20, 0.9, 0.9, and 2.5 µM for zoledronate, as-synthesized A-Ca-Zol, anisamide targeted A-Ca-Zol, and RGD targeted A-Ca-Zol, respectively.

After incubation, media and treatment was removed from each well and cells were washed 2× with 1 mL of PBS. 1 mL of trypsin was added to each well and placed back in the incubator for 3 min. The cells and trypsin were then transferred to centrifuge tubes and centrifuged for 3 min and the cell pellet was then redistributed in 1 mL of media. Cell counts were taken using 20 µL of cells and 20 µL trypan blue on a hemocytometer. Results are provided in FIG. 23. The fifty percent inhibitory concentrations ($IC_{50}$'s) are estimated to be >20, 0.9, 0.9, and 2.5 µM for zoledronate, as-synthesized A-Ca-Zol, anisamide targeted A-Ca-Zol, and RGD targeted A-Ca-Zol, respectively.

Figure 24:
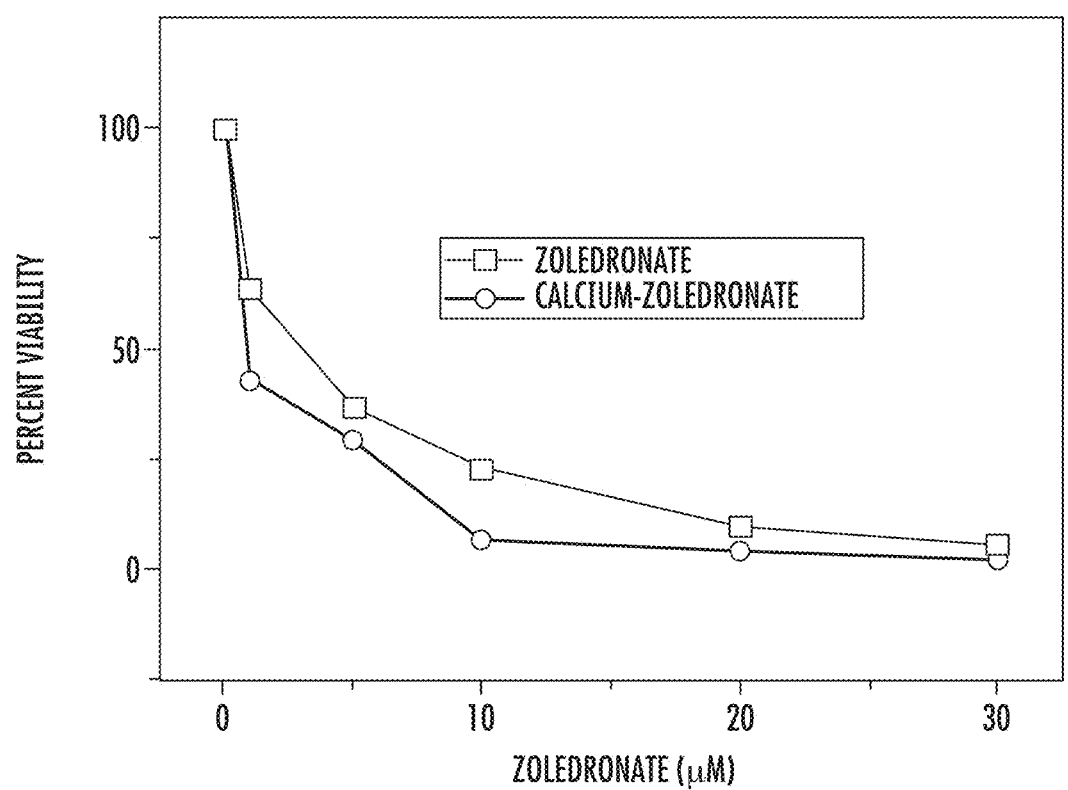
FIG. 24 is a graph showing the cell viability curves for human PC-3 prostate adenocarcinoma cells treated with amorphous, as synthesized (uncoated) calcium zoledronate (A-Ca-Zol) nanoparticles (circles). Data for cells treated with free zoledronate (squares) is shown for comparison. The fifty percent inhibitory concentration ($IC_{50}$'s) are estimated to be 3.1 µM and 0.8 µM for free zoledronate and as-synthesized A-Ca-Zol nanoparticles, respectively.

In addition, a cell viability assay was also performed in a similar manner, but using human PC-3 prostate adenocarcinoma cells. Cell viability results for PC-3 cells treated with either zoledronate or as synthesized A-Ca-Zol nanoparticles are provided in FIG. 24. The $IC_{50}$'s are estimated to be 3.1, and 0.8 for zoledronate and as-synthesized A-Ca-Zol, respectively.

Example 3

Manganese Zoledronate (Mn-Zol) Nanoparticles for Therapeutic and Imaging Applications 3.1. Crystalline Manganese Zoledronate Nanoparticle (Mn-Zol) Synthesis. Zoledronic acid (5 mg, 0.019 mmol) and $MnCl_2 \cdot 4H_2O$ (10 mg, 0.05 mmol) were dissolved in a solvent mixture of $DMF/H_2O$ (5 mL/2 mL). After adding 0.15 mL 3M HCl, the resulting solution was sealed in a microwave vessel and placed in the microwave oven with the power set to 400 W and run time set to 5 minutes. After 20 minutes of heating at 100° C. with stirring, the crystalline particles of Mn-Zol were isolated via centrifuge at 13000 rpm for 15 min. Before re-dispersing them in EtOH, they were washed once with water and three times with EtOH. Approximately 4.6 mg (70%) particles of Mn-Zol were isolated from this procedure. Functionalized (i.e., lipid coated and AA-targeted) Mn-Zol nanoparticles were also prepared according to methods described above in Example 1.

Figure 25B:
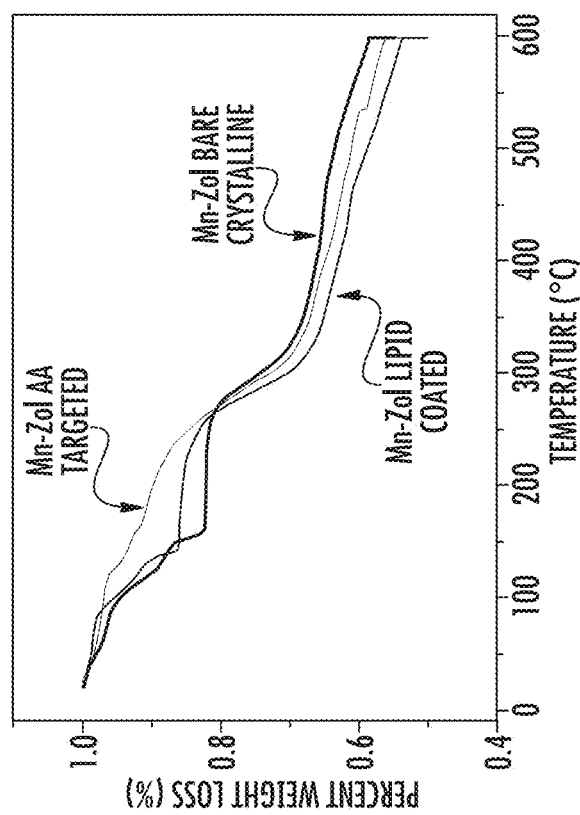
FIG. 25B is a graph showing the thermogravimetric analysis (TGA) curves of the manganese zoledronate (Mn-Zol) nanoparticles described in FIG. 25A.
Figure 25A:
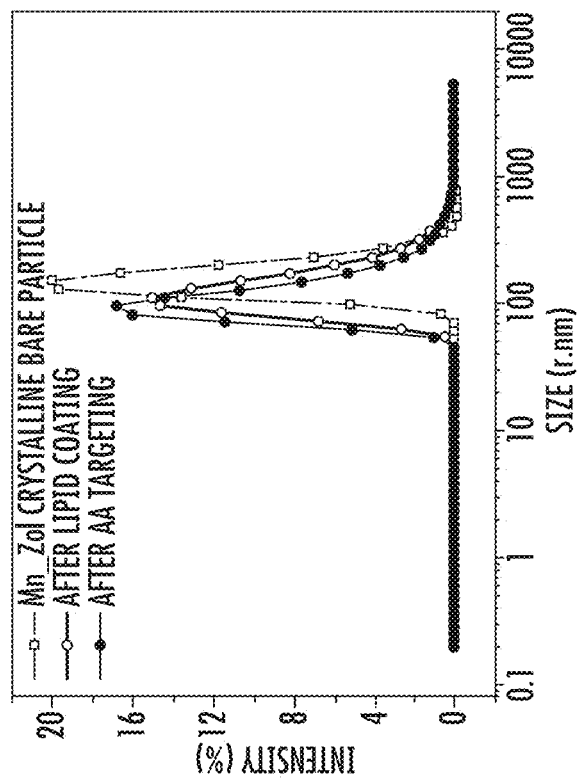
FIG. 25A is a graph showing the dynamic light scattering (DLS) hydrodynamic diameters of manganese zoledronate (Mn-Zol) nanoparticles as follows: open boxes, as-synthesized (bare) nanoparticles; open circles, nanoparticles after lipid coating; and solid circles, nanoparticles after anisamide (AA) targeting.
Figure 26:
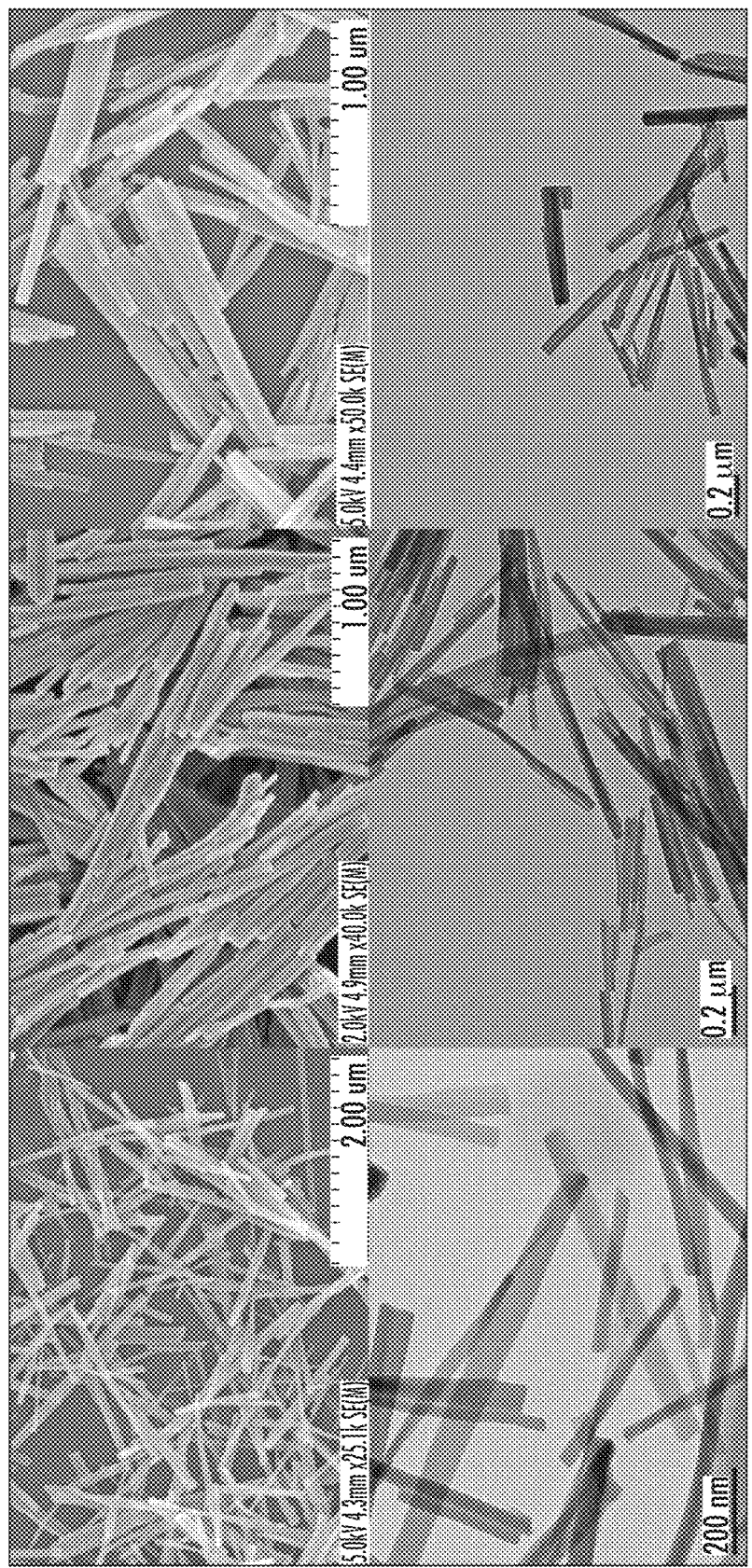
FIG. 26 is a set of scanning electron microscopy (SEM) images (top trio) and transmission electron microscopy (TEM) images (bottom trio) of manganese zoledronate (Mn-Zol) nanoparticles. The left-hand image of each trio is for as-synthesized (bare) nanoparticles, the middle image of each trio is for lipid-coated nanoparticles, and the right-hand image of each trio is for anisamide-targeted nanoparticles.

DLS data for the crystalline Mn-Zol nanoparticles is provided in Table 4, below. Also, FIG. 25A shows the DLS hydrodynamic diameters of bare (i.e., as synthesized), lipid-coated, and anisamide-targeted Mn-Zol nanoparticles, while FIG. 25B shows the TGA weight loss curves for the same particles. FIG. 26 is a set of SEM and TEM images for the Mn-Zol nanoparticles (i.e., the as synthesized particles, the lipid-coated particles, and the AA-targeted particles).

TABLE 4

DLS hydrodynamic diameters and zeta potentials of the Mn-Zol nanoparticles

| Mn-Zol | Z-Ave diameter (nm) | PDI | Zeta Potential (mV) |
|---|---|---|---|
| Bare | 195.7 ± 9 | 0.218 | −20.4 ± 2 |
| Lipid coated | 182.2 ± 10 | 0.208 | 26.0 ± 2 |
| AA targeted | 187.4 ± 13 | 0.254 | 24.6 ± 5 |

3.2. Amorphous manganese zoledronate nanoparticle (A-Mn-Zol) Synthesis. Zoledronic acid (5 mg, 0.019 mmol) and $MnCl_2 \cdot 4H_2O$ (10 mg, 0.05 mmol) were dissolved in a solvent mixture of $DMF/H_2O$ (10 mL/7 mL). After adding about 0.3 mL 3M HCl, the resulting solution was sealed in a microwave vessel and placed in the microwave oven with the power set to 400 W and run time set to 5 minutes. After 20 minutes of heating at 140° C. with stirring, the A-Mn-Zol particles were isolated via centrifuge at 13000 rpm for 15 min. Before re-dispersing them in EtOH, they were washed three times with EtOH. Approximately 3.1 mg (50%) particles of A-Mn-Zol were isolated from this procedure. Functionalized (i.e., lipid coated and AA-targeted) A-Mn-Zol nanoparticles were also prepared according to methods described above in Example 1.

Figure 27B:
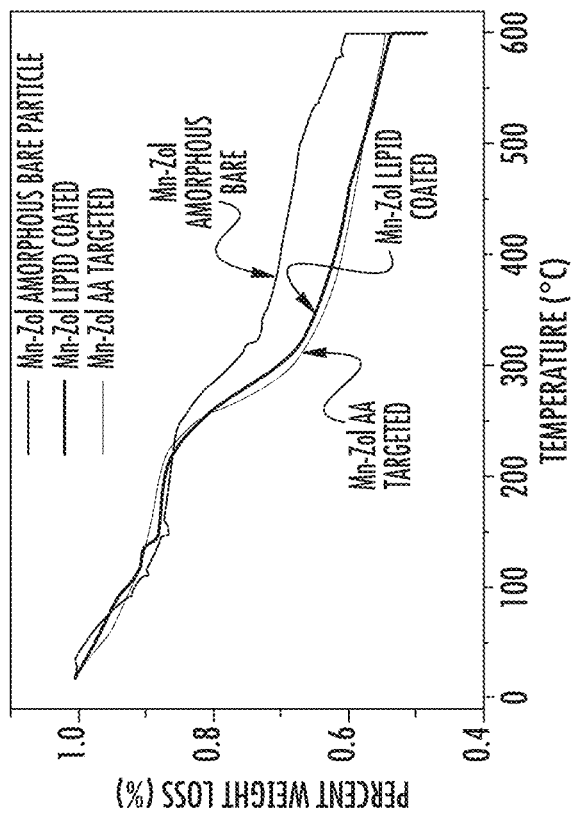
FIG. 27B is a graph showing the thermogravimetric analysis (TGA) curves of the amorphous manganese zoledronate (A-Mn-Zol) nanoparticles described in FIG. 27A.
Figure 27A:
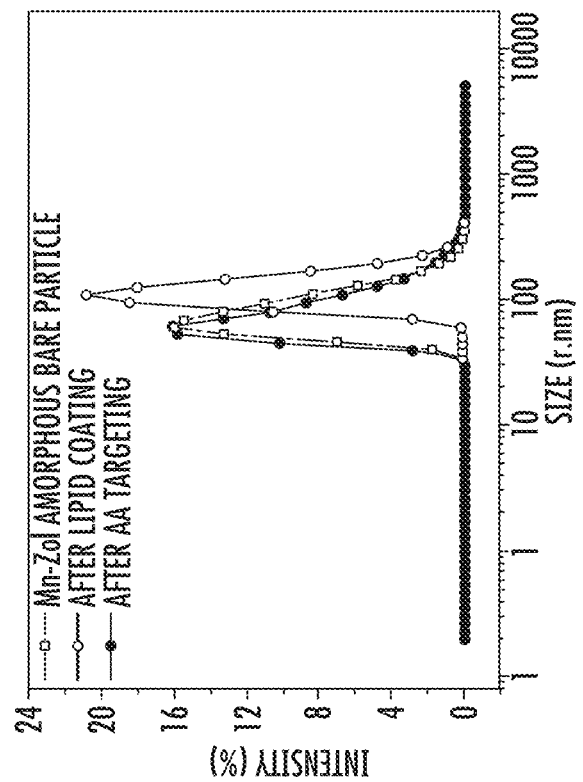
FIG. 27A is a graph showing the dynamic light scattering (DLS) hydrodynamic diameters of the amorphous manganese zoledronate (A-Mn-Zol) nanoparticles as follows: as-synthesized (bare) nanoparticles (squares); nanoparticles after lipid coating (open circles); and nanoparticles after anisamide (AA) targeting (solid circles).
Figure 28:
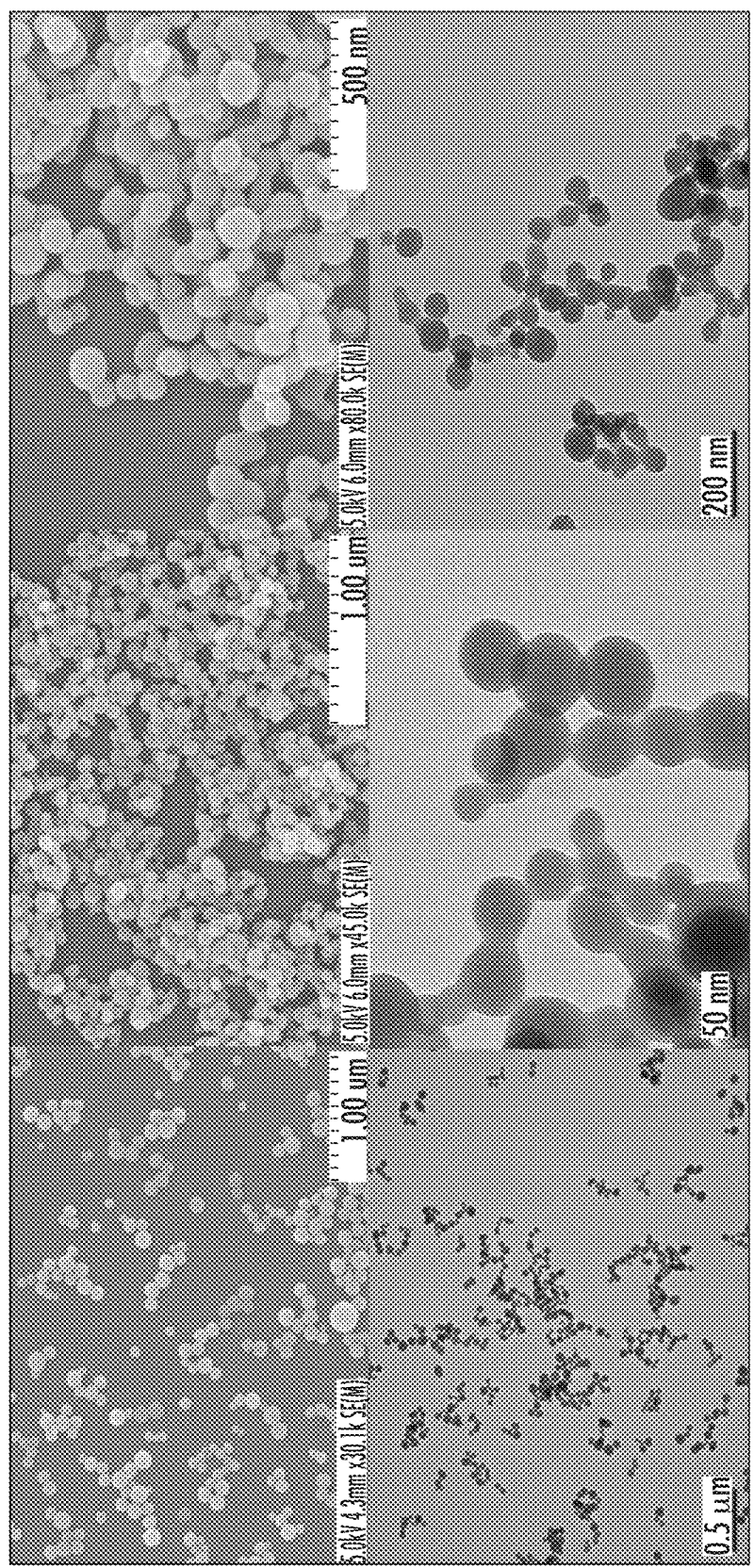
FIG. 28 is a set of scanning electron microscopy (SEM) images (top trio) and transmission electron microscopy (TEM) images (bottom trio) of amorphous manganese zoledronate (A-Mn-Zol) nanoparticles. The left-hand image of each trio corresponds to the as-synthesized (bare) nanoparticles, the middle image of each trio corresponds to the lipid-coated nanoparticles, and the right-hand image of each trio corresponds to the anisamide-targeted nanoparticles.

DLS data for the crystalline A-Mn-Zol nanoparticles is provided in Table 5, below. Also, FIG. 27A shows the DLS hydrodynamic diameters of bare (i.e., as synthesized), lipid-coated, and anisamide-targeted A-Mn-Zol nanoparticles, while FIG. 27B shows the TGA weight loss curves for the same particles. FIG. 28 is a set of SEM and TEM images for the A-Mn-Zol nanoparticles (i.e., the as synthesized particles, the lipid-coated particles, and the AA-targeted particles).

TABLE 5

DLS hydrodynamic diameters and zeta potentials of the A-Mn-Zol nanoparticles

| A-Mn-Zol | Z-Ave diameter (nm) | PDI | Zeta Potential (mV) |
|---|---|---|---|
| Bare | 125.3 ± 11 | 0.206 | −16.9 ± 4 |
| Lipid coated | 136.6 ± 6 | 0.126 | 27.8 ± 5 |
| AA targeted | 138.5 ± 7 | 0.224 | 29.4 ± 3 |

Figure 29:
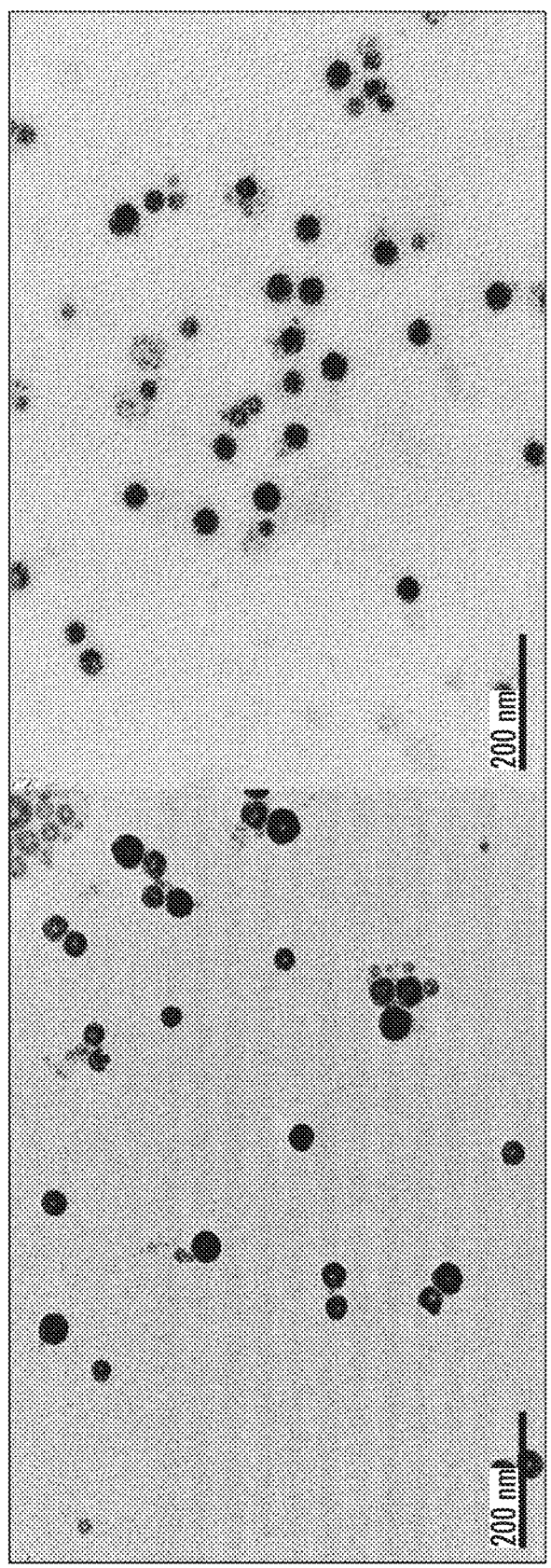
FIG. 29 is a pair of transmission electron microscopy (TEM) images of amorphous manganese zoledronate nanoparticles (A-Mn-Zol) before (left image) and after (right image) pegylation.

3.3. Synthesis of pegylated amorphous manganese zoledronate nanoparticles (PEG-A-Mn-Zol). Zoledronic acid (5 mg, 0.019 mmol), $MnCl_2 \cdot 4H_2O$ (10 mg, 0.05 mmol) and 5 mg DOPA were dissolved in a solvent mixture of $DMF/H_2O$ (16 mL/3 mL), the resulting solution was sealed in a microwave vessel and placed in the microwave oven with the power set to 800 W and run time set to 2 minutes. After 10 minutes of heating at 140° C. with stirring, the amorphous particles were isolated via centrifuge at 13000 rpm for 15 min. Before re-dispersing them in THF, they were washed once with cyclohexane and twice with EtOH. Approximately 2.3 mg (28%) particles were isolated from this procedure. The resulting particles were coated with lipid and Lipid-PEG by adding a THF solution of DOPC, cholesterol (1:1 molar ratio), DSPE-$PEG_{2k}$ (20 mol %) to the nanoparticles in 500 ul 30% (v/v) $EtOH/H_2O$ at 50° C. THF was evaporated and the solution was allowed to cool to room temperature to resulting in PEG-A-Mn-Zol. The right-hand image in FIG. 29 shows the TEM micrograph of PEG-A-Mn-Zol nanoparticles. The left-hand image of FIG. 29 shows the A-Mn-Zol nanoparticles prior to pegylation.

3.4. Determination of Drug Loading and Release Profile. By measuring the absorbances of zoledronic acid in five different concentrations in 0.1 M HCl at 207.5 nm, corresponding standard curve was made. Particles were digested in 0.1 M HCl overnight. The concentration of drug in the solution was determined by the absorbance at 207.5 nm recorded. Drug loading of Mn-Zol bare nanoparticle is 76.8% and drug loading after lipid coating is 69.9%. Drug loading of A-Mn-Zol bare nanoparticle is 82.7% and drug loading after lipid coating is 71.2%.

Figure 30:
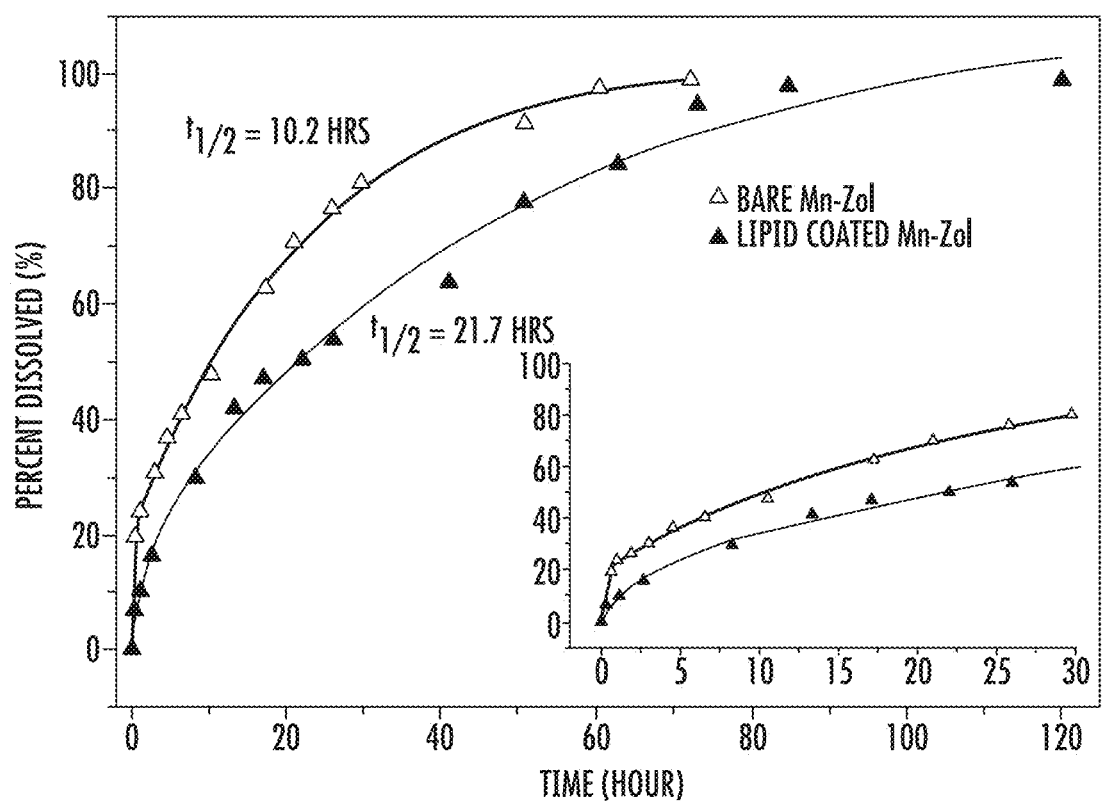
FIG. 30 is a graph showing the zoledronate release profiles of uncoated (bare) manganese zoledronate (Mn-Zol) nanoparticles (dotted lines) and lipid coated Mn-Zol nanoparticles (solid lines) at 5 mM phosphate buffered saline (PBS) at 37° C.
Figure 32:
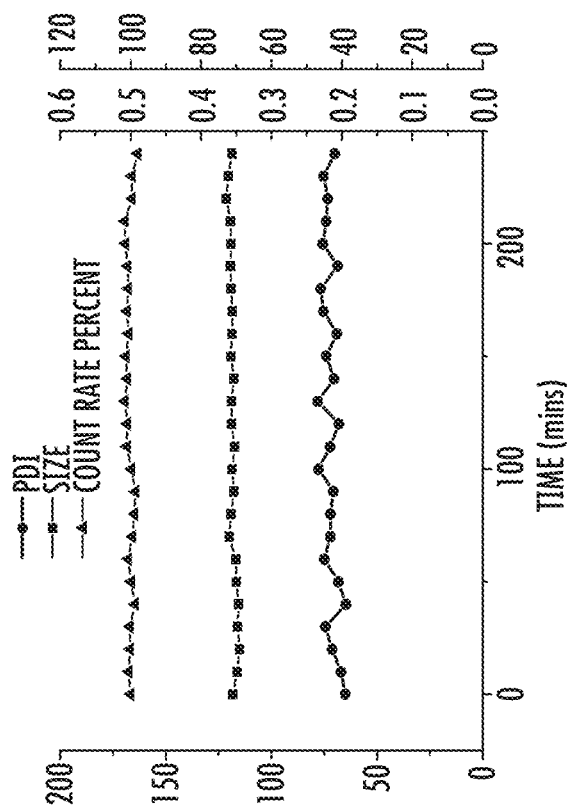
FIG. 32 is a graph showing the results of a stability test of pegylated amorphous manganese zoledronate (PEG-A-Mn-Zol) nanoparticles in phosphate buffered saline (PBS) with bovine serum albumin (BSA). Data relating to the polydispersity index (PDI) of the nanoparticles is shown in circles; data relating to the size of the nanoparticles is shown in squares, and data relating to the count rate percent is shown in triangles.
Figure 31:
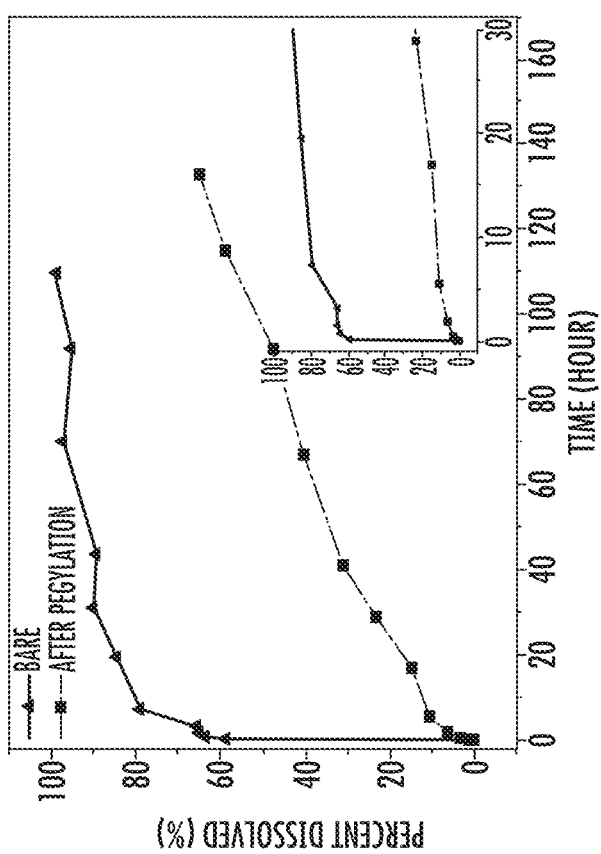
FIG. 31 is a graph showing the release profiles of bare (triangles) and pegylated (squares) amorphous manganese zoledronate nanoparticles.

3.5. Release profiles of Mn-Zol and A-Mn-Zol nanoparticles. By measuring the absorbances of zoledronic acid in five different concentrations in 5 mM PBS at 215 nm, corresponding standard curve was made. Drug released from dialysis tubing with 3500 MW cutoff was monitored by UV-Vis in 5 mM PBS at 37° C. The release profiles of the bare and lipid coated Mn-Zol nanoparticles are shown in FIG. 30. The release profile of PEG-A-Mn-Zol nanoparticles is shown in FIG. 31. The inset shows the zoomed-in view of the drug release from the nanoparticles. FIG. 32 shows the results of a stability test of PEG-A-Mn-Zol nanoparticles in PBS with bovine serum albumin (BSA). The stability test was carried out in PBS buffer containing high concentrations of BSA in order to mimic the plasma protein in circulation. It was understood that such tests would provide guidance on how stable the nanoparticles are during circulation and how resistant they are to plasma protein absorption which is the first step of the cascade leading to the recognition of the nanoparticles by the RES system.

3.6. In vitro assays. NCI-H460 large lung cancer cells (ATCC #HTB-177) and MCF-7 human breast cancer cells (ATCC #HTB-22) were purchased from the Tissue Culture Facility of Lineberger Comprehensive Cancer Center at the University of North Carolina at Chapel Hill. The cell line was maintained as a suspension in RPMI-1640 growth medium (Cellgro®, Mediatech, Inc., Manassas, Va., United States of America) supplemented with 10% fetal bovine serum (Sigma, St. Louis, Mo., United States of America) and 2% penicillin-streptomycin (Sigma, St. Louis, Mo., United States of America).

Figure 33:
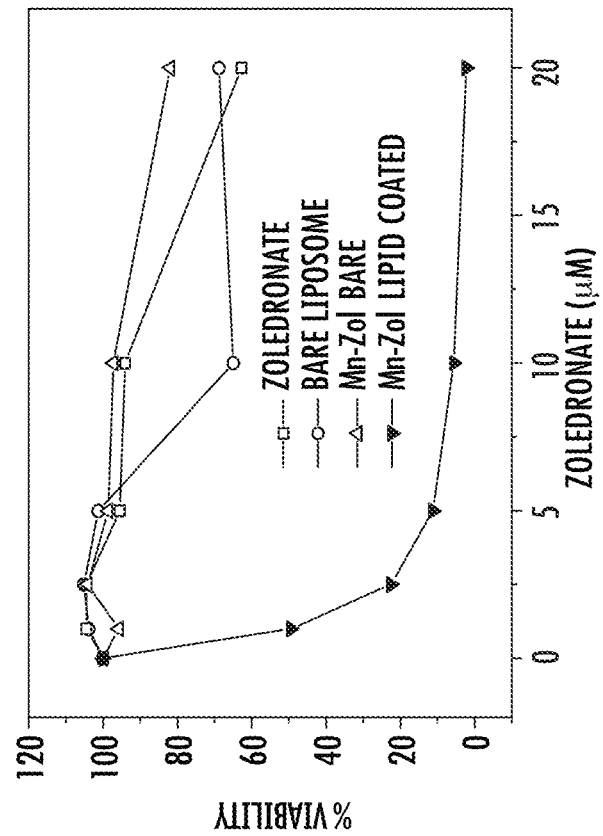
FIG. 33 is a graph of the cell viability curves for H460 cancer cells treated with manganese zoledronate (Mn-Zol) nanoparticles. The data for as-synthesized Mn-Zol nanoparticles (Mn-Zol bare) is shown using triangles, while the data for lipid-coated Mn-Zol (Mn-Zol lipid coated) nanoparticles is shown using upside down triangles. For comparison, data using free zoledronate (squares) and bare liposomes (circles) is also shown. The fifty percent inhibitory concentrations ($IC_{50}$'s) are estimated to be >20 µM, >20 µM, >20 µM, and 0.98 µM for zoledronate, bare liposome, as-synthesized Mn-Zol, and lipid-coated Mn-Zol, respectively.

Confluent H460 cells were counted from the culture flask using a hematocytometer. Cells were plated in 6-well plates at a cell density of $5 \times 10^4$ cells/well in 3 mL RPMI-1640 complete growth medium. The cells were incubated at 37° C. and 5% $CO_2$ overnight. Zoledronate, bare liposome, and particle dispersions of Mn-Zol and lipid coated Mn-Zol (20 µM) in RPMI-1640 media and additional media were added to wells, resulting in zoledronate concentrations (µM) of 0, 1.0, 2.5, 5, 10, and 20. Cells were incubated (37° C., 5% $CO_2$) with free zoledronate, liposome, or particle for 48 h. Viability was determined by the trypan blue exclusion assay. Results are shown in FIG. 33. The fifty percent inhibitory concentrations ($IC_{50}$'s) are estimated to be >20 µM, >20 µM, >20 µM, and 0.98 µM for zoledronate, bare liposome, as-synthesized (bare) Mn-Zol, and lipid-coated Mn-Zol, respectively.

Figure 34:
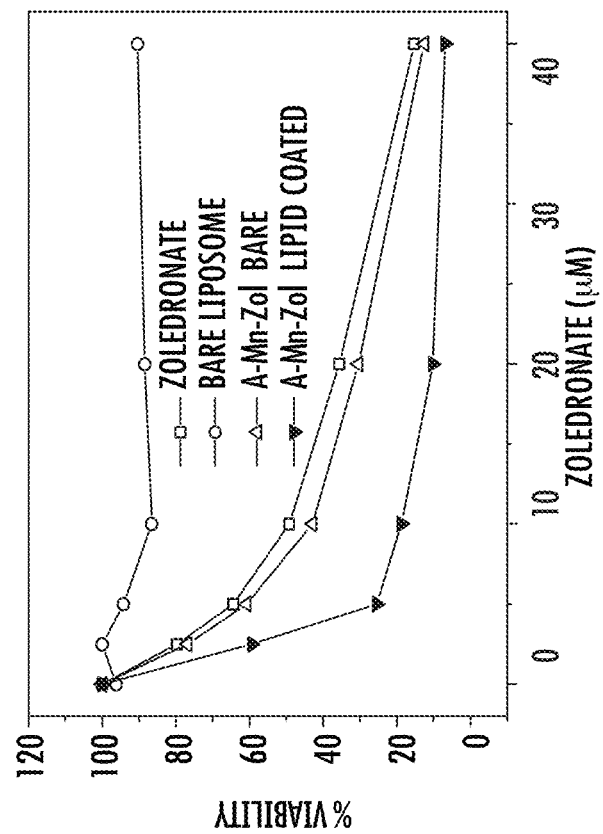
FIG. 34 is a graph of the cell viability curves for MCF-7 cancer cells treated with amorphous manganese zoledronate (A-Mn-Zol) nanoparticles. The data for as-synthesized A-Mn-Zol nanoparticles (A-Mn-Zol bare) is shown using triangles, while the data for lipid-coated A-Mn-Zol nanoparticles (A-Mn-Zol lipid coated) is shown using upside down triangles. For comparison, data using free zoledronate (squares) and bare liposomes (circles) is also shown. The fifty percent inhibitory concentrations ($IC_{50}$'s) are estimated to be 9 µM, >40 µM, 8 µM, and 3 µM for zoledronate, bare liposome, as-synthesized A-Mn-Zol, and lipid-coated A-Mn-Zol, respectively.

Confluent MCF-7 cells were trypsinized (trypsin-EDTA, Sigma, St. Louis, Mo., United States of America) and cell density was obtained from a hemocytometer. 6-well plates were seeded with $5.0 \times 10^4$ cells/well and a total of 3 mL media. The plates were incubated at 37° C. and 5% $CO_2$ overnight. Amounts of zoledronate, liposomes, and particle dispersions in RPMI-1640 medium and additional media (5% phosphate buffered saline, Cellgro®, Mediatech, Inc., Manassas, Va., United States of America) were added to wells resulting in zoledronate concentrations of 0, 2.5, 5, 10, 20, and 40 µM. The plates were incubated at 37° C. and 5% $CO_2$ for 48 h and viability was determined via the trypan blue exclusion assay. Results are shown in FIG. 34. The fifty percent inhibitory concentrations ($IC_{50}$'s) are estimated to be 9 µM, >40 µM, 8 µM, and 3 µM for zoledronate, bare liposome, as-synthesized (bare) A-Mn-Zol, and lipid-coated A-Mn-Zol, respectively.

FIGS. 35A and 35B present data from cytotoxicity assays of Mn-Zol@DOPA, PEG-A-Zn-Zol, and AA-PEG-A-Mn-Zol particles against ASPC-1 (FIG. 35A) and MCF-7 cells (FIG. 35B). In FIGS. 35A and 35B, graphs show cytotoxicity assays of Mn-Zol@DOPA (squares; $IC_{50}$ value in FIG. 35A, 60 µM; $IC_{50}$ value in FIG. 35B, 15 µM, PEG-A-Zn-Zol (triangles; $IC_{50}$ value in FIG. 35A, 33 µM; $IC_{50}$ value in FIG. 35B, 6 µM), and AA-PEG-A-Mn-Zol particles (crosses; $IC_{50}$ value in FIG. 35A, 20 µM; $IC_{50}$ value in FIG. 35B, 4 µM) against ASPC-1 (FIG. 35A) and MCF-7 cells (FIG. 35B). In each of FIGS. 35A and 35B, Zol=diamonds; $IC_{50}$ value greater than 60 µM in each Figure.

Figure 36A:
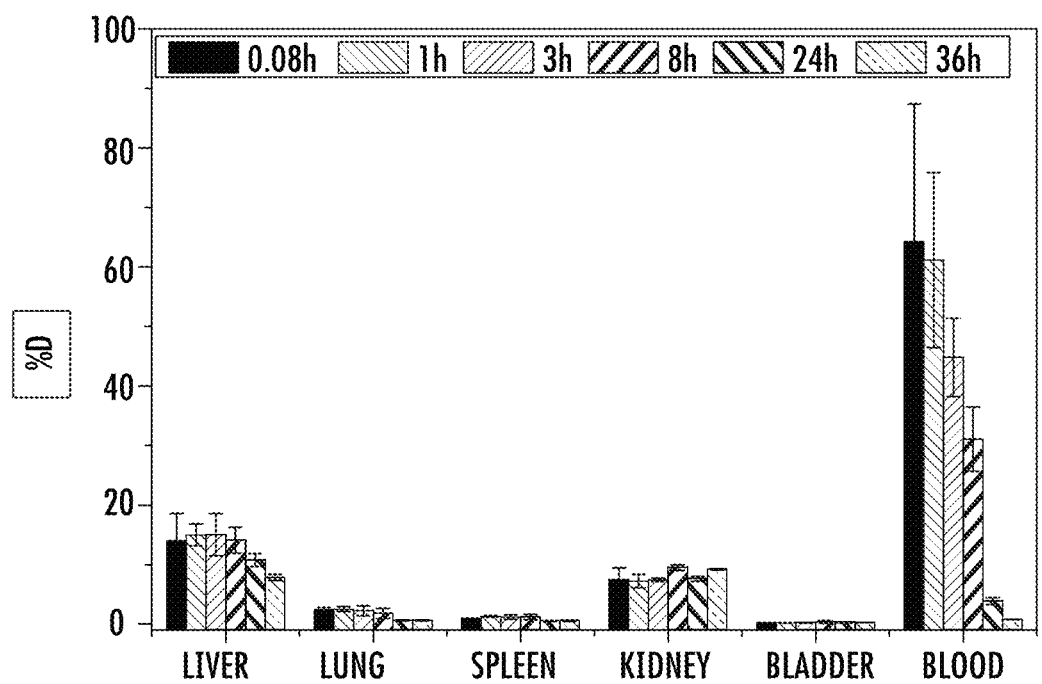
FIG. 36A is a bar graph showing the distribution of injected doses (as a percentage (%) of the injected dose, i.e., % D) of pegylated amorphous manganese zoledronate (PEG-A-Mn-Zol) nanoparticles in the liver, lung, spleen, kidney, bladder, and blood of mice as indicated in the x-axis. % D is provided at different time points (i.e., 0.08, 1, 3, 8, 24, and 36 hours, from left to right for each set of bars) post injection.
Figure 36B:
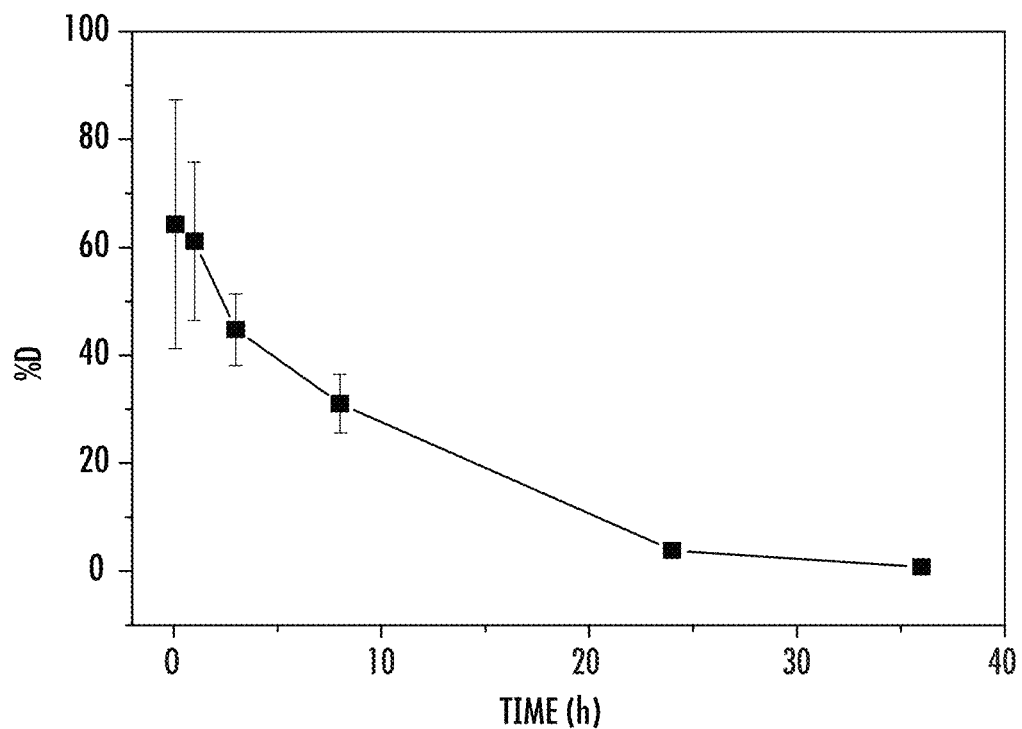
FIG. 36B is a graph showing the blood circulation profile of pegylated amorphous manganese zoledronate (PEG-A-Mn-Zol) in mice.

3.7. Blood Circulation and organ distributions of PEG-A-Mn-Zol Nanoparticles. Normal mice were injected with PEG-A-Mn-Zol particles at 10 mg/kg equivalent Zol doses via tail veins. The mice were sacrificed at different time points and their blood, liver, lung, spleen, kidney, and bladder were collected. These organs (and blood samples) were digested with concentrated nitric acid and analyzed for Mn contents by ICP-MS. See FIG. 36A. The Mn distribution serves as a surrogate for the Zol distribution as only the intact particles were expected to circulate in the blood. FIG. 36B indicates that the un-optimized PEG-A-Mn-Zol particles can circulate in the blood with a half-life of about 8 hours. PEG-A-Mn-Zol particles thus appear to possess necessary stealth properties to evade the RES system and effectively accumulate in the tumor.

Figure 37A:
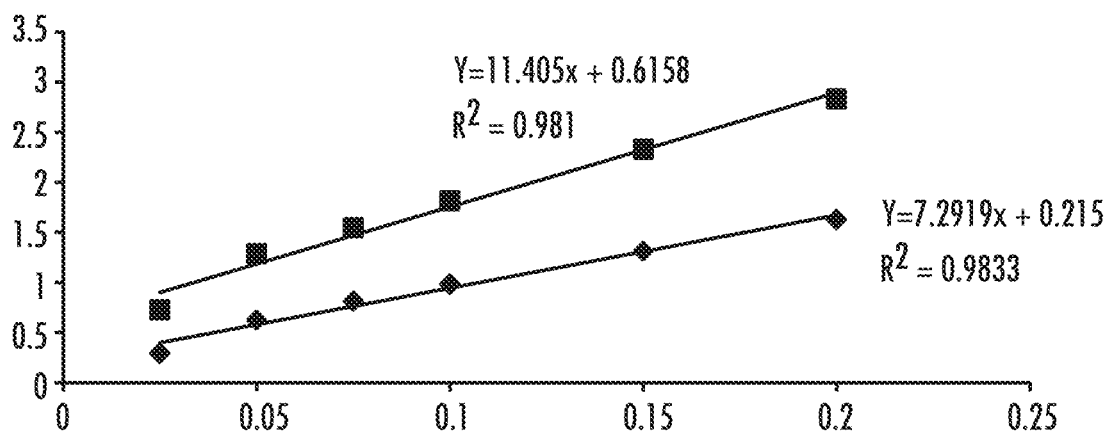
FIGS. 37A-37C are longitudinal (r1, squares) and transverse (r2, diamonds) MR relaxivities of Mn-Zol@DOPA (FIG. 37A), PEG-A-Zn-Zol (FIG. 37B), and AA-PEG-A-Mn-Zol (FIG. 37C) particles.
Figure 37B:
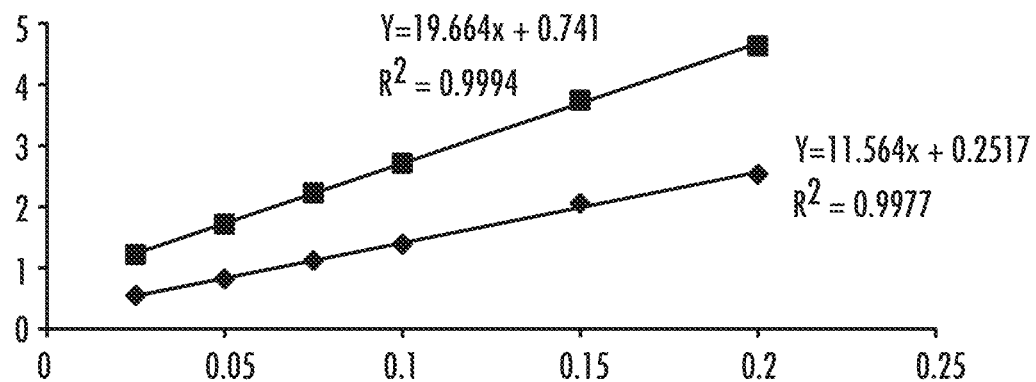
Figure 37C:
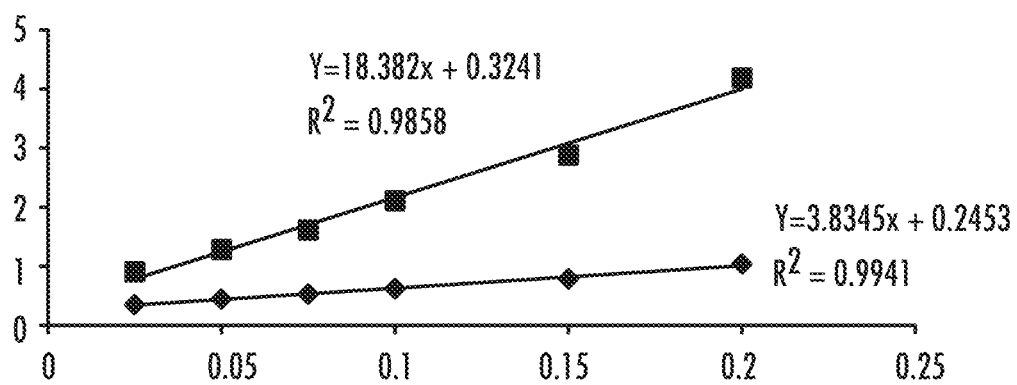

FIGS. 37A-37C are longitudinal (r1, squares) and transverse (r2, diamonds) MR relaxivities of Mn-Zol@DOPA (FIG. 37A), PEG-A-Zn-Zol (FIG. 37B), and AA-PEG-A-Mn-Zol (FIG. 37C) particles. For the longitudinal plot in FIG. 37A, y=11.405x+0.6158, $R^2$=0.981; and for the transverse plot in FIG. 37A, y=7.2919x+0.215, $R^2$=0.9833. For the longitudinal plot in FIG. 37B, y=19.664x+0.741, $R^2$=0.9994; and for the transverse plot in FIG. 37B, y=11.564x+0.2517, $R^2$=0.9977. For the longitudinal plot in FIG. 37C, y=18.382x+0.3241, $R^2$=0.9858; and for the transverse plot in FIG. 37C, y=3.8345x+0.2453, $R^2$=0.9941.

Example 4

Cisplatin Bisphosphonate-Zinc (cisPtBp-Zn) Nanoparticles

Scheme 4. Synthesis of Cisplatin Bisphosphonate Complex.

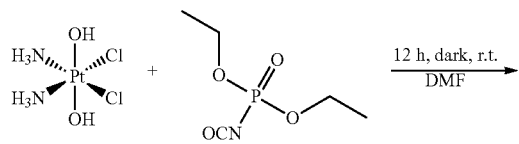

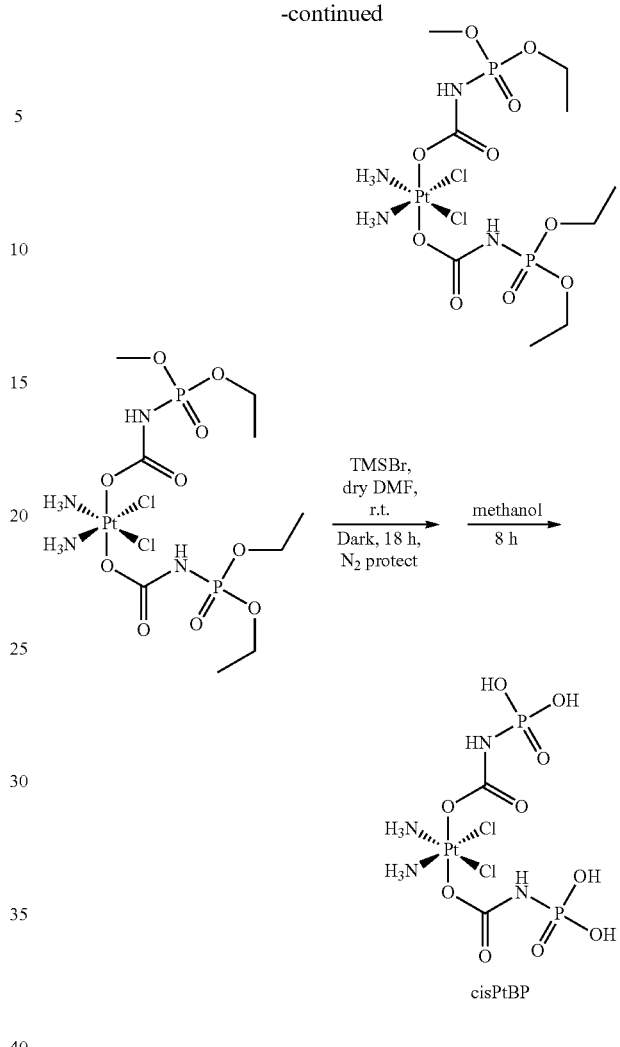

4.1. Synthesis of the Cisplatin Bisphosphonate (cisPtBP) Complexes. As shown above in Scheme 4, to a suspension of cis,cis,trans-[Pt(NH$_3$)$_2$Cl$_2$(OH)$_2$] (0.5 g, 1.5 mmol) in 2 mL of DMF was added a 1 mL of DMF solution containing 4 mol equivalents of diethoxyphosphinyl isocyanate (0.92 mL, 6.0 mmol). The resulting mixture was stirred for 12 h at room temperature in the dark. The solution was filtered, and the intermediate cisPtBP ethyl ester was precipitated by the addition of diethyl ether, and washed with diethyl ether for at least twice to remove the residual DMF. $^1$H NMR in DMSO-$d_6$ showed proton signals consistent with the cisPtBP-ester structure. Yield: 80%.

Before further reaction, the intermediate ester complex was further dried under vacuum for 4 h. To a solution of the ethyl ester complex (250 mg, 0.36 mmol) in dry DMF was added 475 uL trimethylsilyl bromide (3.6 mmol) at 0° C., and the mixture was allowed to react for 18 h at room temperature in the dark. After concentrating the reaction mixture, the desired product was precipitated by the addition of dichloromethane and further washed with dichloromethane at least twice more. The solid was dissolved in methanol (MeOH) and stirred at room temperature for 8 h in order to hydrolyze the silyl ester. After concentrating the reaction mixture, dichloromethane was poured into the reaction mixture to precipitate the desired product cisPtBP, and the solid was washed with dichloromethane twice more. $^1$H NMR in $D_2O$ showed proton signals consistent with the cisPtBP structure. Yield: 60%.

The dichloro-R,R-diaminocyclohexane platinum bisphosphonate complex (DACHPtBp) was prepared using similar procedures and as shown in Scheme 5. below.

EtOH/THF. The cisPtBp-Zn-DOPA nanoparticles were then redispersed in THF and stored until further surface modification.

Scheme 5. Synthesis of dichloro-R,R-diaminocyclohexane platinum bisphosphonate complex.

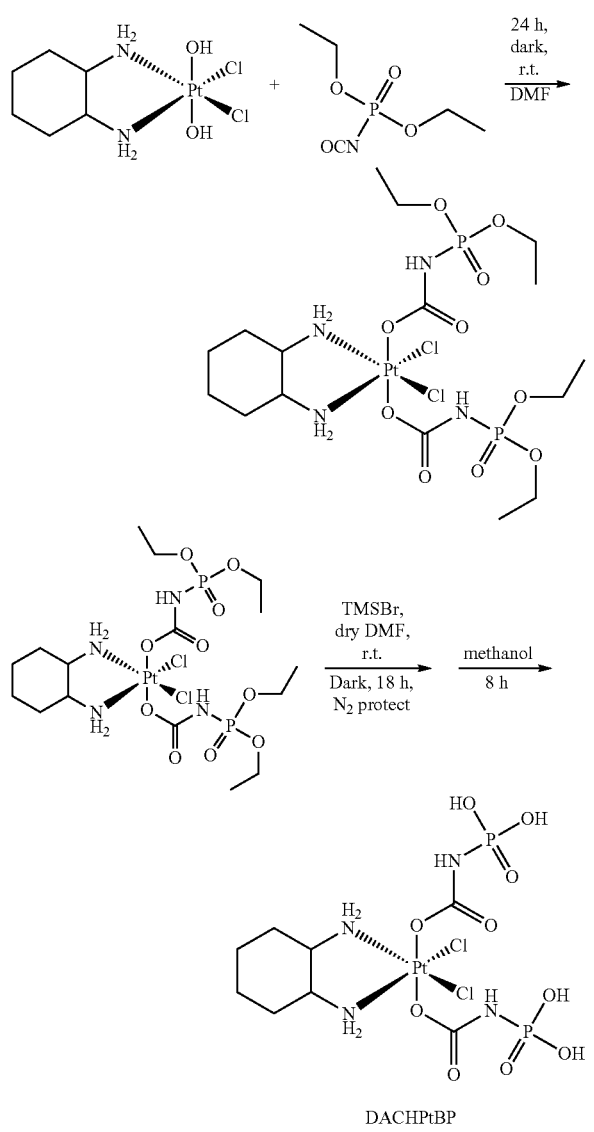

Scheme 6. Synthesis of cisplatin bisphosphonate metal nanoparticles.

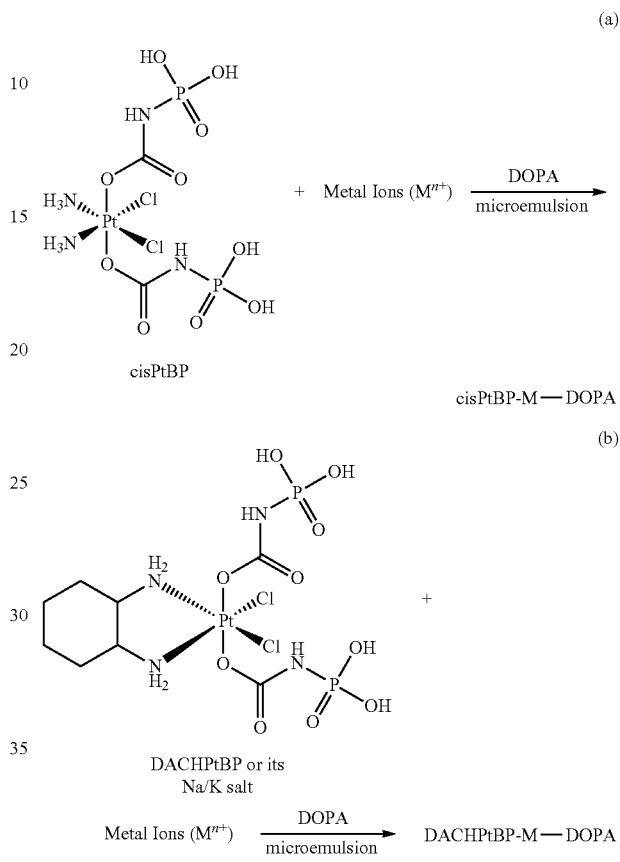

4.2. Procedures for Nanoparticle Synthesis: cisPtBp-Zn-DOPA Nanoparticle Synthesis. As shown in part (a) of Scheme 6 below, 0.2 mL of a 25 mg/mL cisPtBp sodium salt aqueous solution or 0.2 mL of a 100 mg/mL $Zn(NO_3)_2$ aqueous solution was added to two separate 5 mL aliquots of a 0.3 M Triton X-100/1.5 M 1-hexanol solution in cyclohexane under vigorous stirring at room temperature to form two separate microemulsions with w=7.4. 20 uL DOPA (200 mg/mL in $CHCl_3$) was added to the cisPtBp microemulsion and the mixture was stirred for 15 mins until a clear solution formed. The two microemulsions were combined, and the resultant 10 mL microemulsion with w=7.4 was stirred for an additional 30 minutes. After the adding of 20 mL of ethanol, cisPtBp-Zn-DOPA nanoparticles were isolated and washed once with ethanol and twice with 50%

4.3. Procedures for Nanoparticle Synthesis: DACHPtBp-Zn-DOPA Particle Synthesis. As shown in part (b) of Scheme 6, above, 0.2 mL of a 25 mg/mL DACHPtBp sodium salt aqueous solution or 0.2 mL of a 100 mg/mL $Zn(NO_3)_2$ aqueous solution was added to two separate 5 mL aliquots of a 0.3 M Triton X-100/1.5 M 1-hexanol in cyclohexane under vigorous stirring at room temperature to form two separate microemulsions with w=7.4. 20 uL DOPA (200 mg/mL in $CHCl_3$) was added to the DACHPtBp microemulsion and the mixture was stirred for 15 mins until a clear solution formed. The two microemulsions were combined, and the resultant 10 mL microemulsion with w=7.4 was stirred for an additional 30 minutes. After the addition of 20 mL of ethanol, DACHPtBp-Zn-DOPA nanoparticles were isolated and washed once with ethanol and twice with 50% EtOH/THF. The resulting DACHPtBp-Zn-DOPA nanoparticles were redispersed in THF and stored until further surface modification.

4.4 General procedures of lipid coating and pegylation. The lipid coated and pegylated nanoparticles, cisPtBp-Zn-PEG or DACHPtBp-Zn-PEG, were obtained by adding a THF solution of DOPC, cholesterol (1:1 molar ratio), DSPE-$PEG_{2k}$ (20 mol %) and cisPtBp-Zn-DOPA or DACHPtBp-Zn-DOPA nanoparticles to 500 μl 30% (v/v) $EtOH/H_2O$ at 50° C. THF was evaporated by blowing $N_2$ through and the resulting solution was allowed to cool to room temperature.

The resulting cisPtBp-Zn-PEG or DACHPtBp-Zn-PEG nanoparticles were stored at room temperature until use.

Figure 38:
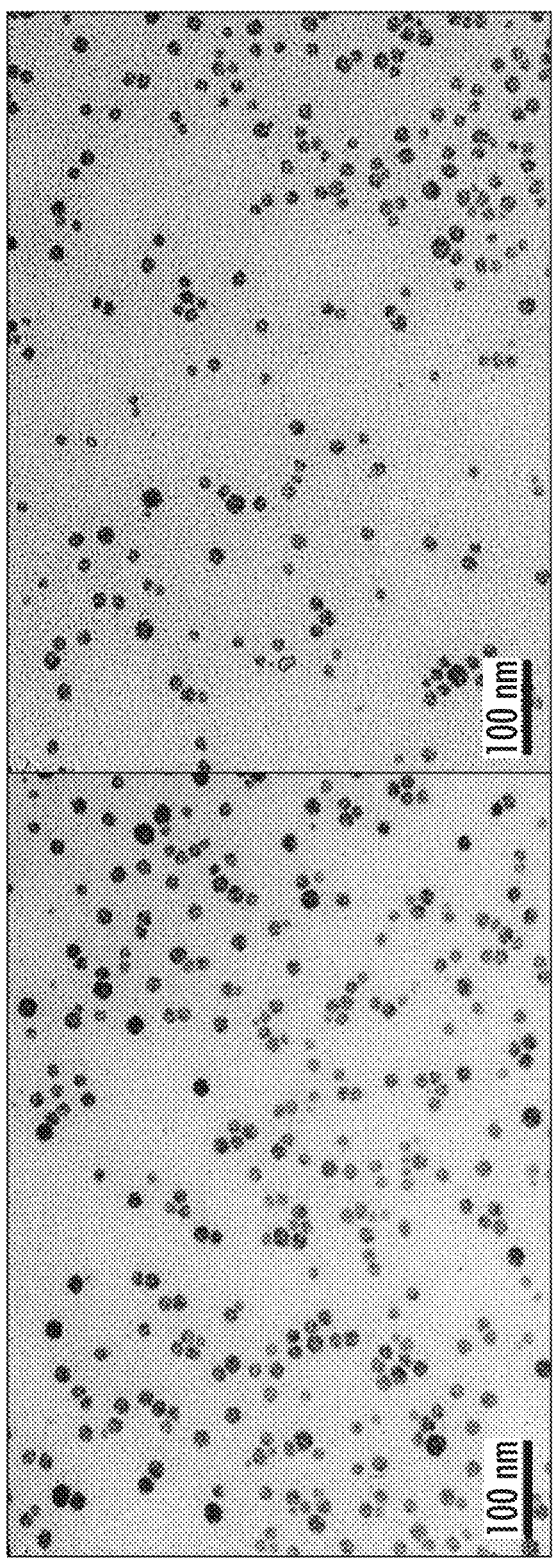
FIG. 38 is a pair of transmission electron microscopy (TEM) images of cis, cis, trans-$[Pt(NH_3)_2Cl_2(OH)_2]$ bisphosphonate-zinc nanoparticles prepared in a microemulsion containing 1,2-dioleoyl-sn-glycero-3-phosphate (cisPtBp-Zn-DOPA).
Figure 39:
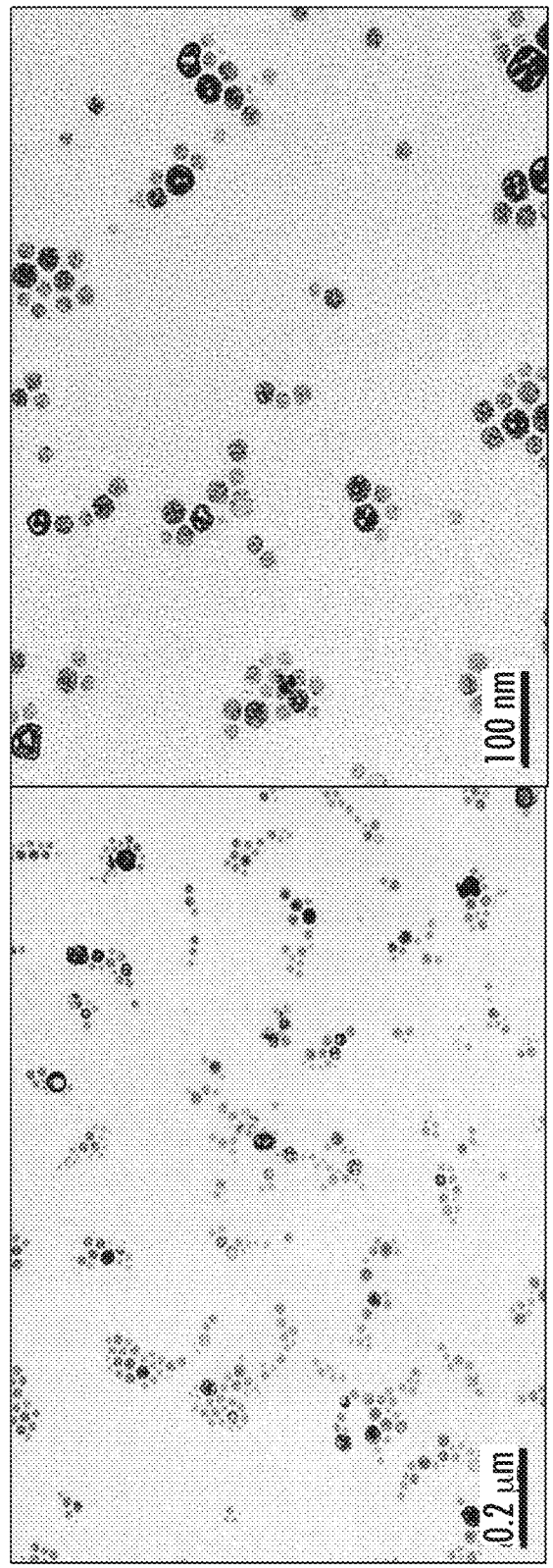
FIG. 39 is a pair of transmission electron microscopy (TEM) images of a pegylated version (cisPtBp-Zn-PEG) of the nanoparticles described for FIG. 36.
Figure 40:
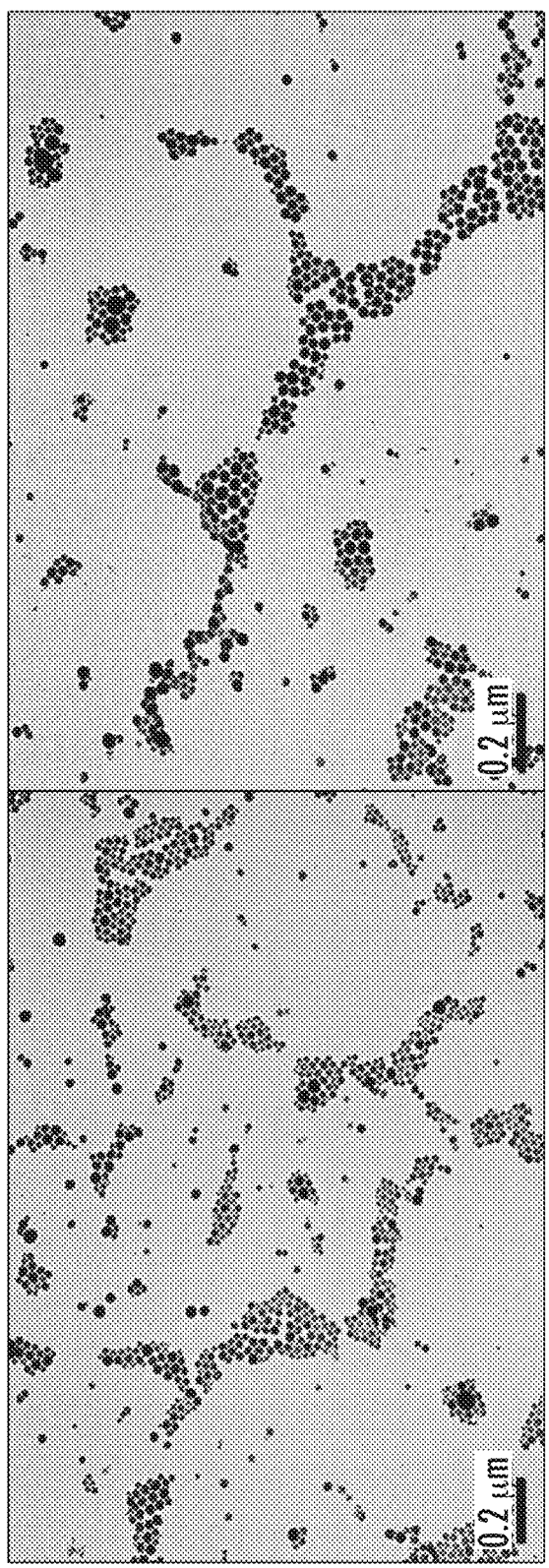
FIG. 40 is a pair of transmission electron microscopy (TEM) images of dichloro-R,R-diaminocyclohexane platinum-bisphosphonate complex-zinc nanoparticles prepared in a microemulsion containing 1,2-dioleoyl-sn-glycero-3-phosphate (DACHPtBp-Zn-DOPA).
Figure 41:
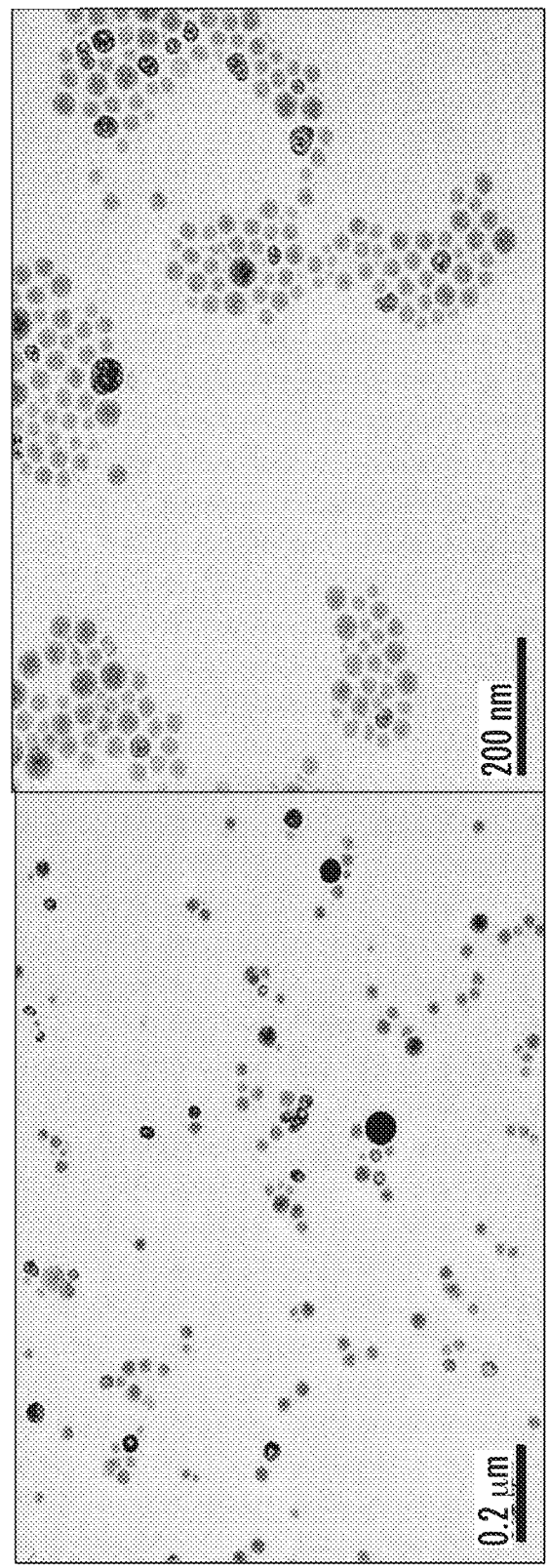
FIG. 41 is a pair of transmission electron microscopy (TEM) images of a pegylated version (DACHPtBp-Zn-PEG) of the nanoparticles described for FIG. 40.

Particle size, size distribution, and surface potential data for the cisPtBp-Zn-DOPA and cisPtBp-Zn-PEG nanoparticles are shown below in Table 6. TEM images for these nanoparticles are shown in FIGS. 38 and 39. Particle size, size distribution, and surface potential data for DACHPtBp-Zn-DOPA and DACHPtBp-Zn-PEG nanoparticles are shown below in Table 7. TEM images for these nanoparticles are shown in FIGS. 40 and 41.

TABLE 6

Particle size, size distribution, and surface potential of cisPtBp-Zn-DOPA and cisPtBp-Zn-PEG Nanoparticles

| particles | Z-Ave diameter (nm) | PDI | Zeta Potential (mV) |
|---|---|---|---|
| cisPtBp-Zn-DOPA | 51.23 ± 8.2 | 0.111 | NA |
| cisPtBp-Zn-PEG | 85.5 ± 10.1 | 0.140 | −0.92 ± 0.5 |

TABLE 7

Particle size, size distribution, and surface potential of DACHPtBp-Zn-DOPA and DACHPtBp-Zn-PEG Nanoparticles

| particles | Z-Ave diameter (nm) | PDI | Zeta Potential (mV) |
|---|---|---|---|
| DACHPtBp-Zn-DOPA | 48.7 ± 7.2 | 0.151 | NA |
| DACHPtBp-Zn-PEG | 91.4 ± 6.1 | 0.130 | −1.04 ± 0.6 |

Figure 42:
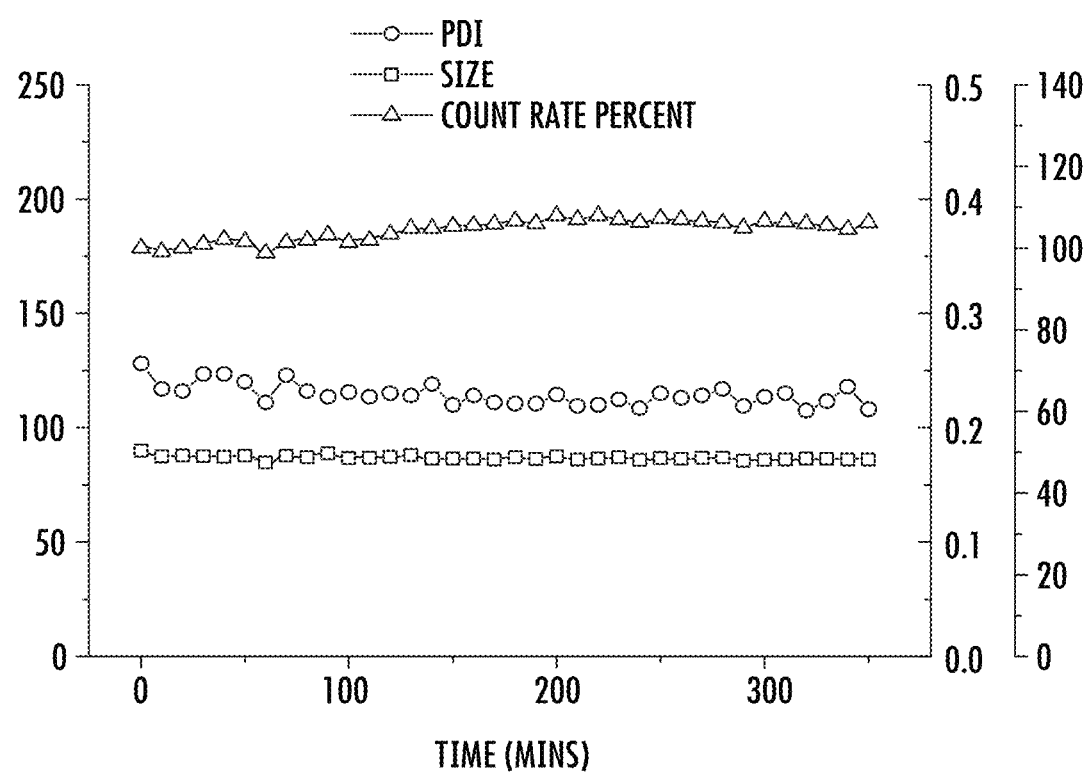
FIG. 42 is a graph showing the results of a stability test of the pegylated nanoparticles described in FIG. 39 (i.e., cisPtBp-Zn-PEG nanoparticles) in phosphate buffered saline (PBS) with bovine serum albumin (BSA). Data relating to the polydispersity index (PDI) of the nanoparticles is shown in circles; data relating to the nanoparticle size is shown in squares, and data relating to the count rate percent is shown in triangles.

4.5. Determination of Drug Loading and Release Profile: Drug loading of cisPtBp-Zn-PEG and DACHPtBp-Zn-PEG. Pre-weighted dry nanoparticles were digested in concentrated nitric acid overnight and then diluted with water for ICP-MS measurements. The cisplatin loading in cisPtBp-Zn-PEG was determined to be 20±5 wt. %, and the oxaliplatin loading in DACHPtBp-Zn-PEG was determined to be 18±3 wt. %. The results of a stability test of the cisPtBp-Zn-PEG nanoparticles in PBS buffer with BSA are shown in FIG. 42.

Figure 43A:
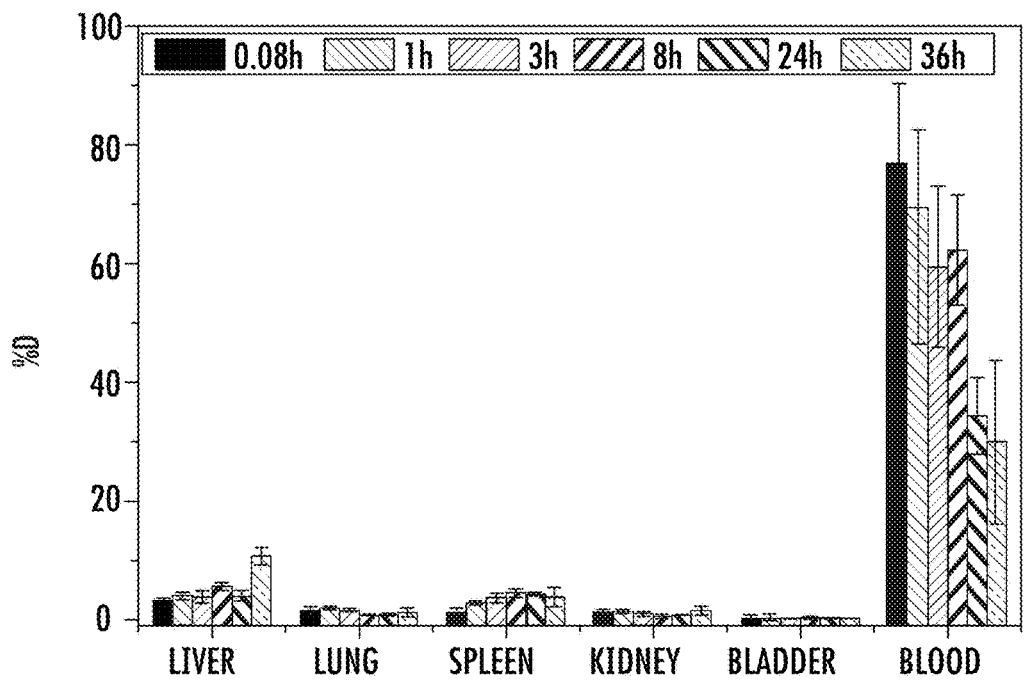
FIG. 43A is a bar graph showing the distribution of an injected dose (as a percentage (%) of the injected dose, % D) of the pegylated nanoparticles described for FIG. 39 (i.e., cisPtBp-Zn-PEG nanoparticles) in various organs (i.e., the liver, lung, spleen, kidney, bladder, and blood, as indicated in the x-axis) in mice. % D is provided at different time points (i.e., 0.08, 1, 3, 8, 24, and 36 hours, from left to right for each set of bars) post injection.
Figure 43B:
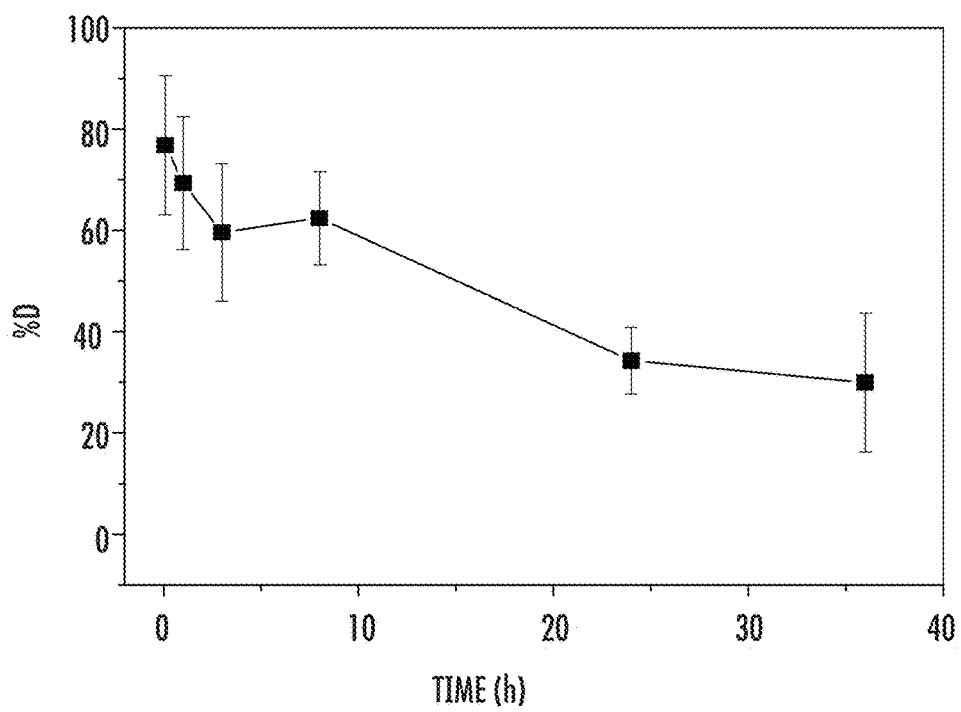
FIG. 43B is a graph showing the blood circulation profile of the nanoparticles described for FIG. 39 (i.e., cisPtBp-Zn-PEG nanoparticles) in mice.

4.6. Blood Circulation and organ distributions of cisPtBp-Zn-PEG nanoparticles. Normal mice were injected with cisPtBp-Zn-PEG nanoparticles at 3 mg/kg equivalent cisplatin doses via tail veins. The mice were sacrificed at different time points and their blood, liver, lung, spleen, kidney, and bladder were collected. These organs (and blood samples) were digested with concentrated nitric acid and analyzed for Pt contents by inductivity coupled plasma-mass spectroscopy (ICP-MS). The Pt distribution should track the cisplatin distribution in the form of intact particles circulating in the blood. Results are shown in FIGS. 43A and 43B. Greater than 50% of the injected dose remains in circulation for at least 15 hours.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A metal-bisphosphonate nanoparticle comprising a core comprising:
   (a) $M_1$, wherein $M_1$ is a multivalent metal ion; and
   (b) a bisphosphonate, wherein the bisphosphonate comprises a metal complex having the formula $M_2L_x$, wherein x is an integer of 2 or greater, $M_2$ is a second metal ion, and wherein each L is a metal ion ligand, further wherein at least two L are phosphonate group-containing metal ion ligands, wherein the phosphonate group of each of said phosphonate group-containing metal ion ligands is available to coordinate to multivalent metal ion $M_1$ and wherein the at least two phosphonate group-containing metal ion ligands are each coordinated to $M_2$ via a coordinative bond between $M_2$ and an oxygen atom of the phosphonate group-containing ligand.

2. The metal-bisphosphonate nanoparticle of claim 1, wherein the bisphosphonate comprises at least one metal ion ligand L that does not contain a phosphonate group.

3. The metal-bisphosphonate nanoparticle of claim 2, wherein the bisphosphonate comprises a metal ion ligand selected from the group consisting of halo, $NH_3$, alkylamino, hydroxyl, alkoxyl, diol, and diamine.

4. The metal-bisphosphonate nanoparticle of claim 2, wherein the bisphosphonate comprises a metal ion ligand that does not comprise a phosphonate group and wherein said ligand is a metal ion ligand other than $NH_3$ or diamine.

5. The metal-bisphosphonate nanoparticle of claim 1, wherein x is 5 or 6.

6. The metal-bisphosphonate nanoparticle of claim 1, wherein two L are $NH_3$.

7. The metal-bisphosphonate nanoparticle of claim 1, wherein two L are halo.

8. The metal-bisphosphonate nanoparticle of claim 1, wherein at least one L is a diamine.

9. The metal-bisphosphonate nanoparticle of claim 1, further wherein the oxygen atom of the phosphonate group-containing ligand coordinatively bound to $M_2$ is covalently bound to a carbon atom of the phosphonate group-containing ligand.

10. The metal-bisphosphonate nanoparticle of claim 9, wherein the carbon atom of the phosphonate group-containing ligand is a carbon atom of a carbonyl group.

11. A metal-bisphosphonate nanoparticle comprising a core comprising:
   (a) $M_1$, wherein $M_1$ is a multivalent metal ion; and
   (b) a bisphosphonate, wherein the bisphosphonate comprises a metal complex having the formula $M_2L_x$, wherein x is an integer of 2 or greater, $M_2$ is a second metal ion, and wherein each L is a metal ion ligand, further wherein at least two L are phosphonate group-containing metal ion ligands, wherein the phosphonate group of each of said phosphonate group-containing metal ion ligands is available to coordinate to multivalent metal ion $M_1$ and wherein each of the phosphonate group-containing metal ion ligands is coordinated to $M_2$ via a coordinative bond between $M_2$ and an oxygen atom of the phosphonate group-containing ligand, wherein said oxygen atom of the phosphonate group-containing ligand is covalently bound to a carbon atom of a thiocarbonyl group.

12. The metal-bisphosphonate nanoparticle of claim 1, wherein the bisphosphonate is prepared by reacting a metal complex comprising two hydroxyl ligands with a reagent selected from the group consisting of diethoxyphosphinyl isocyanate, diethoxyphosphinyl isothiocyanate, a diethyoxyphosphinyl-containing carboxylic anhydride, and a diethoxyphosphinyl-containing acyl chloride.

13. The metal-bisphosphonate nanoparticle of claim 1, wherein $M_2$ is a platinum ion.

14. The metal-bisphosphonate nanoparticle of claim 1, wherein $M_1$ is $Zn^{2+}$.

15. The metal-bisphosphonate nanoparticle of claim 1, wherein the nanoparticle further comprises one or more coating agents or layers surrounding at least a portion of an outer surface of the core.

16. The metal-bisphosphonate nanoparticle of claim 15, wherein the nanoparticle comprises at least one lipid coating layer or agent.

17. The metal-bisphosphonate nanoparticle of claim 15, wherein one or more coating agents or layers comprise a targeting moiety or a passivating moiety.

18. A pharmaceutical composition comprising a metal-bisphosphonate nanoparticle of claim 1 and a pharmaceutically acceptable carrier.

19. A method of treating cancer in a subject in need of treatment thereof, wherein the method comprises administering to said subject an effective amount of a metal-bisphosphonate nanoparticle of claim 1.

* * * * *